(12) United States Patent
Adams et al.

(10) Patent No.: US 8,329,873 B2
(45) Date of Patent: Dec. 11, 2012

(54) BISPECIFIC SINGLE CHAIN FV ANTIBODY MOLECULES AND METHODS OF USE THEREOF

(75) Inventors: Gregory P. Adams, Hatboro, PA (US); Eva M. Horak, West Orange, NJ (US); Louis M. Weiner, Philadelphia, PA (US); James D. Marks, Kensington, CA (US)

(73) Assignees: The Regents of the University of California, Oakland, CA (US); Fox Chase Cancer Center, Philadelphia, PA (US)

( * ) Notice: Subject to any disclaimer, the term of this patent is extended or adjusted under 35 U.S.C. 154(b) by 827 days.

(21) Appl. No.: 11/943,367

(22) Filed: Nov. 20, 2007

(65) Prior Publication Data

US 2009/0010840 A1 Jan. 8, 2009

Related U.S. Application Data

(60) Division of application No. 11/154,103, filed on Jun. 15, 2005, now Pat. No. 7,332,585, which is a continuation-in-part of application No. 10/406,830, filed on Apr. 4, 2003, now Pat. No. 7,332,580.

(60) Provisional application No. 60/370,276, filed on Apr. 5, 2002.

(51) Int. Cl.
*C07K 16/00* (2006.01)
(52) U.S. Cl. ............... 530/387.7; 424/130.1; 424/136.1; 424/138.1
(58) Field of Classification Search .................... None
See application file for complete search history.

(56) References Cited

U.S. PATENT DOCUMENTS

| 4,444,878 A | 4/1984 | Paulus |
| 4,801,575 A | 1/1989 | Pardridge |
| 4,902,505 A | 2/1990 | Pardridge et al. |
| 5,292,668 A | 3/1994 | Paulus |
| 5,523,210 A | 6/1996 | Paulus |
| 5,601,819 A | 2/1997 | Wong et al. |
| 5,932,448 A | 8/1999 | Tso et al. |
| 5,959,084 A | 9/1999 | Ring et al. |
| 5,977,322 A | 11/1999 | Marks et al. |
| 5,985,276 A | 11/1999 | Lindhofer et al. |
| 5,990,275 A | 11/1999 | Whitlow et al. |
| 6,010,902 A | 1/2000 | Ledbetter et al. |
| 6,060,285 A | 5/2000 | Lenz et al. |
| 6,106,833 A | 8/2000 | Ring et al. |
| 6,129,914 A | 10/2000 | Weiner et al. |
| 6,210,668 B1 | 4/2001 | Lindhofer et al. |
| 6,245,523 B1 | 6/2001 | Altieri |
| 6,287,792 B1 | 9/2001 | Pardridge et al. |
| 6,451,980 B1 | 9/2002 | Khaw et al. |
| 6,458,933 B1 | 10/2002 | Hansen |
| 6,512,097 B1 | 1/2003 | Marks et al. |
| 6,723,538 B2 | 4/2004 | Mack et al. |
| 6,794,128 B2 | 9/2004 | Marks et al. |
| 7,332,580 B2 | 2/2008 | Adams |
| 7,332,585 B2 | 2/2008 | Adams et al. |
| 2001/0036459 A1 | 11/2001 | Ravetch |
| 2002/0132990 A1 | 9/2002 | Huston et al. |
| 2004/0071696 A1 | 4/2004 | Adams et al. |
| 2004/0071896 A1 | 4/2004 | Kang et al. |
| 2009/0010840 A1 | 1/2009 | Adams et al. |
| 2010/0196265 A1 | 8/2010 | Adams et al. |

FOREIGN PATENT DOCUMENTS

| EP | 592 564 | 9/2006 |
| EP | 1 187 634 B1 | 12/2007 |
| EP | 1 889 631 A1 | 2/2008 |
| WO | WO 00/78347 A1 | 12/2000 |
| WO | WO02-00914 | 1/2002 |
| WO | WO02/00914 * | 1/2002 |
| WO | WO2004-032961 | 4/2004 |
| WO | WO2007-084181 | 7/2007 |
| WO | WO2008-140493 | 11/2008 |

OTHER PUBLICATIONS

U.S. Appl. No. 12/515,522, filed May 19, 2009, Adams et al.
U.S. Office Action dated Mar. 14, 2007 issued in U.S. Appl. No. 10/406,830.
U.S. Notice of Allowance dated Aug. 07, 2007 issued in US. Appl. No. 10/406,830.
U.S. Notice of Allowance dated Sep. 17, 2007 issued in U.S. Appl. No. 11/154,103.
PCT International Search Report dated Jun. 17, 2008 issued in W02007084181.
PCT International Preliminary Examination Report dated Jul. 22, 2008 issued in W02007084181.
PCT Written Opinion dated Jun. 17, 2008 issued in W02007084181.
PCT International Search Report dated Mar. 20, 2009 issued in W02008140493.
PCT Written Opinion dated Mar. 20, 2009 issued in W02008140493.
PCT International Preliminary Examination Report dated May 26, 2009 issued in W02008140493.
Adams et al. (1992) "Comparison of the Pharmacokinetics in Mice and the Biological Activity of Murine L6 and Human-Mouse Chimeric Ch-L6 Antibody." *Antibody, Immunoconjugates and Radiopharmaceuticals*, vol. 5(1): pp. 81-95.
Adams et al. (1993) "Highly specific in vivo tumor targeting by monovalent and divalent forms of 741 F8 anti-c-erbB-2 single-chain Fv." *Cancer Research*, vol. 43(17): pp. 4026-4034.
Adams et al.(1996) "Influence of avidity on the tumor retention of monospecific and bispecific anti-c-erbB-2 single-chain Fv dimers." *Proceedings of the American Association of Cancer Research*, No. 3217: p. 472.
Agrawal et al. (1991) "Pharmacokinetics, biodistribution, and stability of oligodeoxynucleotide phosphorothioates in mice." *Proceedings of the National Academy of Sciences*, USA, vol. 88(17): pp. 7595-7599.
Beaumier et al. (1985) "Melanoma localization in nude mice with monoclonal Fab against p97."*The Journal of Nuclear Medicine*, vol. 26: pp. 1172-1179.

(Continued)

*Primary Examiner* — Laura B Goddard
*Assistant Examiner* — Meera Natarajan
(74) *Attorney, Agent, or Firm* — Tom Hunter; Weaver Austin Villeneuve & Sampson LLP

(57) ABSTRACT

Bispecific single chain antibody molecules are disclosed which may be used to advantage to treat various forms of cancer associated with the overexpression of members of the EGFR protein family.

17 Claims, 15 Drawing Sheets

OTHER PUBLICATIONS

Berger et al. (1988) "Correlation of c-erbB-2 gene amplification and protein expression in human breast carcinoma with nodal status and nuclear grading." *Cancer Research*, vol. 48(5): pp. 1238-1243.

Boado and Pardridge (1994) "Complete Inactivation of Target mRNA by Biotinylated Antisense Oligodcoxynucleotide-Avidin Conjugates." *Bioconjugate Chem.*, vol. 5: pp. 406-410.

Boado and Pardridge (1998) "Ten nucleotide cis element in the 3'-untranslated region of the GLUT1 glucose transporter mRNA increases gene expression via mRNA stabilization." *Molecular Brain Research*, vol. 59: pp. 109-113.

Boado et al. (1998) "Drug Delivery of Antisense Molecules to the Brain for Treatment of Alzheimer's Disease and Cerebral AIDS." *Journal of Pharmaceutical Sciences*, vol. 87(11): pp. 13081315.

Boado et al. (1999) "Selective expression of the large neutral amino acid transporter at the blood-brain barrier." *Proceedings of the National Academy of Sciences*, USA, vol. vol. 96(21): pp. 1207912084.

Boado et al. (2000) "Antisense-Mediated Down-Regulation of the Human Huntingtin Gene." *The Journal of Pharmacology and Experimental Therapeutics*, vol. 295(1): pp. 239-243.

Brown et al. (1994) "Effect of Phosphorothioate Modification of Oligodeoxynucleotides on Specific Protein Binding." *The Journal of Biological Chemistry*, vol. 269(43): pp. 26801-26805.

Cam and Lam (2003) "Bispecific antibody conjugates in therapeutics." *Advanced Drug Delivery Reviews*, vol. 55(2): pp. 171-197.

Cao and Lam (2003) "Bispecific antibody conjugates in therapeutics," *Advanced Drug Delivery Reviews*, 55 (2): 171-197.

Chem et al. (1990) "Disposition and metabolism of oligodeoxynucleoside methylphosphonate following a single iv injection in mice." *Drug Metabolism Disposition*, vol. 8 (5): pp. 815-818.

Chinnery et al. (1999) "Peptide nucleic acid delivery to human mitochondria" *Gene Therapy*, vol. 6: pp. 1919-1928.

Colcher et al. (1990) "In Vivo Tumor Targeting of a Recombinant Single-Chain Antigen- Binding Protein," *Journal of the National Cancer Institute*, vol. 82(14): pp. 1191-1197.

Coloma et al. (2000) "Transport Across the Primate Blood-Brain Barrier Of a Genetically Engineered Chimeric Monoclonal Antibody to the Human Insulin Receptor." *Pharmaceutical Research*, vol. 17 (3): pp. 266-274.

Cossum et al. (1993) "Disposition of the 14C-labeled phosphorothioate oligonucleotide ISIS 2105 after intravenous administration to rats" *The Journal of Pharmacology Experimental Therapeutics*, vol. 267: pp. 1181-1190.

Crooke (1993) "Progress toward oligonucleotide therapeutics: pharmacodynamic properties." *FASEB Journal*, vol. 7 (6): pp. 533-539.

Cruse and Lewis (2003) *Atlas of Immunology, 2nd Edition*, Chapter: Immunoglobulin, Systhesis, Properties, Structure and Function, 2003, pp. 184-185.

de Smidt et al. (1991) "Association of antisense oligonucleotides with lipoproteins prolongs the plasma half-life and modifies the tissue distribution." *Nucleic Acids Research*, vol. 19, No. 17, pp. 4695-4700.

Demidov et al. (1994) "Stability of peptide nucleic acids in human serum and cellular extracts." *Biochemical Pharmacology*, vol. 48: pp. 1310-1313.

Gee et al. (1998) "Assessment of High-Affinity Hybridization, rNase H Cleavage, and Covalent Linkage in Translation Arrest by Antisense Oligonucleotides." *Antisense and Nucleic Acid Drug Develop*, 8:103-111.

Hanvey et al. (1992) "Antisence and Antigene Properties of Peptide Nucleic Acids." *Science*, 258:1481-1486.

Heffetz et al. (1989) "Antibodies directed against phosphothreonine residues as potent tools for studying protein phosphorylation." *European Journal of Biochemistry*, 182: 343-348.

Heiss (2003) "Invivo Efficacy of Trifunctional Bispecific Antibodies in Treatment of Symptomatic Malignant Ascities." *Proceedings of the American Society of Clinical Oncology*, vol. 22: p. 173 (abstract 693).

Hnatowich (1999) "Antisense and nuclear medicine." *The Journal of Nuclear Medicine*, 40(4): 693-703.

Holliger et al. (1993) "'Diabodies': Small bivalent and bispecific antibody fragments." *Proceedings of the National Academy of Sciences*, USA, 90(14): 6444-6448.

Hu et al. (1996) "Minibody: A Novel Engineered Anti-Carcinoembryonic Antigen Antibody Fragment (Single-Chain Fv-CH3) Which Exhibits Rapid, High-Level Targeting of Xenografts." *Cancer Research*, 56: 3055-3061.

Hurwitz et al. (1995) "Suppression and promotion of tumor growth by monoclonal antibodies to ErbB-2 differentially correlate with cellular uptake." *Proceedings of the National Academy of Sciences*, USA, 9vol. 92(8): pp. 3353-3357, Apr. 11, 1995.

Huwyler and Pardridge (1998) "Examination of Blood—Brain Barrier Transferrin Receptor by Confocal Fluorescent Nicroscopy of Unfixed Isolated Rat Brain Capillaries." *Journal of Neurochemistry*, vol. 70: pp. 883-886.

Hynes and Stern (1994) "The biology of erbB-2/HER-2 and its role in cancer." *Biochimica et Biophysica Acta*, 1198: 165-184.

Kallies et al. (1994) "Binding of Ribosomes to the Rough Endoplasmic Reticulum Mediated by the Sec61p-Complex," *Journal of Cell Biology*, vol. 126, No. 4, pp. 925-934.

Kang et al. (1995) "Pharmacokinetics and organ clearance of a 3'-biotinylated, internally [32P]-labeled phosphodiester oligodeoxynucleotide coupled to a neutral avidin/monoclonal antibody conjugate." *Drug Metabolism and Disposition*, 23(1): 55-59.

Kobori et al. (1999) "Visualization of mRNA expression in CNS using $^{11}$C-labeled phosphorothioate oligodeoxynucleotide." *NeuroReport*, 10: 2971-2974.

Krieg et al. (1993) "Modification of antisence phosphodiester oligodeoxynucleotides by a 5' cholesteryl moiety increases cellular association and improves efficacy." *Proceedings of the National Academy of Sciences*, USA, 90(3): 1048-1052.

Kroesen et al. (1998) "Bispecific antibodies for treatment of cancer in experimental animal models and man." *Advanced Drug Delivery Reviews*, 31(1): 105-129.

Kurihara and Pardridge (1999) "Imaging Brain Tumors by Targeting Peptide Radiopharmaceuticals through the Blood-Brain Barrier." *Cancer Research*, 54: 6159-6163.

Kurihara et al. (1999) Epidermal Growth Factor Radiopharmaceuticals: $^{111}$In Chelation, Conjugation to a Blood-Brain Barrier Delivery Vector via a Biotin-Polyethlene Linker, Pharacokinetics, and in Vivo Imaging of Experimental Brain Tumors. *Bioconjugate Chem.*, 10: 502-511.

Langley et al. (1998) Identification of Multiple Forms of 180-kDa Ribosome Receptor in Human Cell, *DNA and Cell Biology*, vol. 17, No. 5, pp. 449-460.

Lee et al. (2000 "Targeting Rat Anti-Mouse Transferrin Receptor Monoclonal Antibodies through Blood-Brain Barrier in Mouse." *The Journal of Pharmacology and Experimental Therapeutics*, 292(3): 1048-1052.

Li et al. (1999) "Genetically engineered brain drug delivery vectors: cloning, expression and in vivo application of an anti-transferrin receptor single chain antibody—atreptavidin fusion gene and protein." *Protein Engineering*, 12(9): 787-796.

Lockhard and Winzeler (2000) "Genomics, gene expression and DNA arrays." *Nature*, 405: 827-836.

Lohrisch and Piccart (2001) "An Overview of HER2." *Seminars in Oncology*, 28(6) Suppl 18: 3-11.

Mash et al. (1990) "Characterization and Distribution of Transferrin Receptors in the Rat Brain." *Journal of Neurochemistry*, 55: 1972-1979.

Mayfield and Corey (1999) "Automated Synthesis of Peptide Nucleic Acids and Peptide Nucleic Acid—Peptide Conjugates," *Analytical Biochemistry*, vol. 268: pp. 401-404.

Milenic et al. (1991) "Construction, Binding Properties, Metabolism, and Tumor Targeting of a Single-Chain Fv Derived from the Pancarcinoma Monoclonal Antibody CC49." *Cancer Research*, 51: 6363-6371.

Nielsen et al. (1994) "Peptide Nucleic Acid (PNA). A DNA Mimic with a Peptide Backbone." *Bioconjugate Chem.*, vol. 5: pp. 3-7.

O'Reilly et al. (1991) "The relationship between c-erbB-2 expression, S-phase fraction and prognosis in breast cancer." *British Journal of Cancer*, vol. 63: pp. 444-446.

Pack and Pluckthun (1992) "Miniantibodies: use of amphipathic helixes to produce functional, flexibly linked dimeric FV fragments with high avidity in *Escherichia coli*." *Biochemistry*, vol. 31(6): pp. 1579-1584.

Pack et al. (1993) "Improved Bivalent Miniantibodies, with Identical Avidity as Whole Antibodies, Produced by High Cell Density Fermentation of *Escherichia coli*." *Bio/Technology*, vol. 11: 1271-1277.

Pardridge (1997) "Drug Delivery to the Brain." *Journal of Cerebral Blood Flow and Metabollism*, vol. 17:713-731.

Pardridge (2001) "Drug targeting," *Drug Discovery Today*, vol. 6(2): pp. 104-106, Jan. 2001.

Pardridge et al. (1995) "Human Insulin Receptors Monoclonal Antibody Undergoes High Affinity Binding to Human Brain Capillaries in Vitro and Rapid Transcytosis Through the Blood-Brain Barrier in vivo in the Primate." *Pharmaceutical Research*, 12(6): 807-816.

Pardridge et al. (1995) "Vector-mediated delivery of a polyamide ('peptide') nucleic acid analogue through the blood-brain barrier in vivo." *Proceedings of the National Academy of Sciences, USA*, 92(12): 5592-5596.

Paul, William E. (1993) *Fundamental Immunology, 3rd Edition*, Raven Press Ltd, New York, NY., pp. 292-295.

Penichet et al. (1999) "An Antibody-Avidin Fusion Protein Specific for the Transferrin Receptor Serves as a Delivery Vehicle for Effective Brain Tergeting: Initial Applicaions in Anti- HIV Antisence Drug Delivery to the Brain." *The Journal of Immunology*, 163: 4421-4426.

Press et al. (1993) "Her-2/neu expression in node-negative breast cancer: direct tissue quantitation by computerized image analysis and association of overexpression with increased risk of recurrent disease." *Cancer Research*, 53(20): 4960-4970.

Pullarkat et al. (1999) "A phase I study of a HER2/neu bispecific antibody with granulocyte-colony-stimulating factor in patients with metastatic breast cancer that overexpresses HER2/neu," *Cancer Immunol. Immunother*, vol. 48, pp. 9-21, Apr. 1999.

Rebert et al. (1990) "Acute Interactive Pharmacologic Effects of Inhaled Toluene and Dichloromethane on Rat Brain Electrophysiology." *Pharmacology Biochemistry & Behavior*, 36: 351-356.

Rockwell et al. (1997) "Cell-surface perturbations of the epidermal growth factor and vascular endothelial growth factor receptors by phosphorothioate oligodeoxynucleotides." *Proceedings of the National Academy of Sciences, USA,*, 94(12): 6523-6528.

Rudikoff et al. (1982) "Single amino acid substitution altering antigen-binding specificity," *Proc. Natl. Acad. Sci. USA*, vol. 79, pp. 1979-1983, Mar. 1982.

Samii et al. (1994) "Blood-brain barrier transport of neuropeptides: analysis with a metabolically stable dermorphin analogue." *American Journal of Physiology*, 267: E124-E134.

Sathasivam et al. (1999) Transgenic models of huntington's disease. *Philosophical Transactions of The Royal Society of London*, 354: 963-969.

Savitz and Meyer (1990) "Identification of a ribosome receptor in the rough endoplasmic reticulum," *Nature*, vol. 346: pp. 540-544, Aug 9, 1990.

Savitz and Meyer (1993) "180-kD Ribosome Receptor is Essential for Both Ribosome Binding and Protein Translocation," *Journal of Cell Biology*, vol. 120, No. 4, pp. 853-863, Feb. 1993.

Schier et al. (1995) "In vitro and in vivo characterization of a human anti-c-erbB-2 single- chain Fv isolated from a filamentous phage antibody library." *Immunotechnology*, vol. 1: pp. 73-81.

Schier et al. (1996) "Isolation of High-affinity Monomeric Human Anti-c-erbB-2 Single chain Fv Using Affinity-driven Selection." *Journal of Molecular Biology*, 255(1): 28-43.

Schicr et al. (1996) "Isolation of Picomolar Affinity Anti-c-crbB-2 Single-Chain Fv by Molecular Evolution of the Complementarity Determining Regions in the Center of the Antibody Binding Site." *Journal of Molecular Biology*, 263(4): 551-567.

Schier, et al. (1996) "Isolation of Picomolar Affinity Anti-c-erbB-2 Single-chain Fv by Molecular Evolution of the Complementarity Determining Regions in the Center of the Antibody Binding Site," *J. Mol. Biol.*, vol. 263(4): pp. 551-567.

Seshadri et al. (1993) "Clinical significance of HER-2/neu oncogene amplification in primary breast cancer." The South Australian Breast Cancer Study Group; *Journal of Clinical Oncology*. 11(10): 1936-1942.

Shalaby et al. (1992) "Development of Humanized Bispecific Antibodies Reactive with Cytotoxic Lymphocytes and Tumor Cellt Overexpressing the HER2 Protooncogne." *Journal of Experimental Medicine*, vol. 175: pp. 217-225, Jan. 1992.

Shalaby et al. (1995) "Bispecific HER2 X CD3 Antibodies Enhance T-Cell Cytotoxicity in Vitro and Localize to HER2-Overexpressing Xenographs in Nude Mice." *Clinical Immunology and Immunopathology*, vol. 74(2): pp. 185-192.

Shechter et al. (1982) "Autoantibodies to Insulin Receptors Spontaneously Develop an Anti-Idiotypes in Mice Immunized with Insulin." *Science*, 216: 542-545.

Shi and Pardridge (2000) "Noninvasive gene targeting to the brain." *Proceedings of the National Academy of Sciences, USA*, 97(13): 7567-7572.

Shi et al. (2000) "Antisense imaging of gene expression in the brain in vivo." *Proceedings of the National Academy of Sciences, USA*, 97(26): 14709-14714.

Skarlatos et al. (1995) "Transport of [$^{125}$I] transferrin through the rat blood-brain barrier." *Brain Research*, 683: 164-171.

Slamon et al. (1989) "Studies of the HER-2/neu Proto-oncogene in Human Breast and Ovarian Cancer." *Science*, vol. 244 (4905): pp. 707-712.

Slamon et al. (1987) "Human Breast Cancer: Correlation of Relapse and Survival with Amplification of the HER-2/neu Oncogene." *Science*, 235: 177-181.

Stancovski et al. (1991) "Mechanistic aspects of the opposing effects of monoclonal antibodies to the ERBB2 receptor on tumor growth," *Proceedings of the National Academy of Sciences, USA*, vol. 88, No. 19: pp. 8691-8695.

Stein and Cheng (1993) "Antisense Oligonucleotides as Therapeutic Agents—Is the Bullet Really Magicdl?" *Science*, 261: 1004-1012.

Tavitian et al. (1998) "In vivo imaging of oligonucleotides with positron emission tomography." *Nature Medicine*, 4(4): 467-471.

Tsukamoto et al. (1997) "Site-Directed Deletion of a 10-Nucleotide Domain of the 3'-Untranslated Region of the GLUT1 Glucose Transporter mRNA Eliminates Cytosolic Protein Binding in Human Brain Tumors and Induction of Reporter Gene Expression." *Journal of Neurochemistry*, 68: 2587-2592.

Tyler et al. (1999) "Peptide nucleic acids targeted to the neurotensin receptor and administered i.p. cross the blood-brain barrier and specifically reduce gene expression." *Proceedings of the National Academy of Sciences, USA*, 96(12): 7053-7058.

Ueda et al. (1993) "Rate of $^{59}$Fe Uptake into Brain and Cerebrospinal Fluid and the Influence Thereon of Antibodies Against the Transferrin Receptor." *Journal of Neurochemistry*, 60: 106-113.

Wanker et al. (1995) Functional Characterization of the 180-kD Ribosome Receptor in ViVo, *Journal of Cell Biology*, vol. 130, No. 1, pp. 29-39.

Whitesell et al. (1993) "Stability, clearance, and disposition of intraventricularly administered oligodeoxynucleotides: Implications for therapeutic application within the central nervous system." *Proceedings of the National Academy of Sciences, USA*, 90(10): 4665-4669.

Wickstrom (1986) "Oligodcoxynucleotide stability in subcellular extracts and culture media." *Journal of Biochemical and Biophysical Methods*, vol. 13: pp. 97-102.

Wild et al. (1999) "Tumor Therapy with Bispecific Antibody: The Tergeting and Triggering Steps Can Be Separated Employing a CD2-Based Strategy." *The Journal of Immunology*, vol. 163, No. 4: pp. 2064-2072. Erratum in: The Journal of Immunology (2000) vol. 164(10): p. 5531.

Wittung et al. (1994) "DNA-like double helix formed by peptide nucleic acid." *Nature*, vol. 368: pp. 561-563.

Wojcik et al. (1996) "Chronic intrathecal infusion of phosphorothioate or phosphodiester antisense oligonucleotides against cytokine responsive gene-2/IP-10 in experimental allergic encephalomyelitis of lewis rat." *The Journal of Pharmacology and Experimental Therapeutics*, vol. 278(1): pp. 404-410.

Wolf et al. (1993) "Monoclonal antibody homodimers: enhanced antitumor activity in nude mice." *Cancer Research*, 53(11): 2560-2565.

Wu et al. (1996) "Pharmacokinetics and blood-brain barrier transport of [3H]-biotinylated phosphorothioate oligodeoxynucleotide conjugated to a vector-mediated drug delivery system." *The Journal of Pharmacology and Experimental Therapeutics*, 276(1): 206-211.

Yarden and Sliwkowski (2001) "Untangling The ErbB Singalling Network." *Nature, Reviews, Molecular Cell Biology*, 2: 127-137.

Zendegui et al. (1992) "In vivo stability and kinetics of absorption and disposition of 3' phosphopropy amine oligonucleotides." *Nucleic Acids Research*, 20(2): 307-314.

Zhang and Pardridge (2001) "Rapid transferrin efflux from brain to blood across the blood-brain Barrier." *Journal of Neurochemistry*, 76: 1597-1600.

Zhao et al. (1999) "Brain Insulin Receptors and Spatial Memory." *The Journal of Biological Chemistry*, 274(49): 34893-34902.

Zhou et al. (2000) "HER-2/neu Blocks Tumor Necrosis Factor-induced Apoptosis via the Akt/NF-KB Pathway." *The Journal of Biological Chemistry*, 275(11): 8027-8031.

Zick et al. (1984) "The Role of Antireceptor Antibodies in Stimulating Phosphorylation of the Insulin Receptor." *The Journal of Biological Chemistry*, 259(7): 4396-4400.

McCall et al. (2001) "Increasing the Affinity for Tumor Antigen Enhances Bispecific Antibody Cytrotoxicity", *J. Immunol.*, 166:6112-6117.

Baselga, José (2002) "Why the Epidermal Growth Factor Receptor? The Rationale for Cancer Therapy", *The Oncologist* 7(suppl 4):2-8 [Downloaded from www.TheOncologist.com on Nov. 21, 2008].

European Supplementary Search Report dated Apr. 23, 2009 issued in EP 06784990.

European Examination Report-1 dated Aug. 20, 2009 issued in EP 06784990.1.

European Examination Report-2 dated Mar. 19, 2010 issued in EP 06784990.1.

Desplancq et al. (1994), "Multimerization Behaviour of Single Chain Fv Variants for the Tumour-binding Antibody B72.3," *Protein Eng.*, Oxford Unv. Press, Surrey, GB, vol. 7, No. 8, Aug. 1, 1994; XP0004450771; ISSN: 0269-2139; pp. 1027-1033.

Schmidt, M. et al (1996) "A Bivalent Single-Chain Antibody-Toxin Specific for ERB-2 and the EGF Receptor," *Intn'l Jnl of Cancer*, John Wiley & Sons, Inc., US, Switzerland, Germany, vol. 65, No. 4, Feb. 8, 1996, XP000646380, ISSN: 0020-7136; pp. 538-546.

Chinese First Office Action dated Jan. 4, 2011 issued in CN200680029687.5.

Chinese Notice of Payment of the Restoration Fee for Unity of Invention dated Sep. 1, 2010 issued in CN200680029687.5.

Response including references to European Patent Office dated Sep. 28, 2010 regarding EP Office Action of Mar. 19, 2010 issued in EP 06 784 990.1.

European Summons to attend Oral Proceedings pursuant to Rule 115(1) EPC dated Nov. 2, 2010 issued in EP 06 784 990.1-2406 / 1912674.

Adams et al. (Sep. 1, 1993) "Highly specific in vivo tumor targeting by monovalent and divalent forms of 741F8 anti-c-*erb*B-2 single-chain Fv", Cancer Research, vol. 53(17): pp. 4026-4034.

Adams et al. (Feb. 1, 1998) "Increased Affinity Leads to Improved Selective Tumor Delivery of Single-Chain Fv Antibodies", *Cancer Research*, 58:485-490.

Adams et al. (Sep. 2005) "Monoclonal antibody therapy of cancer", *Nature Biotechnology*, 23(9):1147-1157.

Adams et al. (Mar. 1, 2006) "Avidity-Mediated Enhancement of *In vivo* Tumor Targeting by Single-Chain Fv Dimers", Clinical Cancer Research, 12(5):1599-1605.

Beckman et al. (Jan. 15, 2007) "Antibody Constructs in Cancer Therapy, *Protein Engineering Strategies to Improve Exposure in Solid Tumors*", American Cancer Society, 109(2):170-179.

Horak et al. (Nov. 6, 2005) "Isolation of scFvs to *In Vitro* Produced Extracellular Domains of EGFR Family Members", *Cancer Biotherapy & Radiopharmaceuticals* 20(6):603-614.

Keler et al. (Sep. 15, 1997) "Bispecific Antibody-dependent Cellular Cytotoxicity of HER2/*neu*-overexpressing Tumor Cells by Fcγ Receptor Type I-expressing Effector Cells", *Cancer Research*, 57:4008-4014.

Normanly et al. (Sep. 1986) "Construction of two *Escherichia coli* amber suppressor genes: tRNA CUA$^{Phe}$ and tRNA CUA$^{CYC}$", *Proc. Natl. Acad. Sci. USA*, 83:6548-6552.

Robinson et al. (2008) "Targeting ErbB2 and ErbB3 with a bispecific single-chain Fv enhances targeting selectivity and induces a therapeutic effect *in vitro*", British Journal of Cancer, 99:1415-1425 doi:10.1038/sj.bjc.6604700[Published online Oct. 7 2008].

Shahied et al. (Issue of Dec. 24, 2004) "Bispecific Minibodies Targeting HER2/*neu* and CD16 Exhibit Improved Tumor Lysis When Placed in a Divalent Tumor Antigen Binding Format", *The Journal of Biological Chemistry*, 279(52):53907-53914.

Weiner et al. (Jan. 1, 1993) "A Human Tumor Xenograft Model of Therapy with a Bispecific Monoclonal Antibody Targeting c-*erb*B-2 and CD16", Cancer Research, 53:94-100.

Australian Office Action dated Apr. 18, 2011 issued in AU2006336279.

European Communication under Rule 71(3) EPC for Grant (Bibliographical data; Description) dated Apr. 11, 2011 issued in EP 06 784 990.1-406, 106 pages.

European Communication regarding Result of Consultation (Feb. 16, 2011) dated Feb. 23, 2011 issued in EP 06 784 990.1-2406, 3 pages.

European Brief Communication dated Feb. 22, 2011 (faxed Feb. 17, 2011) issued in EP 06 784 990.1-2406, 7 pages.

European prosecution letter and copy of amended claims dated Feb. 16, 2011 issued in EP 06 784 990.1-2406, 102 pages.

European Communications dated Feb. 11, 2011 and Feb. 9, 2011 (regarding claims and filed amendments) issued in EP 06 784 990.1-2406, 59 pages.

European Communication regarding filed amendments, claims and replacement sequence listing dated Feb. 7, 2011 issued in EP 06 784 990.1-2406, 42 pages.

European Communication regarding result of consultation (Feb. 1, 2011) dated Feb. 9, 2011 issued in EP 06 784 990.1-2406, 5 pages.

European Communication regarding Result of consultation dated Feb. 1, 2011 (with letter dated Jan. 20, 2011 including claims, Declaration and prosecution) issued in EP 06 784 990.1-2406, 56 pages.

European Communication regarding Oral Proceedings (Main Request Claims; Replacement pages; First and Second Auxiliary Request claims; Replacement sequence listing; Declaration by Dr. Ulrik Nielsen, including Appendices I-III and Figures 1-9) dated Dec. 21, 2010 issued in EP 06 784 990.1-2406, 10 pages.

European Communication regarding Summons to attend oral proceedings pursuant to Rule 115(1) EPC dated Nov. 2, 2010 issued in EP 06 784 990.1-2406, 11 pages.

European letter in response to communication dated Mar. 19, 2010 (with claims; Stratagene technical information; Normanly et al. article; Replacement pp. 9 and 10 of sequence listings) dated Sep. 28, 2010 issued in EP 06 784 990.1-2406, 18 pages.

European Communication dated Jul. 27, 2010 and Extension of Time dated Jul. 20, 2010 issued in EP 06 784 990.1-2406, 3 pages.

European Examination Report dated Mar. 19, 2010 issued in EP 06 784 990.1-2406, 7 pages.

European Response to Communication of Aug. 20, 2009 (including Amended claims; marked up claims; Sequence listing in TXT and PDF format) dated Dec. 23, 2009 issued in EP 06 784 990.1-2406, 12 pages.

European Examination Report dated Aug. 20, 2009 issued in EP 06 784 990.1-2406, 3 pages.

European Communication (with Amended claims 1-25, Form 1005) dated Jul. 20, 2009 issued in EP 06 784 990.1-2406, 6 pages.

European Communication dated May 12, 2009 with European Supplementary Search Report dated Apr. 23, 2009 issued in EP 06 784 990.1-2406, 10 pages.

European Communication dated Mar. 5, 2009 (including Invitation dated Jan. 8, 2009; sequence listing; Annex) issued in EP 06 784 990.1-2406, 6 pages.

European Communication (with amended claims; Form 1037) dated Nov. 4, 2008 issued in EP 06 784 990.1-2406, 15 pages.

European Communication (PCT prosecution documents) dated Oct. 10, 2008 issued in EP 06 784 990.1-2406, 13 pages.

Chinese Second Office Action dated Sep. 9, 2011 issued in CN200680029687.5.

EP Grant Documents for patent dated Nov. 9, 2011 issued in EP 06 784 990.1-2406, 8 pages.

EP Documents for Grant of a patent dated Aug. 30, 2011 issued in EP 06 784 990.1-2406, 4 pages.

Response to EP Communication under Rule 71(3) EPC for Grant (Apr. 11, 2011) dated Aug. 17, 2011 issued in EP 06 784 990.1-2406, 18 pages.
Japanese Office Action dated Seo. 30, 2011 issued in JP2008-517139.
Chinese Decision on Rejection dated Jun. 12, 2012 issued in CN200680029687.5.

EP Correction of a decision under Rule 140 EPC dated Mar. 7, 2012 issued in EP 06 784 990.1-2406, 1 page.
European Extended Search Report dated Apr. 19, 2012 issued in EP 11 177 829.6-2406/2425850.

* cited by examiner

Heavy Chain:

| Clone | Framework 1 | CDR1 | Framework 2 | CDR2 |
|---|---|---|---|---|
| C6.5 | QVQLVQSGAEVKKPGESLKISCKGSGYSFT | SYWIA | WVRQMPGKGLEYMG | LIYPGDSDTKYSPSFQG |
| G98A | QVQLVQSGAEVKKPGESLKISCKGSGYSFT | SYWIA | WVRQMPGKGLEYMG | LIYPGDSDTKYSPSFQG |
| ML3-9 | QVQLVQSGAEVKKPGESLKISCKGSGYSFT | SYWIA | WVRQMPGKGLEYMG | LIYPGDSDTKYSPSFQG |
| H3B1 | QVQLVQSGAEVKKPGESLKISCKGSGYSFT | SYWIA | WVRQMPGKGLEYMG | LIYPGDSDTKYSPSFQG |
| B1D2 | QVQLVQSGAEVKKPGESLKISCKGSGYSFT | SYWIA | WVRQMPGKGLEYMG | LIYPGDSDTKYSPSFQG |

| Framework 3 | CDR3 | Framework 4 |
|---|---|---|
| QVTISVDKSVSTAYLQWSSLKPSDSAVYFCAR | HDVGYCSSSNCAKWPEYFQH | WGQGTLVTVSS |
| QVTISVDKSVSTAYLQWSSLKPSDSAVYFCAR | HDVAYCSSSNCAKWPEYFQH | WGQGTLVTVSS |
| QVTISVDKSVSTAYLQWSSLKPSDSAVYFCAR | HDVGYCSSSNCAKWPEYFQH | WGQGTLVTVSS |
| QVTISVDKSVSTAYLQWSSLKPSDSAVYFCAR | HDVGYCTDRTCAKWPEYFQH | WGQGTLVTVSS |
| QVTISVDKSVSTAYLQWSSLKPSDSAVYFCAR | HDVGYCTDRTCAKWPEWLGV | WGQGTLVTVSS |

Light Chain:

| Clone | Framework 1 | CDR1 | Framework 2 | CDR2 |
|---|---|---|---|---|
| C6.5 | QSVLTQPPSVSAAPGQKVTISC | SGSSSNIGNNYVS | WYQQLPGTAPKLLIY | GHTNRPA |
| G98A | QSVLTQPPSVSAAPGQKVTISC | SGSSSNIGNNYVS | WYQQLPGTAPKLLIY | GHTNRPA |
| ML3-9 | QSVLTQPPSVSAAPGQKVTISC | SGSSSNIGNNYVS | WYQQLPGTAPKLLIY | DHTNRPA |
| H3B1 | QSVLTQPPSVSAAPGQKVTISC | SGSSSNIGNNYVS | WYQQLPGTAPKLLIY | DHTNRPA |
| B1D2 | QSVLTQPPSVSAAPGQKVTISC | SGSSSNIGNNYVS | WYQQLPGTAPKLLIY | DHTNRPA |

| Framework 3 | CDR3 | Framework 4 |
|---|---|---|
| GVPDRFSGSKSGTSASLAISGFRSEDEADYYC | AAWDDSLSGWV | FGGGTKLTVLG |
| GVPDRFSGSKSGTSASLAISGFRSEDEADYYC | ASWDYTLSGWV | FGGGTKLTVLG |
| GVPDRFSGSKSGTSASLAISGFRSEDEADYYC | ASWDYTLSGWV | FGGGTKLTVLG |
| GVPDRFSGSKSGTSASLAISGFRSEDEADYYC | ASWDYTLSGWV | FGGGTKVTVLG |
| GVPDRFSGSKSGTSASLAISGFRSEDEADYYC | ASWDYTLSGWV | FGGGTKVTVLG |

*Fig. 13*

Heavy Chain:

| Clone Name | Framework 1 | CDR1 | Framework 2 | CDR2 |
|---|---|---|---|---|
| C6.5 | QVQLLQSGAELKKPGESLKISCKGSGYSFT | SYWIA | WVRQMPGKGLEYMG | LIYPGDSDTKYSPSFQG |
| G98A | QVQLLQSGAEVKKPGESLKISCKGSGYSFT | SYWIA | WVRQMPGKGLEYMG | LIYPGDSDTKYSPSFQG |
| ML3-9 | QVQLLQSGAEVKKPGESLKISCKGSGYSFT | SYWIA | WVRQMPGKGLEYMG | LIYPGDSDTKYSPSFQG |
| H3B1 | QVQLLQSGAEVKKPGESLKISCKGSGYSFT | SYWIA | WVRQMPGKGLEYMG | LIYPGDSDTKYSPSFQG |
| B1D2 | QVQLLQSGAEVKKPGESLKISCKGSGYSFT | SYWIA | WVRQMPGKGLEYMG | LIYPGDSDTKYSPSFQG |

| Framework 3 | CDR3 | Framework 4 |
|---|---|---|
| QVTISVDKSVSTAYLQWSSLKPSDSAVYFCAR | HDVGYCSSSNCAKWPEYFQH | WGQGTLVTVSS |
| QVTISVDKSVSTAYLQWSSLKPSDSAVYFCAR | HDVAYCSSSNCAKWPEYFQH | WGQGTLVTVSS |
| QVTISVDKSVSTAYLQWSSLKPSDSAVYFCAR | HDVGYCSSSNCAKWPEYFQH | WGQGTLVTVSS |
| QVTISVDKSVSTAYLQWSSLKPSDSAVYFCAR | HDVGYCTDRTCAKWPEYFQH | WGQGTLVTVSS |
| QVTISVDKSVSTAYLQWSSLKPSDSAVYFCAR | HDVGYCTDRTCAKWPEWLGV | WGQGTLVTVSS |

Light Chain:

| Clone Name | Framework 1 | CDR1 | Framework 2 | CDR2 |
|---|---|---|---|---|
| C6.5 | QSVLTQPPSVSAAPGQKVTISC | SGSSSNIGNNYVS | WYQQLPGTAPKLLIY | GHTNRPA |
| G98A | ESVLTQPPSVSAAPGQKVTISC | SGSSSNIGNNYVS | WYQQLPGTAPKLLIY | DHTNRPA |
| ML3-9 | ESVLTQPPSVSAAPGQKVTISC | SGSSSNIGNNYVS | WYQQLPGTAPKLLIY | DHTNRPA |
| H3B1 | ESVLTQPPSVSAAPGQKVTISC | SGSSSNIGNNYVS | WYQQLPGTAPKLLIY | DHTNRPA |
| B1D2 | ESVLTQPPSVSAAPGQKVTISC | SGSSSNIGNNYVS | WYQQLPGTAPKLLIY | DHTNRPA |

| Framework 3 | CDR3 | Framework 4 |
|---|---|---|
| GVPDRFSGSKSGTSASLAISGFRSEDEADYYC | AAWDDSLSGWV | FGGGTKLTVLG |
| GVPDRFSGSKSGTSASLAISGFRSEDEADYYC | ASWDYTLSGWV | FGGGTKLTVLG |
| GVPDRFSGSKSGTSASLAISGFRSEDEADYYC | ASWDYTLSGWV | FGGGTKLTVLG |
| GVPDRFSGSKSGTSASLAISGFRSEDEADYYC | ASWDYTLSGWV | FGGGTKLTVLG |
| GVPDRFSGSKSGTSASLAISGFRSEDEADYYC | ASWDYTLSGWV | FGGGTKLTVLG |

*Fig. 14*

BISPECIFIC SINGLE CHAIN FV ANTIBODY MOLECULES AND METHODS OF USE THEREOF

CROSS-REFERENCE TO RELATED APPLICATIONS

This application is a Divisional of U.S. Ser. No. 11/154,103, filed on Jun. 15, 2005, which is a continuation-in-part of U.S. Ser. No. 10/406,830, filed on Apr. 4, 2003 which claims priority and benefit of U.S. Provisional Application U.S. Ser. No. 60/370,276, filed on Apr. 5, 2002, all of which are incorporated herein by reference in their entirety for all purposes.

STATEMENT AS TO RIGHTS TO INVENTIONS MADE UNDER FEDERALLY SPONSORED RESEARCH AND DEVELOPMENT

This work was supported in part by a Grant from the United States Army Medical Research and Material Command Breast Cancer Research Program, Grant No: DAMD 17-01-1-0520, and The United States National Cancer Institute, Institutional Pilot Grant No: NCI CA06927. The government of the United States of America may have certain rights in this invention.

FIELD OF THE INVENTION

The present invention relates to the fields of immunology and oncology, and more specifically, to bispecific antibody molecules (e.g. bs scFv) that can be used to advantage in the detection and/or treatment of various cancers that overexpress the Epidermal Growth Factor Receptor (EGFR) family of proteins. Certain illustrative bispecific scFv antibody molecules of the invention have binding specificities for either two distinct epitopes of a single member of the EGFR family or alternatively specificity for two distinct members of the EGFR family.

BACKGROUND OF THE INVENTION

The Epidermal Growth Factor Receptor (EGFR) signaling pathway plays an important role in the development and spread of cancer throughout the body. EGFR, also known as erb-b1, is a member of a family of four genes that also includes HER2/neu (erb-b2), HER3 (erb-b3) and HER4 (erb-b4). EGFR is expressed in a wide range of solid tumors, including colon cancers, head and neck cancers, pancreatic cancers, ovarian cancers, and breast cancers.

HER2/neu is a cell surface receptor protein with tyrosine kinase activity. The complete protein consists of three parts: an intracellular cytoplasmic domain, a short hydrophobic transmembrane segment and an extracellular domain (ECD) that is responsible for ligand binding. This receptor protein is expressed on the cell membrane of a variety of epithelial cell types and, through binding of specific growth factors, regulates various aspects of cell growth division.

Her2/neu, the gene that encodes for the HER2/neu protein, is a member of a group of genes known as proto-oncogenes. Proto-oncogenes encode important proteins, such as growth factors, growth factor receptors, and apoptotic proteins, that are involved in normal cell growth and differentiation. When proto-oncogenes are altered by point mutation, translocation or gene amplification, they produce growth signals that may lead to aberrant cellular transformation and the development of cancer.

While Her2/neu can be expressed at low levels in many normal cells, it is typically overexpressed in a variety of cancers. Overexpression of Her2/neu is caused in most cases by an increase in copy number of the gene (gene amplification) and/or by an increase in expression level of the Her2/neu genes in the cell. Overexpression of this growth factor receptor plays a key role in tumor progression by causing a higher rate of cell growth and oncogenic transformation. Gene amplification of the Her2/neu gene has been observed in a variety of cancer types, including, breast, ovarian, endometrial, gastric, pancreatic, prostate and salivary gland (Hynes and Stem (1994) *Biochim Biophys Acta.*, 1198: 165-184). In breast cancer patients, HER2/neu has also been shown to be of clinical importance as it is associated with poor prognosis, tumor recurrence and shortened survival in breast cancer patients (Seshadri et al. (1993) *J. Clin. Oncol.*, 11: 1936-1942; Berger et al. (1988) *Cancer Res.*, 48: 1238-1243; O'Reilly et al. (1991) *Br. J. Cancer*, 63: 444-446).

Currently, a great deal of attention has focused on the development of novel immunotherapy strategies for the treatment of cancer. One such strategy is antibody-based cancer therapy. A major goal of antibody-based cancer therapy is to specifically deliver toxic payloads such as radioisotopes, toxins or drugs to tumors. The size range of antibody binding site-based molecules includes: IgM (1000 kDa), IgG (150 kDa), F(ab')$_2$ (100 kDa), Fab (50 kDa), (scFv')$_2$ (55 kDa) and scFv (25 kDa). In immunodeficient mice, larger molecules such as IgG and F(ab')$_2$ fragments are retained at high levels in human tumor xenografts with a low degree of specificity (Adams et al. (1992) *Antibody, Immunoconj. Radiopharm.*, 5: 81-95; Milenic et al. (1991) *J. Cancer Res.* 51: 6363-6371), while smaller molecules such as scFv, (scFv')$_2$ and Fab are retained in tumors at comparatively lower levels with greatly improved specificity (Milenic et al. (1991) *J. Cancer Res.* 51: 6363-6371; Adams et al. (1993) *Cancer Res.* 53: 4026-4034; Beaumier et al. (1985) *J. Nucl. Med.* 26: 1172-1179; Colcher et al. (1990) *J. Natl. Cancer Inst.* 82: 1191-1197).

The most prominent determinant of the above targeting properties is the size of the antibody-based molecule relative to the renal threshold for first pass clearance. Another important feature of antibody-based molecules is valence, as significantly greater tumor retention has been associated with multivalent binding to target antigen (Milenic et al. (1991) *J. Cancer Res.* 51: 6363-6371; Adams et al. (1993) *Cancer Res.* 53: 4026-4034; Adams et al. (1996) *Proc. Amer. Assoc. Cancer Res.* 37: 472; Wolf et al. (1993) *Cancer Res.* 53: 2560-2565).

Herceptin, a new form of immunotherapy targeting breast cancer, was recently developed to target cancer cells that overexpress Her2/neu. This treatment has been shown in clinical trials to provide effective treatment for patients with HER2/neu positive metastatic breast cancer. However, this drug treatment is costly and is associated with significant morbidity and mortality.

Several other types of therapy have been shown to be more or less effective in breast cancer patients whose tumors express elevated levels of Her2/neu. These include, anthracycline therapy which is thought to be more effective in patients with amplified Her2/neu expression, and hormonal therapy which is less effective in patients whose level of Her2/neu expression is high.

Attention has also focused upon the generation of bivalent single chain Fv-based antibody molecules with molecular weights in the range of the renal threshold for first pass clearance. These include 50 kDa diabodies (Holliger et al. (1993) *Proc. Natl. Acad. Sci. USA*, 90: 6444-6448), 55 kDa (scFv')$_2$ (Adams et al. (1993) *Cancer Res.* 53: 4026-4034), 60-65 kDa amphipathic helix-based scFv dimers (Pack et al. (1993) *Bio/Technology* 11: 1271-1277; Pack (1992) *Biochemistry* 31: 1579-1584), and 80 kDa (scFv-C$_H$3)$_2$ LD minibodies and Flex minibodies (Hu et al. (1996) *Cancer Res.* 56: 3055-3061). While each of these proteins is capable of binding two antigen molecules, they differ in the orientation, flexibility and the span of their binding sites. It is believed that these new and innovative immunotherapies will help improve outcomes in breast and other cancers which too frequently recur or progress despite aggressive multi-modality therapy.

SUMMARY OF THE INVENTION

This invention pertains to the identification of bispecific (or polyspecific) antibody molecules (e.g. bs scFv) that can be used to advantage in the detection and/or treatment of various cancers that overexpress the Epidermal Growth Factor Receptor (EGFR) family of proteins. Thus, in one embodiment this invention provides a bispecific antibody comprising an first antibody and a second antibody joined (directly or through a linker) to each other where the first antibody and the second antibody bind specifically to different epitopes and the first antibody has binding specificity for (specifically binds) at least one epitope on a member of the Epidermal Growth Factor Receptor protein family, (e.g., EGFR, HER2/neu, HER3, HER4), and the second antibody has binding specificity for (specifically binds) a second epitope on a member of the Epidermal Growth Factor Receptor protein family which is different from the first epitope is an epitope on a protein selected from the group consisting of EGFR, HER2/neu, HER3 and HER4. In certain embodiments, the antibodies are joined by a linker, more preferably by a peptide linker, and most preferably by a peptide linker that lacks a proteolytic cleavage site (e.g., a linker having the amino acid sequence of SEQ ID NO:37). In certain embodiments, the first and/or the second antibody specifically binds an epitope specifically bound by an antibody selected from the group consisting of C6.5, C6ML3-9, C6MH3-B1, C6-B1D2, F5, HER3.A5, HER3.F4, HER3.H1, HER3.H3, HER3.E12, HER3.B12, EGFR.E12, EGFR.C10, EGFR.B11, EGFR.E8, HER4.B4, HER4.G4, HER4.F4, HER4.A8, HER4.B6, HER4.D4, HER4.D7, HER4.D11, HER4.D12, HER4.E3, HER4.E7, HER4.F8 and HER4.C7. In certain embodiments, the first and/or the second antibody comprise one, two, or all complementarity determining region(s) of an antibody selected from the group consisting of C6.5, C6ML3-9, C6MH3-B1, C6-B1D2, F5, HER3.A5, HER3.F4, HER3.H1, HER3.H3, HER3.E12, HER3.B12, EGFR.E12, EGFR.C10, EGFR.B11, EGFR.E8, HER4.B4, HER4.G4, HER4.F4, HER4.A8, HER4.B6, HER4.D4, HER4.D7, HER4.D11, HER4.D12, HER4.E3, HER4.E7, HER4.F8 and HER4.C7. In certain embodiments, the bispecific antibody or polyspecific antibody is encoded by a vector comprising a nucleic acid that encodes a polypeptide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 14, SEQ ID NO:20, and SEQ ID NO:22. In certain embodiments, the bispecific or polyspecific antibody is encoded by a vector comprising two nucleic acid sequences encoding polypeptides encoded by two nucleic acid sequences as described herein, e.g., independently selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO:20, and SEQ ID NO:22. In certain instances, the bispecific antibody is encoded by a vector comprising, in certain instances, at least one, and in certain instances at least two nucleic acid nucleic acid sequence as described herein, e.g., selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 14, SEQ ID NO:20, and SEQ ID NO:22. In certain instances the vector further comprises a nucleic acid sequence encoding a polypeptide having the sequence of SEQ ID NO:37.

In certain embodiments, the first and/or second antibodies (e.g. the antibodies described above) are single-chain antibodies (e.g. sc Fv antibodies). Where both the first and second antibodies are both single chain antibodies, the antibodies are preferably directly attached (to form a single polypeptide) or attached through a linker, more preferably through a peptide linker (e.g. a peptide linker lacking a proteolytic cleavage site) to form a single chain bispecific or polyspecific antibody (e.g. bs-scFv). bispecific (or polyspecific) antibody is a single chain antibody and said second antibody is a single chain antibody and said first antibody is coupled to said second antibody by a peptide linker.

In another embodiment, this invention includes a composition comprising a bispecific or polyspecific antibody as disclosed and/or claimed herein and a pharmaceutically acceptable carrier.

This invention also provides a method for treating cancer (e.g. mitigating one or more symptoms of cancer). The method typically involves administering to a patient (human or non-human animal) in need thereof a therapeutically effective amount of a bispecific or polyspecific antibody as disclosed and/or claimed herein and a pharmaceutically acceptable carrier. The cancer can include, but is not limited to a cancer is selected from the group consisting of breast, colon, ovarian, endometrial, gastric, pancreatic, prostate and salivary gland cancer. The administration can be by any of a variety of convenient methods including systemic injectable administration, injection into a tumor or cancerous tissue, oral administration, and the like.

In still another embodiment, this invention provides a method for treating cancer (e.g. mitigating one or more symptoms of cancer). The method typically involves administering to a patient (human or non-human animal) in need thereof a therapeutically effective amount of a bispecific or polyspecific antibody as disclosed and/or claimed herein and a pharmaceutically acceptable carrier, in combination with an other cytotoxic agent selected from the group consisting of a chemotherapeutic agent, external beam radiation, a targeted radioisotope, and a signal transduction inhibitor. The cancer can include, but is not limited to a cancer is selected from the group consisting of breast, colon, ovarian, endometrial, gastric, pancreatic, prostate and salivary gland cancer. The administration can be by any of a variety of convenient methods including systemic injectable administration, injection into a tumor or cancerous tissue, oral administration, and the like.

In yet another embodiment, this invention provides a chimeric moiety comprising of a bispecific or polyspecific antibody as disclosed and/or claimed herein coupled to an effector. Preferred effectors include, but are not limited to a cytotoxin, a label, a radionuclide, a drug, a liposome, a ligand, and an antibody. In certain instances, where the effector is a polypeptide, the chimeric moiety is a fusion protein, preferably a recombinantly expressed fusion protein.

This invention also provides a method of specifically delivering or targeting an effector molecule to a cell bearing a receptor from Epidermal Growth Factor Receptor protein family (e.g., EGFR, HER2/neu, HER3 HER4). The method involves providing a chimeric moiety as described and/or claimed herein, and contacting the cell with the chimeric moiety, whereby the chimeric moiety specifically binds to the cell. Preferred effectors include, but are not limited to a cytotoxin, a label, a radionuclide, a drug, a liposome, a ligand, an antibody, etc. In certain embodiments, the chimeric moiety is a fusion protein. In certain embodiments, the cell is a cancer cell, preferably a cancer cell that overexpress one or more members of the EGFR protein family. Particularly preferred cancer cells include, but are not limited to breast, colon, ovarian, endometrial, gastric, pancreatic, prostate and salivary gland cancer cells.

Also provided is a method of specifically killing and/or inhibiting the growth or proliferation of a cell bearing a receptor from Epidermal Growth Factor Receptor protein family (e.g. EGFR, HER2/neu, HER3, HER4). The method typically involves providing a chimeric moiety as described and/or claimed herein attached to a cytoxic or cytostatic effector (e.g. an a cytotoxin, a radioactive moiety, and a liposome comprising a cytotoxic or cytostatic agent, and the like); and contacting said cell with the chimeric moiety, whereby the chimeric moiety specifically binds to the cell resulting in the death and/or inhibition of growth and/or proliferation of the cell. In certain embodiments, the chimeric moiety is a fusion protein. In certain embodiments, the cell is a cancer cell, preferably a cancer cell that overexpress one or more members of the EGFR protein family. Particularly preferred cancer cells include, but are not limited to breast, colon, ovarian, endometrial, gastric, pancreatic, prostate and salivary gland cancer cells.

This invention also provides methods of detecting and/or visualizing and/or diagnosing the presence of a cancer cell or tissue. The method typically involves contacting a cell or tissue with a chimeric moiety comprising a bispecific or polyspecific antibody as described herein attached to a detectable label; and detecting the label where detection of the label in association with the cell or tissue indicates the presence of a cell or tissue expressing (or overexpressing one or more members of the Epidermal Growth Factor Receptor protein family. Preferred detectable labels include, but are not limited to a gamma emitter, a positron emitter, an MRI label, and a fluorescent or calorimetric label. In certain instances, the detectable label is a gamma emitter and the detecting comprises imaging with a gamma camera. In certain instances, the detectable label is a positron emitter and the detecting comprises imaging with positron emission tomography (PET). In certain instances, the detectable label is an MRI label and the detecting comprises detecting with magnetic resonance imaging. In certain embodiments, the cell or tissue expressing one or more members of the Epidermal Growth Factor Receptor Protein family is a cell or tissue that overexpresses a protein selected from the group consisting of EGFR, HER2/neu, HER3 and HER4. The cell or tissue expressing one or more members of the Epidermal Growth Factor Receptor Protein family is a can be a cancer cell or tissue (e.g., breast, colon, ovarian, endometrial, gastric, pancreatic, prostate, or salivary gland cancer). It is noted that the diagnostic assay can be a component of a differential diagnosis of a cancer and/or can be used to type a cancer as one that overexpresses one or members of the EGFR protein family and/or the assay can be used to visualize a known cancer. In these (and other) instances, the assay need not be dispositive of the presence of a cancer cell, but simply indicative of the likely presence of such a cell or tissue. In certain embodiments, the detecting comprises a non-invasive imaging technique. In certain embodiments, the detecting comprises immunohistochemistry. In certain embodiments, the detecting comprises detecting in a tissue sample or biopsy. In certain embodiments, the detecting comprises detecting in a tissue section. In certain embodiments, the detecting is in vivo detection.

In accordance with the present invention, in certain embodiments, novel bispecific single chain Fv antibody molecules (bs-scFv) having binding affinity for members of the EGFR protein family are provided.

In certain preferred embodiments of the invention, the bs-scFv antibodies have a first and second arm that have binding affinity for two distinct epitopes on different members of the EGFR protein family (e.g., EGFR, HER2/neu, HER3 and HER4) or for two distinct epitopes on a single member of the EGFR protein family, and are operably linked via a novel linker molecule which lacks proteolytic cleavage sites. This linker constitutes an aspect of the present invention. The arms that are paired together to form the bs-scFv antibodies may be any one of the following arms including C6.5, C6ML3-9, C6MH3-B1, C6-B1D2, F5, HER3.A5, HER3.F4, HER3.H1, HER3.H3, HER3.E12, HER3.B12, EGFR.E12, EGFR.C10, EGFR.B11, EGFR.E8, HER4.B4, HER4.G4, HER4.F4, HER4.A8, HER4.B6, HER4.D4, HER4.D7, HER4.D1, HER4.D12, HER4.E3, HER4.E7, HER4.F8 and HER4.C7. In a particularly preferred embodiment, the arms are linked together with a linker molecule having the amino acid sequence of SEQ ID NO: 11. Vectors and transformants comprising the nucleic acid sequences encoding the scFv arms and the linker molecule are also provided.

An exemplary bs-scFv antibody that has binding affinity for two members of the EGFR protein family is ALM which has one arm that has binding specificity for HER3 and a second arm that has binding specificity for HER2/neu. An exemplary bs-scFv antibody that has binding affinity for two epitopes on a single member of the EGFR protein family is ALF, which has one arm with binding specificity for an epitope on HER3 and a second arm with binding specificity for a different epitope on HER3.

In another embodiment of the invention, the bs-scFv antibodies have binding affinity for members of the EGFR protein family that are overexpressed by tumor cells.

In yet another embodiment of the invention, compositions and methods for treating cancer are provided wherein a patient is administered a therapeutically effective amount of a bs-scFv antibody molecule of the invention in a pharmaceutically acceptable carrier, either alone or in combination with other cytotoxic agents, such as, chemotherapeutic agents, external beam radiation, targeted radioisotopes and signal transduction inhibitors.

DEFINITIONS

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide. Preferred "peptides", "polypeptides", and "proteins" are chains of amino acids whose α carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to peptide mimetics such as amino acids joined by an ether as opposed to an amide bond.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region thereby converting the (Fab')$_2$ dimer into a Fab' monomer. The Fab' monomer is essentially a Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes whole antibodies, antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (scFv) in which a variable heavy and a variable light chain are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker. Huston, et al. (1988) *Proc. Nat. Acad. Sci. USA*, 85: 5879-5883. While the $V_H$ and $V_L$ are connected to each as a single polypeptide chain, the $V_H$ and $V_L$ domains associate non-covalently. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to, e.g., g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). Particularly preferred antibodies should include all that have been displayed on phage (e.g., scFv, Fv, Fab and disulfide linked Fv (Reiter et al. (1995) *Protein Eng.* 8: 1323-1331), and also include bispecific, trispecific, quadraspecific, and generally polyspecific antibodies (e.g. bs scFv).

With respect to antibodies of the invention, the term "immunologically specific" "specifically binds" refers to antibodies that bind to one or more epitopes of a protein of interest (e.g., HER2/neu), but which do not substantially recognize and bind other molecules in a sample containing a mixed population of antigenic biological molecules.

The term "bispecific antibody" as used herein refers to an antibody comprising two antigen-binding sites, a first binding site having affinity for a first antigen or epitope and a second binding site having binding affinity for a second antigen or epitope distinct from the first.

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10):1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 1419), phosphorothioate (Mag et al. (1991) *Nucleic Acids Res.* 19:1437; and U.S. Pat. No. 5,644, 048), phosphorodithioate (Briu et al. (1989) *J. Am. Chem. Soc.* 111:2321, O-methylphosphoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature,* 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469, 863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235, 033 and 5,034,506, and Chapters 6 and 7, ASC Symposium Series 580, *Carbohydrate Modifications in Antisense Research*, Ed. Y. S. Sanghui and P. Dan Cook. Nucleic acids containing one or more carbocyclic sugars are also included within the definition of nucleic acids (see Jenkins et al. (1995), *Chem. Soc. Rev.* pp 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions. The term "stringent conditions" refers to conditions under which a probe will hybridize preferentially to its target subsequence, and to a lesser extent to, or not at all to, other sequences. Stringent hybridization and stringent hybridization wash conditions in the context of nucleic acid hybridization are sequence dependent, and are different under different environmental parameters. An extensive guide to the hybridization of nucleic acids is found in, e.g., Tijssen (1993) *Laboratory Techniques in Biochemistry and Molecular Biology—Hybridization with Nucleic Acid Probes part I, chapt 2, Overview of principles of hybridization and the strategy of nucleic acid probe assays*, Elsevier, N.Y. (Tijssen). Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on an array or on a filter in a Southern or northern blot is 42° C. using standard hybridization solutions (see, e.g., Sambrook (1989) *Molecular Cloning: A Laboratory Manual* (2nd ed.) Vol. 1-3, Cold Spring Harbor Laboratory, Cold Spring Harbor Press, NY, and detailed discussion, below), with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, e.g., Sambrook supra.) for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example of a low stringency wash for a duplex of, e.g., more than 100 nucleotides, is 4× to 6×SSC at 40° C. for 15 minutes.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

A "replicon" is any genetic element, for example, a plasmid, cosmid, bacmid, plastid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as appropriate temperature and pH, the primer can be extended at its 3' terminus by the addition of nucleotides by the action of a polymerase or similar activity to yield a primer extension product. The primer can vary in length depending on the particular conditions and requirement of the application. Often primers range from about 15 to about 25 or more nucleotides in length. The primer are typically of sufficient complementarity to the desired template to prime the synthesis of the desired extension product. In other words, the primers are able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases can be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by calorimetric, fluorogenic, chemiluminescent or other methods. The nucleic acid can be either RNA or DNA, linear or circular, single or double stranded, antisense or sense polarity, and is operatively linked to the necessary control elements for the expression of the reporter gene product. The control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion and the like. The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell or plant.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. With respect to the peptides of this invention sequence identity is determined over the full length of the peptide.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman (1988) *Proc. Natl. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendrogram showing the clustering relationships used to create the alignment. PILEUP uses a simplification of the progressive alignment method of Feng & Doolittle (1987) *J. Mol. Evol.* 35:351-360. The method used is similar to the method described by Higgins & Sharp (1989) *CABIOS* 5: 151-153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al. (1990) *J. Mol. Biol.* 215: 403-410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul (1993) *Proc. Natl. Acad. Sci. USA,* 90: 5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

The phrase "specifically target/deliver" when used, for example with reference to a chimeric moiety of this invention refers to specific binding of the moiety to a target (e.g. a cell overexpressing the target protein(s)) this results in an increase in local duration and/or concentration of the moiety at or within the cell as compared to that which would be obtained without "specific" targeting. The specificity need not be absolute, but simply detectably greater/measurably avidity/affinity than that observed for a cell expressing the target protein(s) at normal (e.g., wildtype) or than that observed for a cell that does not express the target protein(s).

Amino acid residues are identified in the present application according to standard 3-letter or 1-letter abbreviations (e.g. as set forth in WIPO standard ST 25) and/or as set forth in Table 1.

TABLE 1

Amino acid abbreviations.

| Amino Acid | 3 Letter Abbreviation | 1 Letter Abbreviation |
|---|---|---|
| L-Alanine | Ala | A |
| L-Arginine | Arg | R |
| L-Asparagine | Asn | N |
| L-AsparticAcid | Asp | D |
| L-Cysteine | Cys | C |
| L-Glutamine | Gln | Q |
| L-GlutamicAcid | Glu | E |
| Glycine | Gly | G |
| L-Histidine | His | H |
| L-Isoleucine | Ile | I |
| L-Leucine | Leu | L |
| L-Methionine | Met | M |
| L-Phenylalanine | Phe | F |
| L-Proline | Pro | P |
| L-Serine | Ser | S |
| L-Threonine | Thr | T |
| L-Tryptophan | Trp | W |
| L-Tyrosine | Tyr | Y |
| L-Valine | Val | V |
| L-Lysine | Lys | K |

Enantiomeric amino acids described herein are preferred to be in the "L" isomeric form. However, residues in the "D" isomeric form can be substituted for any L-amino acid residue, provided the desired properties of the polypeptide are retained. All amino-acid residue sequences represented herein conform to the conventional left-to-right amino-terminus to carboxy-terminus orientation.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like).

The term "functional" as used herein implies that the nucleic or amino acid sequence is functional for the recited assay or purpose.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the basic and novel characteristics of the sequence.

The term "tag," "tag sequence" or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, of that sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitates isolation or detection by interaction with avidin reagents, and the like. Numerous other tag moieties are known to, and can be envisioned by the trained artisan, and are contemplated to be within the scope of this definition.

A "clone" or "clonal cell population" is a population of cells derived from a single cell or common ancestor, e.g., by mitosis.

A "cell line" is a clone of a primary cell or cell population that is capable of stable growth in vitro for many generations.

BRIEF DESCRIPTION OF THE DRAWINGS

FIG. 13 shows the sequences of ScFv light and heavy chains as determined by the Adams Lab and used in the construction of certain bs-scFv molecules. Sequences are given for C6.5 heavy chain (SEQ ID NO:38), G98A heavy chain (SEQ ID NO:39), ML3-9 heavy chain (SEQ ID NO:40), H3B1 heavy chain (SEQ ID NO:41), B1D2 heavy chain (SEQ ID NO:42), C6.5 light chain (SEQ ID NO:43), G98A light chain (SEQ ID NO:44), ML3-9 light chain (SEQ ID NO:45), H3B1 light chain (SEQ ID NO:46), and B1D2 light chain (SEQ ID NO:47).

FIG. 14 shows deduced protein sequences of heavy and light chain variable regions of all IgG produced in IDEC vector provided by the Marks lab. In certain embodiments the sequence of scFvs can differ from this. Sequences are given for C6.5 heavy chain (SEQ ID NO:48), G98A heavy chain (SEQ ID NO:49), ML3-9 heavy chain (SEQ ID NO:50), H3B1 heavy chain (SEQ ID NO:51), B1D2 heavy chain (SEQ ID NO:52), C6.5 light chain (SEQ ID NO:53), G98A light chain (SEQ ID NO:54), ML3-9 light chain (SEQ ID NO:55), H3B1 light chain (SEQ ID NO:56), and B1D2 light chain (SEQ ID NO:57).

DETAILED DESCRIPTION

Figure 1:
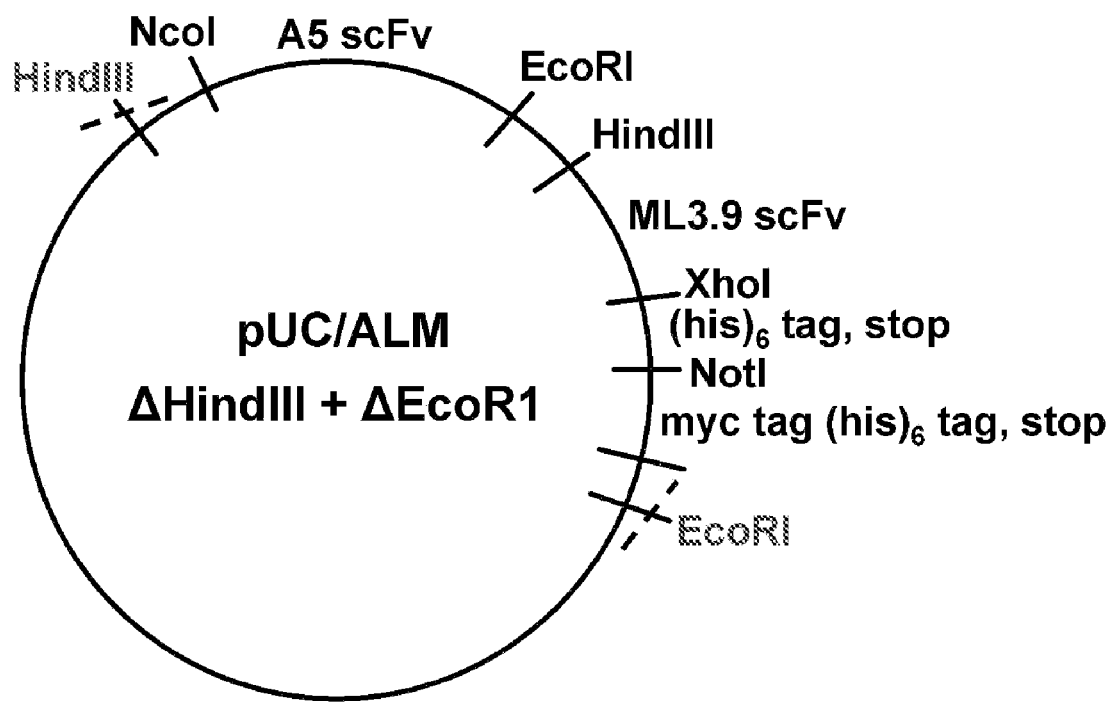
FIG. 1 shows a schematic diagram of the pUC/ALM vector.

Tumors often overexpress growth factor receptors that bind various ligands ligand and facilitate unrestricted tumor growth. One example of such growth factor receptors is the Epidermal Growth Factor Receptor (EGFR) protein family.

Signal transduction through members of the Epidermal Growth Factor Receptor (EGFR) protein family is dependent upon the formation of homodimers or heterodimers triggered by the binding of ligand. This receptor family is comprised of four membrane-bound proteins: EGFR, HER2/neu, HER3 and HER4. Overexpression of these proteins has been correlated with a poor prognosis in a number of types of cancer, including, but not limited to, breast, colon, ovarian, endometrial, gastric, pancreatic, prostate and salivary gland cancers. While a number of groups have developed strategies to target individual members of the EGFR protein family (e.g., HER2/neu or EGFR) to inhibit tumor growth, none of the treatments has been proven to ultimately cure these forms of cancer.

In accordance with the present invention, novel antibody constructs have been developed that are capable of simultaneously targeting multiple members multiple members (or multiple sites on a given member) of the EGFR protein family. The antibody constructs typically comprise a first antibody and a second antibody joined to each other where the first antibody and the second antibody bind specifically to different epitopes on the same or different members of the EGFR protein family. In certain embodiments, the bispecific antibody constructs are bispecific single chain molecules (e.g., bispecific single chain Fv (bs-scFv)), but the constructs need not be so limited. Thus, for example, chemically conjugated whole antibodies, or antibody fragments are also contemplated within the scope of this invention. In general, where bi-specific antibodies are described herein, it will be appreciated that trispecfic, or more generally polyspecific antibodies are also contemplated.

The bispecific antibodies of this invention bind to selected members of the EGFR protein family (e.g., EGFR, HER2/neu, HER3, HER4) to prevent ligand induced signaling and/or to trigger cytostatic and/or cytotoxic effects. The bispecific antibodies can also be used to specifically label cancer cells, solid tumors, and the like, and, more generally, to specifically target/deliver any conjugated or otherwise coupled effector (e.g. radioisotope, label, cytotoxin, drug, liposome, antibody, nucleic acid, dendrimer, etc.) to cancer cells including but not limited to isolated cancer cells, metastatic cells, solid tumor cells, and the like.

In certain preferred embodiments, the bispecific antibodies of this invention are bispecific single chain Fv antibodies (bs-scFv). Single chain Fv antibody fragments are engineered antibody derivatives that include both a heavy and a light chain variable region joined by a peptide linker molecule and are potentially more effective than unmodified IgG antibodies because their reduced size permits them to penetrate tissues and solid tumors more readily than IgG antibodies.

In one embodiment the bispecific antibodies of this invention (e.g. the bs-scFv antibody molecules) comprise two domains that provide two distinct binding specificities. A first domain has binding specificity for an epitope on one member of the EGFR protein family and the second domain has binding specificity for an epitope on a second member of the EGFR protein family. An exemplary bs-scFv molecule of the invention is "ALM"; a bispecific antibody that was created with one arm (domain) that exhibits binding specificity to an epitope on HER2/neu and a second arm (domain) that exhibits binding specificity to an epitope on HER3.

Alternatively, the bispecific antibodies of the invention can be generated such that one domain has binding specificity for one epitope on a member of the EGFR protein family and a second domain has binding specificity for a second distinct epitope on the same member of the EGFR protein family. An exemplary bs-scFv of this type is "ALF" which is composed of two distinct scFV molecules, both with a specificity for HER3.

I. Antibodies Forming the Bispecific or Polyspecific Antibodies of this Invention.

As indicated above, the bispecific or polyspecific antibodies of this invention typically comprise two or more binding domains at least two of which are specific to different epitopes of the EGFR protein family. Preferred antibodies of this invention comprise domains specific to epitopes of EGFR, HER2/neu, HER3 and HER4.

Using phage display approaches, a number of single chain antibodies have been raised that are specific to various epitopes on these members of the EGFR protein family. These single chain Fv antibodies can be used as domains/arms to construct a bispecific or polyspecific antibody according to this invention. A number of these antibodies are provided, below, in Table 2 and in FIGS. 13 and 14. Each arm (antibody) can be paired with a different arm to form either a bs-scFv antibody with binding specificity for two distinct epitopes on different members of the EGFR protein family or a bs-scFv antibody with binding specificity for two distinct epitopes on the same member of the EGFR protein family.

TABLE 2

Single-chain Fv antibodies directed against
epitopes of the EGFR protein family.

Anti-HER2/neu*:

C6.5***
C6ML3-9 (ML3.9 or C6ML3.9)
C6MH3-B1 (B1 or C6MH3.B1)
C6-B1D2 (B1D2 or C6MH3-B1D2)
F5 (SEQ ID NO: 1 protein, SEQ ID NO: 27 DNA)**
HER3.B12 (SEQ ID NO: 6 protein, SEQ ID NO: 32 DNA)
Anti-EGFR**:

EGFR.E12 (SEQ ID NO: 7 protein, SEQ ID NO: 33 DNA)
EGFR.C10 (SEQ ID NO: 8 protein, SEQ ID NO: 34 DNA)
EGFR.B11 (SEQ ID NO: 9 protein, SEQ ID NO: 35 DNA)
EGFR.E8 (SEQ ID NO: 10 protein, SEQ ID NO: 36 DNA)
Anti-HER3**:

HER3.A5
HER3.F4 (SEQ ID NO: 2 protein, SEQ ID NO: 28 DNA)
HER3.H1 (SEQ ID NO: 3 protein, SEQ ID NO: 29 DNA)
HER3.H3 (SEQ ID NO: 4 protein, SEQ ID NO: 30 DNA))
HER3.E12 (SEQ ID NO: 5 protein, SEQ ID NO: 31 DNA))
Anti-HER4:

HER4.B4
HER4.G4
HER4.F4
HER4.A8
HER4.B6 (SEQ ID NO: 19 protein, SEQ ID NO: 37 DNA)
HER4.D4
HER4.D7
HER4.D11
HER4.D12
HER4.E3 (SEQ ID NO: 21 protein, SEQ ID NO: 38 DNA)
HER4.E7
HER4.F8
HER4.C7

*Sequences are disclosed in Schier et al. (1996). J. Mol. Biol., 255(1): 28-43. See also Schier et al. (1995) Immunotechnology, 1: 73-81.
**Sequences are provided in Appendix A herein below;
***Sequences are also shown in FIGS. 13 and 14.

The bispecific or polyspecific antibodies of this invention, however need not be limited to the use of the particular antibodies enumerated in Table 2 and/or FIG. 13 or 14. In effect, each of the antibodies listed in Table 2 and/or FIG. 13 or 14 identifies an epitope of a member of the EGFR protein family and these antibodies can readily be used to identify other antibodies that bind to the same epitopes. Thus, in certain embodiments, the bispecific or polyspecific antibodies of this invention comprise one or more domains that specifically bind an epitope specifically bound by an antibody of Table 2 and/or FIG. 13 or 14 (e.g., an antibody selected from the group consisting of C6.5, C6ML3-9, C6MH3-B1, C6-B1D2, F5, HER3.A5, HER3.F4, HER3.H1, HER3.H3, HER3.E12, HER3.B12, EGFR.E12, EGFR.C10, EGFR.B11, EGFR.E8, HER4.B4, HER4.G4, HER4.F4, HER4.A8, HER4.B6, HER4.D4, HER4.D7, HER4.D11, HER4.D12, HER4.E3, HER4.E7, HER4.F8 and HER4.C7).

Such antibodies are readily identified by screening whole antibodies, antibody fragments, or single chain antibodies for their ability to compete with the antibodies listed in Table 2 for their ability to bind to a protein comprising the target epitope. In other words, candidate antibodies can be screened for cross-reactivity with the antibodies listed in Table 2 and/or FIG. 13 or 14 against the target protein in the EGFR protein family.

In a preferred embodiment, the antibodies of this invention specifically bind to one or more epitopes recognized by antibodies listed in Table 2 and/or FIG. 13 or 14. In other words, particularly preferred antibodies are cross-reactive with one of more of these antibodies. Means of assaying for cross-reactivity are well known to those of skill in the art (see, e.g., Dowbenko et al. (1988) J. Virol. 62: 4703-4711).

For example, in certain embodiments, cross-reactivity can be ascertained by providing an isolated EGFR family member (e.g., EGFR, HER2/neu, HER3 and HER4 or a fragment thereof) attached to a solid support and assaying the ability of a test antibody to compete with one or more of the antibodies listed in Table 2 for binding to the target protein. Thus, immunoassays in a competitive binding format are can be used for crossreactivity determinations. For example, in one embodiment, the EGFR family member polypeptide is immobilized to a solid support. Antibodies to be tested (e.g. generated by selection from a phage-display library, or generated in a whole antibody library) are added to the assay compete with one or more of the antibodies listed in Table 2 and/or FIG. 13 or 14 for binding to the immobilized polypeptide. The ability of test antibodies to compete with the binding of the antibodies of Table 2 and/or FIG. 13 or 14 to the immobilized protein are compared. The percent crossreactivity above proteins can then calculated, using standard calculations. If the test antibody competes with one or more of the Table 2 and/or FIG. 13 or 14 antibodies and has a binding affinity comparable to or greater than about $1 \times 10^{-8}$ M, more preferably greater than $1 \times 10^{-9}$, or $1 \times 10^{-10}$, or more generally with an affinity equal to or greater than the corresponding (competing) antibody, e.g., of Table 2 then the antibody is well suited for use in the present invention.

In a particularly preferred embodiment, cross-reactivity is performed by using surface plasmon resonance in a BIAcore. In a BIAcore flow cell, the EGFR protein is coupled to a sensor chip. With a typical flow rate of 5 (l/min, a titration of 100 nM to 1 (M antibody is injected over the flow cell surface for about 5 minutes to determine an antibody concentration that results in near saturation of the surface. Epitope mapping or cross-reactivity is then evaluated using pairs of antibodies at concentrations resulting in near saturation and at least 100 RU of antibody bound. The amount of antibody bound is determined for each member of a pair, and then the two antibodies are mixed together to give a final concentration equal to the concentration used for measurements of the individual antibodies. Antibodies recognizing different epitopes show an essentially additive increase in the RU bound when injected together, while antibodies recognizing identical epitopes show only a minimal increase in RU. In a particularly preferred embodiment, antibodies are said to be cross-reactive if, when "injected" together they show an essentially additive increase (preferably an increase by at least a factor of about 1.4, more preferably an increase by at least a factor of about 1.6, and most preferably an increase by at least a factor of about 1.8 or 2.

Cross-reactivity at the epitopes recognized by the antibodies listed in Table 2 and/or FIG. 13 or 14 can ascertained by a number of other standard techniques (see, e.g., Geysen et al (1987) J. Immunol. Meth. 102: 259-274).

In addition, number of the antibodies identified in Table 2 have been sequenced (see, e.g., FIGS. 13 and 14). The amino acid sequences comprising the complementarity determining regions (CDRs) are therefore known. Using this sequence information, the same or similar complementarity determining regions can be engineered into other antibodies to produce chimeric full size antibodies and/or antibody fragments, e.g. to ensure species compatibility, to increase serum half-life, and the like. A large number of methods of generating chimeric antibodies are well known to those of skill in the art (see, e.g., U.S. Pat. Nos. 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431, and 4,975,369).

In short, using routine methods, the antibodies listed in Table 2 can readily be used to generate or identify other antibodies (full length, antibody fragments, single-chain, and the like) that bind to the same epitope. Similarly, the antibodies listed in Table 2 can readily be utilized to generate other antibodies that have the same or similar complementarity determining regions (CDRs).

II. Preparation of Bi-Specific Antibody Molecules:

The antibodies directed to epitopes found on members of the EGFR protein family (e.g. the antibodies listed in Table 2) can be used to prepare bispecific or polyspecific antibodies of this invention. The two (or more) antibodies can be prepared using a variety of methods. For example, the antibodies can be prepared separately (e.g. using chemical protein synthesis, recombinant expression methods, hybridoma technology, etc.) and then chemically attached to each other, either directly or through a linker. Where both antibodies are single chain antibodies either directly joined at the termini or through a peptide linker, the bispecific or polyspecific molecule can be chemically synthesized, or more preferably is recombinantly expressed.

Means of chemically conjugating molecules are well known to those of skill in the art. The procedures for chemically coupling two antibodies are straightforward. Polypeptides typically contain variety of functional groups; e.g., carboxylic acid (COOH) or free amine (—$NH_2$) groups, that are available for reaction with a suitable functional groups on the corresponding antibody or on a linker.

Alternatively, the antibodies can be derivatized to expose or attach additional reactive functional groups. The derivatization can involve attachment of any of a number of linker molecules such as those available from Pierce Chemical Company, Rockford Ill. A variety of suitable linkers are known to those of skill in the art (see, e.g., European Patent Application No. 188,256; U.S. Pat. Nos. 4,671,958, 4,659, 839, 4,414,148, 4,699,784; 4,680,338; 4,569,789; and 4,589, 071; and Borlinghaus et al. (1987) *Cancer Res.* 47: 4071-4075) and suitable linkers are also described below with respect to the coupling of effectors to bispecific antibodies.

In certain preferred embodiments of the invention, the bs-scFv antibody molecules are produced by expression of recombinant antibody fragments produced in host cells. The genes for several of the scFv molecules that target various epitopes on members of the EGFR protein family have been cloned (see, e.g., Appendix A and Schier et al. (1996) *J. Mol. Biol.*, (1): 28-43) and pairs (or other combinations) of these scFv genes can be operably linked directly or via a linker molecule. The resulting nucleic acid molecules encoding the bs-scFv antibody fragments are inserted into expression vectors and introduced into host cells. The resulting bs-scFv antibody molecules are then isolated and purified from the expression system.

In certain preferred embodiments of the invention, the scFv antibody molecules are paired together with a novel linker molecule designed to protect against proteolytic degradation of the bs-scFv antibody molecules. This linker typically lacks a proteolytic cleavage site and is typically characterized by containing primarily neutral (non-charged) amino acids. One such linker sequence has the sequence: Asn Ser Gly Ala Gly Thr Ser Gly Ser Gly Ala Ser Gly Glu Gly Ser Gly Ser Lys Leu (SEQ ID NO:37).

The scFv provided in Table 2 are incorporated into new bs-scFv based upon the following factors: (1) descending affinity for a given target, (2) the lack of cross-reactive epitopes (as determined by binding inhibition and sandwich assays on a BIAcore), (3) combinations that target EGFR family member pairs that have not yet been paired, and (4) inclusion of scFv arms that have led to growth inhibition and altered signal transduction when employed in other bs-scFv combinations.

The purity of the bs-scFv antibody molecules of the invention may be assessed using standard methods known to those of skill in the art, including, but not limited to, ELISA, immunohistochemistry, ion-exchange chromatography, affinity chromatography, immobilized metal affinity chromatography (IMAC), size exclusion chromatography, polyacrylamide gel electrophoresis (PAGE), western blotting, surface plasmon resonance and mass spectroscopy.

Using the antibodies, nucleic acid sequences, and other teaching provided herein, bispecific or polyspecific antibodies of this invention can be recombinantly expressed using routine methods such as those set forth in Sambrook et al. (1989) *Molecular Cloning*, Cold Spring Harbor Laboratory, or Ausubel et al. (eds) (1997) *Current Protocols in Molecular Biology*, John Wiley & Sons N.Y. In addition illustrative methods of producing recombinant bispecific single chain antibodies of this invention are set forth in the Examples. To the extent that specific materials are mentioned, it is merely for purposes of illustration and is not intended to limit the invention.

III. Chimeric Moieties Comprising Bispecific and/or Polyspecific Antibodies.

In many embodiments, the bispecific and/or polyspecific anti-EGFR family member antibodies of this invention are capable of inhibiting cancer cell growth and/or proliferation without the use of any additional "effector", in certain embodiments, the bispecific and/or polyspecific antibodies are additionally coupled to an effector thereby forming chimeric moieties that preferentially target/deliver the effector to a cell overexpressing the EGFR family member or members.

Since EGFR proteins are often found in upregulated in cancer cells, these proteins can be can be exploited as target(s) for the efficient and specific delivery of an effector (e.g. an effector molecule such as a cytotoxin, a radiolabel, etc.) to various cancer cells (e.g. isolated cells, metastatic cells, solid tumor cells, etc.), in particular to epithelial cancer cells (e.g. breast cancer cells). The target EGFR protein(s) need not exist solely on cancer cells to provide an effective target. Differential expression of EGFR on cancer cells, as compared to healthy cells, is sufficient to provide significant and useful targeting advantage, i.e. resulting in preferential delivery of the effector moiety to and/or into the target (e.g. cancer) cell.

In certain preferred embodiments, the bispecific or polyspecific antibodies of this invention are utilized in a "pretargeting" strategy (resulting in formation of a chimeric moiety at the target site after administration of the effector moiety) or in a "targeting" strategy where the bispecific and/or polyspecific antibody is coupled to an effector molecule prior to use to provide a chimeric moiety.

A chimeric molecule or chimeric composition or chimeric moiety refers to a molecule or composition wherein two or more molecules or compositions that exist separately in their native state are joined together to form a single molecule moiety or composition having the desired functionality of its constituent members. Typically, one of the constituent molecules of a chimeric moiety is a "targeting molecule". i.e., in the present case a bispecific or polyspecific antibody that specifically binds one or more members of the EGFR family.

Another constituent of the chimeric molecule is an "effector". The effector molecule refers to a molecule or group of molecules that is to be specifically transported to the target cell (e.g., a cell overexpressing an EGFR family member). The effector molecule typically has a characteristic activity that is to be delivered to the target cell. Effector molecules include, but are not limited to cytotoxins, labels, radionuclides, ligands, antibodies, drugs, liposomes, and the like.

In certain embodiments, the effector is a detectable label, with preferred detectable labels including radionuclides. Among the radionuclides and labels useful in the radionuclide-chelator—(e.g. biotin) conjugates of the present invention, gamma-emitters, positron-emitters, x-ray emitters and fluorescence-emitters are suitable for localization, diagnosis and/or staging, and/or therapy, while beta and alpha-emitters and electron and neutron-capturing agents, such as boron and uranium, also can be used for therapy.

The detectable labels can be used in conjunction with an external detector and/or an internal detector and provide a means of effectively localizing and/or visualizing, e.g. cancer cells overexpressing one or more EGFR family members. Such detection/visualization can be useful in various contexts including, but not limited to pre-operative and intraoperative settings. Thus, in certain embodiment this invention relates to a method of intraoperatively detecting and locating tissues having EGFR family markers in the body of a mammal. These methods typically involve administering to the mammal a composition comprising, in a quantity sufficient for detection by a detector (e.g. a gamma detecting probe), a bispecific and/or polyspecific antibody of this invention labeled with a detectable label (e.g., antibodies of this invention labeled with a radioisotope, e.g. $^{161}$Tb, $^{123}$I, $^{125}$I, and the like), and, after allowing the active substance to be taken up by the target tissue, and preferably after blood clearance of the label, subjecting the mammal to a radioimmunodetection technique in the relevant area of the body, e.g. by using a gamma detecting probe.

The label-bound a bispecific and/or polyspecific antibody can be used in the technique of radioguided surgery, wherein relevant tissues in the body of a subject can be detected and located intraoperatively by means of a detector, e.g. a gamma detecting probe. The surgeon can, intraoperatively, use this probe to find the tissues in which uptake of the compound labeled with a radioisotope, that is, e.g. a low-energy gamma photon emitter, has taken place.

In addition to detectable labels, preferred effectors include cytotoxins (e.g. *Pseudomonas* exotoxin, ricin, abrin, *Diphtheria* toxin, and the like), or cytotoxic drugs or prodrugs, in which case the chimeric moiety can act as a potent cell-killing agent specifically targeting the cytotoxin to cells bearing the EGFR family member(s).

In still other embodiments, the effector can include a liposome encapsulating a drug (e.g. an anti-cancer drug such as doxirubicin, vinblastine, taxol, etc.), an antigen that stimulates recognition of the bound cell by components of the immune system, an antibody that specifically binds immune system components and directs them to the target cell(s), and the like.

A) The Bispecific or Polyspecific Anti-EGFR Family Member Targeting Molecule.

In preferred embodiments, of the methods and compositions of this invention, the targeting moiety is a bispecific and/or polyspecific antibody that specifically binds to one or more members of the EGFR family as described herein. The bispecific and/or polyspecific antibody can comprise full-length antibodies, antibody fragment(s) (e.g. Fv, Fab, etc.), and/or single chain antibodies (e.g. scFv).

B) Certain Preferred Effectors.

1) Imaging Compositions.

In certain embodiments, the chimeric molecules of this invention can be used to direct detectable labels to a tumor site. This can facilitate tumor detection and/or localization. In certain particularly preferred embodiments, the effector component of the chimeric molecule is a "radiopaque" label, e.g. a label that can be easily visualized using x-rays. Radiopaque materials are well known to those of skill in the art. The most common radiopaque materials include iodide, bromide or barium salts. Other radiopaque materials are also known and include, but are not limited to organic bismuth derivatives (see, e.g., U.S. Pat. No. 5,939,045), radiopaque polyurethanes (see U.S. Pat. No. 5,346,9810, organobismuth composites (see, e.g., U.S. Pat. No. 5,256,334), radiopaque barium polymer complexes (see, e.g., U.S. Pat. No. 4,866,132), and the like.

The a bispecific and/or polyspecific antibodies of this invention) can be coupled directly to the radiopaque moiety or they can be attached to a "package" (e.g. a chelate, a liposome, a polymer microbead, etc.) carrying or containing the radiopaque material as described below.

In addition to radioopaque labels, other labels are also suitable for use in this invention. Detectable labels suitable for use as the effector molecule component of the chimeric molecules of this invention include any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads.

Various preferred radiolabels include, but are not limited to $^{99}$Tc, $^{203}$Pb, $^{67}$Ga, $^{68}$Ga, $^{72}$As, $^{111}$In, $^{113m}$In, $^{97}$Ru, $^{62}$Cu, 64lCu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, and $^{111}$Ag.

Means of detecting such labels are well known to those of skill in the art. Thus, for example, radiolabels may be detected using photographic film, scintillation detectors, and the like. Fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

In certain specific embodiments, this invention contemplates the use of immunoconjugates (chimeric moieties) for the detection of tumors and/or other cancer cells. Thus, for example, the bispecific antibodies of this invention can be conjugated to gamma-emitting radioisotopes (e.g., Na-22, Cr-51, Co-60, Tc-99, I-125, I-131, Cs-137, GA-67, Mo-99) for detection with a gamma camera, to positron emitting isotopes (e.g. C-11, N-13, O-15, F-18, and the like) for detection on a Positron Emission Tomography (PET) instrument, and to metal contrast agents (e.g., Gd containing reagents, Eu containing reagents, and the like) for magnetic resonance imaging (MRI), In addition, the bispecific antibodies of this invention can be used in traditional immunohistochemistry (e.g. fluorescent labels, nanocrystal labels, enzymatic and colormetric labels etc.).

2) Radiosensitizers.

In another embodiment, the effector can be a radiosensitizer that enhances the cytotoxic effect of ionizing radiation (e.g., such as might be produced by $^{60}$Co or an x-ray source) on a cell. Numerous radiosensitizing agents are known and include, but are not limited to benzoporphyrin derivative compounds (see, e.g., U.S. Pat. No. 5,945,439), 1,2,4-benzotriazine oxides (see, e.g., U.S. Pat. No. 5,849,738), compounds containing certain diamines (see, e.g., U.S. Pat. No. 5,700,825), BCNT (see, e.g., U.S. Pat. No. 5,872,107), radiosensitizing nitrobenzoic acid amide derivatives (see, e.g., U.S. Pat. No. 4,474,814), various heterocyclic derivatives (see, e.g., U.S. Pat. No. 5,064,849), platinum complexes (see, e.g., U.S. Pat. No. 4,921,963), and the like.

3) Ligands.

The effector molecule may also be a ligand, an epitope tag, or an antibody. Particularly preferred ligand and antibodies are those that bind to surface markers on immune cells. Chimeric molecules utilizing such antibodies as effector molecules act as bifunctional linkers establishing an association between the immune cells bearing binding partner for the ligand or antibody and the tumor cells expressing the EGFR family member(s).

3) Chelates

Many of the pharmaceuticals and/or radiolabels described herein are preferably provided as a chelate, particularly where a pre-targeting strategy is utilized. The chelating molecule is typically coupled to a molecule (e.g. biotin, avidin, streptavidin, etc.) that specifically binds an epitope tag attached to the a bispecific and/or polyspecific antibody.

Chelating groups are well known to those of skill in the art. In certain embodiments, chelating groups are derived from ethylene diamine tetra-acetic acid (EDTA), diethylene triamine penta-acetic acid (DTPA), cyclohexyl 1,2-diamine tetra-acetic acid (CDTA), ethyleneglycol-O,O'-bis(2-aminoethyl)-N,N,N',N'-tetra-acetic acid (EGTA), N,N-bis(hydroxybenzyl)-ethylenediamine-N,N'-diacetic acid (HBED), triethylene tetramine hexa-acetic acid (TTHA), 1,4,7,10-tetraazacyclododecane-N,N'-,N'',N'''-tetra-acetic acid (DOTA), hydroxyethyldiamine triacetic acid (HEDTA), 1,4,8,11-tetraazacyclotetradecane-N,N',N'',N'''-tetra-acetic acid (TETA), substituted DTPA, substituted EDTA, and the like.

Examples of certain preferred chelators include unsubstituted or, substituted 2-iminothiolanes and 2-iminothiacyclohexanes, in particular 2-imino-4-mercaptomethylthiolane, and SAPS(N-(4-[211At]astatophenethyl)succinimate).

One chelating agent, 1,4,7,10-tetraazacyclododecane-N, N,N'',N'''-tetraacetic acid (DOTA), is of particular interest because of its ability to chelate a number of diagnostically and therapeutically important metals, such as radionuclides and radiolabels.

Conjugates of DOTA and proteins such as antibodies have been described. For example, U.S. Pat. No. 5,428,156 teaches a method for conjugating DOTA to antibodies and antibody fragments. To make these conjugates, one carboxylic acid group of DOTA is converted to an active ester which can react with an amine or sulfhydryl group on the antibody or antibody fragment. Lewis et al. (1994) *Bioconjugate Chem.* 5: 565-576, describes a similar method wherein one carboxyl group of DOTA is converted to an active ester, and the activated DOTA is mixed with an antibody, linking the antibody to DOTA via the epsilon-amino group of a lysine residue of the antibody, thereby converting one carboxyl group of DOTA to an amide moiety.

Alternatively the chelating agent can be coupled, directly or through a linker, to an epitope tag or to a moiety that binds an epitope tag. Conjugates of DOTA and biotin have been described (see, e.g., Su (1995) *J. Nucl. Med.*, 36 (5 Suppl): 154P, which discloses the linkage of DOTA to biotin via available amino side chain biotin derivatives such as DOTA-LC-biotin or DOTA-benzyl-4-(6-amino-caproamide)-biotin). Yau et al., WO 95/15335, disclose a method of producing nitro-benzyl-DOTA compounds that can be conjugated to biotin. The method comprises a cyclization reaction via transient projection of a hydroxy group; tosylation of an amine; deprotection of the transiently protected hydroxy group; tosylation of the deprotected hydroxy group; and intramolecular tosylate cyclization. Wu et al. (1992) *Nucl. Med. Biol.*, 19(2): 239-244 discloses a synthesis of macrocylic chelating agents for radiolabeling proteins with $^{111}$IN and $^{90}$Y. Wu et al. makes a labeled DOTA-biotin conjugate to study the stability and biodistribution of conjugates with avidin, a model protein for studies. This conjugate was made using a biotin hydrazide which contained a free amino group to react with an in situ generated activated DOTA derivative.

4) Cytotoxins.

Particularly preferred cytotoxins include *Pseudomonas* exotoxins, *Diphtheria* toxins, ricin, and abrin. *Pseudomonas* exotoxin and *Dipthteria* toxin are most preferred.

*Pseudomonas* exotoxin A (PE) is an extremely active monomeric protein (molecular weight 66 kD), secreted by *Pseudomonas aeruginosa*, which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2).

The toxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2, which inactivates the protein and causes cell death. The function of domain Ib (amino acids 365-399) remains undefined, although a large part of it, amino acids 365-380, can be deleted without loss of cytotoxicity. See Siegall et al. (1989) *J. Biol. Chem.* 264: 14256-14261.

Where the targeting molecule is fused to PE, a preferred PE molecule is one in which domain Ia (amino acids 1 through 252) is deleted and amino acids 365 to 380 have been deleted from domain Ib. However all of domain Ib and a portion of domain II (amino acids 350 to 394) can be deleted, particularly if the deleted sequences are replaced with a linking peptide such as GGGGS (SEQ ID NO:11).

In addition, the PE molecules can be further modified using site-directed mutagenesis or other techniques known in the art, to alter the molecule for a particular desired application. Means to alter the PE molecule in a manner that does not substantially affect the functional advantages provided by the PE molecules described here can also be used and such resulting molecules are intended to be covered herein.

For maximum cytotoxic properties of a preferred PE molecule, several modifications to the molecule are recommended. An appropriate carboxyl terminal sequence to the recombinant molecule is preferred to translocate the molecule into the cytosol of target cells. Amino acid sequences which have been found to be effective include, REDLK (SEQ ID NO:23) (as in native PE), REDL (SEQ ID NO:24), RDEL (SEQ ID NO:25), or KDEL (SEQ ID NO:26), repeats of those, or other sequences that function to maintain or recycle proteins into the endoplasmic reticulum, referred to here as "endoplasmic retention sequences". See, for example, Chaudhary et al. (1991) *Proc. Natl. Acad. Sci. USA* 87:308-312 and Seetharam et al, *J. Biol. Chem.* 266: 17376-17381. Preferred forms of PE comprise the PE molecule designated PE38QQR. (Debinski et al. *Bioconj. Chem.*, 5: 40 (1994)), and PE4E (see, e.g., Chaudhary et al. (1995) *J. Biol. Chem.*, 265:16306).

Methods of cloning genes encoding PE fused to various ligands are well known to those of skill in the art (see, e.g., Siegall et al. (1989) *FASEB J.*, 3: 2647-2652; and Chaudhary et al. (1987) *Proc. Natl. Acad. Sci. USA*, 84: 4538-4542).

Like PE, diphtheria toxin (DT) kills cells by ADP-ribosylating elongation factor 2 thereby inhibiting protein synthesis. *Diphtheria* toxin, however, is divided into two chains, A and B, linked by a disulfide bridge. In contrast to PE, chain B of DT, which is on the carboxyl end, is responsible for receptor binding and chain A, which is present on the amino end, contains the enzymatic activity (Uchida et al. (972) *Science*, 175: 901-903; Uchida et al. (1973) *J. Biol. Chem.*, 248: 3838-3844).

In a preferred embodiment, the targeting molecule-*Diphtheria* toxin fusion proteins of this invention have the native receptor-binding domain removed by truncation of the *Diphtheria* toxin B chain. Particularly preferred is DT388, a DT in which the carboxyl terminal sequence beginning at residue 389 is removed. Chaudhary et al. (1991) *Bioch. Biophys. Res. Comm.*, 180: 545-551. Like the PE chimeric cytotoxins, the DT molecules may be chemically conjugated to the antibody, but, in certain preferred embodiments, the targeting molecule will be fused to the *Diphtheria* toxin by recombinant means (see, e.g., Williams et al. (1990) *J. Biol. Chem.* 265: 11885-11889).

5) Other Therapeutic Moieties.

Other suitable effector molecules include pharmacological agents or encapsulation systems containing various pharmacological agents. Thus, the targeting molecule of the chimeric molecule may be attached directly to a drug that is to be delivered directly to the tumor. Such drugs are well known to those of skill in the art and include, but are not limited to, doxirubicin, vinblastine, genistein, an antisense molecule, and the like.

Alternatively, the effector molecule may be an encapsulation system, such as a viral capsid, a liposome, or micelle that contains a therapeutic composition such as a drug, a nucleic acid (e.g. an antisense nucleic acid), or another therapeutic moiety that is preferably shielded from direct exposure to the circulatory system. Means of preparing liposomes attached to antibodies are well known to those of skill in the art. See, for example, U.S. Pat. No. 4,957,735, Connor et al. (1985) *Pharm. Ther.*, 28: 341-365.

C) Attachment of the Targeting Molecule to the Effector Molecule.

One of skill will appreciate that the a bispecific and/or polyspecific antibody of this invention and the effector moieties can typically be joined together in any order. Thus, for example, where the targeting molecule is a single chain protein the effector molecule may be joined to either the amino or carboxy termini of the targeting molecule. The effector can also be joined to an internal region of the a bispecific and/or polyspecific antibody, or conversely. Similarly, the a bispecific and/or polyspecific antibody can be joined to an internal location or a terminus of the effector molecule. In any case, attachment points are selected that do not interfere with the respective activities of the a bispecific and/or polyspecific antibody or the effector.

The bispecific and/or polyspecific antibody and the effector molecule can be attached by any of a number of means well known to those of skill in the art. Typically the effector molecule is conjugated, either directly or through a linker (spacer), to the bispecific antibody. However, where both the effector molecule and the bispecific antibody are both polypeptides it is preferable to recombinantly express the chimeric molecule as a single-chain fusion protein.

1) Conjugation of the Effector Molecule to the Targeting Molecule.

In one embodiment, the a bispecific and/or polyspecific antibody is chemically conjugated to the effector molecule (e.g., a cytotoxin, a label, a ligand, a drug, an antibody, a liposome, etc.). Means of chemically conjugating molecules are well known to those of skill.

The procedure for attaching an agent to an antibody or other polypeptide targeting molecule will vary according to the chemical structure of the agent. Polypeptides typically contain variety of functional groups; e.g., carboxylic acid (COOH) or free amine (—$NH_2$) groups, which are available for reaction with a suitable functional group on an effector molecule to bind the effector thereto.

Alternatively, the bispecific antibody and/or effector molecule can be derivatized to expose or attach additional reactive functional groups. The derivatization can involve attachment of any of a number of linker molecules such as those available from Pierce Chemical Company, Rockford Ill.

A "linker", as used herein, is a molecule that is used to join the targeting molecule to the effector molecule. The linker is capable of forming covalent bonds to both the targeting molecule and to the effector molecule. Suitable linkers are well known to those of skill in the art and include, but are not limited to, straight or branched-chain carbon linkers, heterocyclic carbon linkers, or peptide linkers. Where the a bispecific and/or polyspecific antibody and the effector molecule are polypeptides, the linkers can be joined to the constituent amino acids through their side groups (e.g., through a disulfide linkage to cysteine). However, in a preferred embodiment, the linkers will be joined to the alpha carbon amino and carboxyl groups of the terminal amino acids.

A bifunctional linker having one functional group reactive with a group on a particular agent, and another group reactive with an antibody, can be used to form the desired immunoconjugate. Alternatively, derivatization can involve chemical treatment of the a bispecific and/or polyspecific antibody, e.g., glycol cleavage of a sugar moiety of a glycoprotein antibody with periodate to generate free aldehyde groups. The free aldehyde groups on the antibody can be reacted with free amine or hydrazine groups on an agent to bind the agent thereto. (See U.S. Pat. No. 4,671,958). Procedures for generation of free sulfhydryl groups on polypeptide, such as antibodies or antibody fragments, are also known (See U.S. Pat. No. 4,659,839).

Many procedures and linker molecules for attachment of various compounds including radionuclide metal chelates, toxins and drugs to proteins such as antibodies are known (see, e.g., European Patent Application No. 188,256; U.S. Pat. Nos. 4,671,958, 4,659,839, 4,414,148, 4,699,784; 4,680, 338; 4,569,789; and 4,589,071; and Borlinghaus et al. (1987) *Cancer Res.* 47: 4071-4075). In particular, production of various immunotoxins is well-known within the art and can be found, for example in "Monoclonal Antibody-Toxin Conjugates: Aiming the Magic Bullet," Thorpe et al., *Monoclonal Antibodies in Clinical Medicine*, Academic Press, pp. 168-190 (1982), Waldmann (1991) *Science*, 252: 1657, U.S. Pat. Nos. 4,545,985 and 4,894,443.

In some circumstances, it is desirable to free the effector molecule from the a bispecific and/or polyspecific antibody when the chimeric moiety has reached its target site. Therefore, chimeric conjugates comprising linkages that are cleavable in the vicinity of the target site can be used when the effector is to be released at the target site. Cleaving of the linkage to release the agent from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

2 Conjugation of Chelates.

In certain preferred embodiments, the effector comprises a chelate that is attached to an antibody or to an epitope tag. The a bispecific and/or polyspecific antibody bears a corresponding epitope tag or antibody so that simple contacting of the a bispecific and/or polyspecific antibody to the chelate results in attachment of the antibody to the effector. The combining step can be performed after the moiety is used (pretargeting strategy) or the target tissue can be bound to the a bispecific and/or polyspecific antibody before the chelate is delivered. Methods of producing chelates suitable for coupling to various targeting moieties are well known to those of skill in the art (see, e.g., U.S. Pat. Nos. 6,190,923, 6,187,285, 6,183,721, 6,177,562, 6,159,445, 6,153,775, 6,149,890, 6,143,276, 6,143,274, 6,139,819, 6,132,764, 6,123,923, 6,123,921, 6,120,768, 6,120,751, 6,117,412, 6,106,866, 6,096,290, 6,093,382, 6,090,800, 6,090,408, 6,088,613, 6,077,499, 6,075,010, 6,071,494, 6,071,490, 6,060,040, 6,056,939, 6,051,207, 6,048,979, 6,045,821, 6,045,775, 6,030,840, 6,028,066, 6,022,966, 6,022,523, 6,022,522, 6,017,522, 6,015,897, 6,010,682, 6,010,681, 6,004,533, and 6,001,329).

3) Production of Fusion Proteins.

Where the a bispecific and/or polyspecific antibody and/or the effector molecule are both single chain proteins and relatively short (i.e., less than about 50 amino acids) they can be synthesized using standard chemical peptide synthesis techniques. Where both components are relatively short the chimeric moiety can be synthesized as a single contiguous polypeptide. Alternatively the a bispecific and/or polyspecific antibody and the effector molecule may be synthesized separately and then fused by condensation of the amino terminus of one molecule with the carboxyl terminus of the other molecule thereby forming a peptide bond. Alternatively, the a bispecific and/or polyspecific antibody and effector molecules may each be condensed with one end of a peptide spacer molecule thereby forming a contiguous fusion protein.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, *Solid-Phase Peptide Synthesis*; pp. 3-284 in *The Peptides: Analysis, Synthesis, Biology. Vol. 2: Special Methods in Peptide Synthesis, Part A.*, Merrifield, et al. *J. Am. Chem. Soc.*, 85: 2149-2156 (1963), and Stewart et al., *Solid Phase Peptide Synthesis*, 2nd ed. Pierce Chem. Co., Rockford, Ill. (1984).

In a preferred embodiment, the where the a bispecific and/or polyspecific antibody is a single chain polypeptide and the effector is a polypeptide, chimeric fusion proteins of the present invention are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins (e.g. ALM-PE38QQR) of this invention may be prepared by any suitable method, including, for example, cloning and restriction of appropriate sequences or direct chemical synthesis by methods such as the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.*, 22: 1859-1862; and the solid support method of U.S. Pat. No. 4,458,066.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences can be obtained by the ligation of shorter sequences.

Alternatively, subsequences can be cloned and the appropriate subsequences cleaved using appropriate restriction enzymes. The fragments can then be ligated to produce the desired DNA sequence.

In a preferred embodiment, DNA encoding fusion proteins of the present invention may be cloned using DNA amplification methods such as polymerase chain reaction (PCR). Thus, for example, the nucleic acid encoding a bispecific and/or polyspecific antibody is PCR amplified, using a sense primer containing the restriction site for NdeI and an antisense primer containing the restriction site for HindIII. This produces a nucleic acid encoding the a bispecific and/or polyspecific antibody sequence and having terminal restriction sites. A PE38QQR fragment can be cut out of the plasmid pWDMH4-38QQR or plasmid pSGC242FdN1 described by Debinski et al. (1994) *Int. J. Cancer,* 58: 744-748. Ligation of the a bispecific and/or polyspecific antibody and PE38QQR sequences and insertion into a vector produces a vector encoding the bispecific and/or polyspecific antibody joined to the amino terminus of PE38QQR (position 253 of PE). The two molecules are joined by a three amino acid junction consisting of glutamic acid, alanine, and phenylalanine introduced by the restriction site.

While the two molecules are preferably essentially directly joined together, one of skill will appreciate that the molecules may be separated by a peptide spacer consisting of one or more amino acids. Generally the spacer will have no specific biological activity other than to join the proteins or to preserve some minimum distance or other spatial relationship between them. However, the constituent amino acids of the spacer can be selected to influence some property of the molecule such as the folding, net charge, or hydrophobicity.

The nucleic acid sequences encoding the fusion proteins can be expressed in a variety of host cells, including *E. coli*, other bacterial hosts, yeast, and various higher eukaryotic cells such as the COS, CHO and HeLa cells lines and myeloma cell lines. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes (1982) *Protein Purification*, Springer-Verlag, N.Y.; Deutscher (1990) *Methods in Enzymology Vol. 182: Guide to Protein Purification.*, Academic Press, Inc. N.Y.). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the EGFR polypeptide targeted fusion protein can possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing refolding are well known to those of skill in the art (See, Debinski et al. (1993) *J. Biol. Chem.*, 268: 14065-14070; Kreitman and Pastan (1993) *Bioconjug. Chem.*, 4: 581-585; and Buchner, et al. (1992) *Anal. Biochem.*, 205: 263-270).

One of skill would recognize that modifications can be made to the fusion proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids placed on either terminus to create conveniently located restriction sites or termination codons.

IV. Uses of Bispecific Antibody Molecules and/or Chimeric Moieties:

Bispecific antibodies having affinity for two distinct antigens have broad applications in therapy and diagnosis. Specifically, the bs-antibody molecules of the invention (e.g., bs-scFv), can be used: (1) to directly alter the growth of tumors that overexpress members of the EGFR protein family; (2) in combination with other cytotoxic agents (e.g., chemotherapeutic agents, external beam radiation, targeted radioisotopes, and other antibodies or signal transduction inhibitors); and (3) to recruit a variety of different cytotoxic agents or effector cells directly to targeted tumor cells that express members of the EGFR protein family.

Targeting cytotoxic agents or effector cells to specific tumor cells utilizing the bs-scFv antibody molecules of the invention provides added tumor-directed specificity due to the increased expression of these targets on tumor cells relative to normal tissue. In addition, the bispecific antibodies can bind to multiple receptors or receptor components, thereby cross-linking receptors or receptor components producing a cytotoxic and/or cytostatic effect. Antibody-based agents that only bind to one target on normal tissue will typically not crosslink the receptors and trigger cytotoxic results.

In addition, monospecific antibodies typically show lower avidity to the target cell. In contrast, the bispecific antibodies of this invention show higher avidity to the target cell(s) which helps stabilize the antibody/target complex and provide long-term association of the antibody with the cell, thus providing added specificity for the agent on tumor cells that overexpress both targets.

In addition, the binding of antibodies to the members of the EGFR protein family often triggers the internalization of these proteins, making these antibodies effective platforms for the delivery of toxins, drugs, radioisotopes or other cytotoxic agents. ALM mediates a reduction in the quantity of HER2/neu and HER3 on the surface of tumor cells, suggesting a similar internalization mechanism. Therefore, the combination of these bs-scFv molecules with cytotoxic or other agents (effectors), e.g. in a chimeric moiety, will result in effective delivery to cells that overexpress both targets, thus increasing the specificity and efficacy of the therapy. By incorporating additional sequences (e.g., Fc receptor targeting arms) that interact with effector cells, a similar increase in targeting specificity can also be incorporated into effector cell-based treatment strategies.

The bispecific antibody molecules of the invention can also be used in gene therapy for direct targeting and internalization of nucleic acids encoding therapeutic agents (e.g. pseudomonas exotoxin, diphtheria toxin, various tumor suppressor genes, various labels, etc.), In addition, the bispecific antibodies can be conjugated, e.g. via a chelate to cytotoxic radioactive moieties (e.g. $^{211}$At), to radiation enhancing agents, and to various detectable labels (e.g. radio opaque labels). In addition, the bispecific antibody molecules can be coupled to lipids, liposomes, dendrimers, and the like. The lipids, liposomes and dendrimers can combine with and/or encapsulate various therapeutic moieties (e.g. anticancer drugs including, but not limited to, alkylating agents such as busulfan, chlorambuicl, cis-platinum, cyanomorpholino-doxorubicin, etc., antimitotic agents such as allocolchicine, cohchicine, taxol, vinblastine, vincristine, and the like, topoisomerase I inhibitors such as camptothecin, aminocamptothecin, and the like, topoisomerase II inhibitors such as doxorubicin, amonafide, daunorubicin, deoxydoxorubicin, mitoxantrone, and the like, RNA/DNA antimetabolites such as acivicin, ftorafur, methotrexate, trimetrexate, and the like; DNA antimetabolites such as 2'deoxy-5-fluorouridine, cyclocytidine, guanazole, and the like). Lipids, liposomes and dendrimers can also complex with protein therapeutics, nucleic acids encoding, e.g. therapeutic moieties, and the like.

When used as a targeting component of a chimeric moiety, as described above, the bispecific and/or polyspecific antibodies of this invention preferentially target/deliver the associated effector to the target cell(s) expressing the target EGFR proteins. By increasing the association (e.g. duration of contact or amount of contact) of the effector with the cell (in contact or close proximity), the antibodies of this invention increase the likelihood of the effector internalizing into the cell and/or exerting its characteristic activity on that cell.

Thus, for example, bispecific or polyspecific antibody targeted liposomes or other therapeutic vesicles (liposomes, viruses etc.) show increased exposure (duration/concentration) to target tumors. In an exemplary embodiment, liposomes can be studded by the bs-scFv antibody molecules of the invention to facilitate tumor specific targeting. Anti-cancer agents such as chemotherapeutic agents, antibodies, antisense molecules and/or radioisotopes may be encapsulated in liposomes so modified.

In another embodiment, the bispecific or poylyspecific antibody (e.g., bs-scFv antibody) molecules can be used to direct gene therapy vectors, including but not limited to modified viruses, to cells that express both target antigens. Viruses can also be utilized to deliver the genes for these bs-scFv antibody molecules to tumor cells where they could be produced and secreted into the cellular microenvironment or, through the addition of additional intracellular targeting sequences, they could be turned into intrabodies that localize to specific cellular compartments and knockout the expression of their targets.

In addition, the bispecific or poylyspecific antibody (e.g., bs-scFv antibody) molecules of the invention can be used to advantage to detect aberrant expression of members of the EGFR protein family. Such detection can lead to early diagnosis of cancers associated with aberrant tumor growth facilitated by these cell surface proteins. In general, the detection of immunocomplex formation is well known in the art and can be achieved through the application of numerous approaches. These methods are generally based upon the detection of a label or marker, such as any radioactive, fluorescent, biological or enzymatic tags or labels of standard use in the art. U.S. patents concerning the use of such labels include U.S. Pat. Nos. 3,817,837; 3,850,752; 3,939,350; 3,996,345; 4,277,437; 4,275,149 and 4,366,241. Of course, one may find additional advantages through the use of a secondary binding ligand such as a second antibody or a biotin/avidin ligand binding arrangement, as is known in the art.

V. Administration of bs-scFv Antibody Molecules:

A) Pharmaceutical Formulations.

Bispecific antibodies or bs-scFv antibody molecules or chimeric moieties, as described herein, include bulk drug compositions useful in the manufacture of non-pharmaceutical compositions (e.g., impure or non-sterile compositions), and pharmaceutical compositions (i.e., compositions that are suitable for administration to a subject or patient (i.e., human or non-human subject) that can be used directly and/or in the preparation of unit dosage forms. In certain embodiments, such compositions comprise a therapeutically effective amount of one or more therapeutic agents (e.g. bispecific and/or polyspecific antibodies, and/or chimeric moieties comprising such antibodies) and a pharmaceutically acceptable carrier.

As indicated above, the agents of this invention can be used in a wide variety of contexts including, but not limited to the detection and/or imaging of tumors or cancer cells, inhibition of tumor growth and/or cancer cell growth and/or proliferation, and the like. One or more bispecific antibodies, and/or functionalized bispecific antibodies, and/or chimeric moieties of this invention can be administered by injection, that is, intravenously, intramuscularly, intracutaneously, subcutaneously, intraduodenally, or intraperitoneally. Also, in certain embodiments, the compounds can be administered by inhalation, for example, intranasally. Additionally, certain compounds can be administered orally, or transdermally.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans, or suitable for administration to an animal or human. The term "carrier" or refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of the compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be provided as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Pharmaceutical compositions comprising the bispecific antibodies, and/or functionalized bispecific antibodies, and/ or chimeric moieties of this invention can be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries that facilitate processing of the molecules into preparations that can be used pharmaceutically. Proper formulation is dependent upon the route of administration chosen.

For topical or transdermal administration, the bispecific antibodies, and/or functionalized bispecific antibodies, and/ or chimeric moieties of this invention can be formulated as solutions, gels, ointments, creams, lotion, emulsion, suspensions, etc. as are well-known in the art. Systemic formulations include those designed for administration by injection, e.g. subcutaneous, intravenous, intramuscular, intrathecal or intraperitoneal injection, as well as those designed for transdermal, transmucosal, inhalation, oral or pulmonary administration.

For injection, the bispecific antibodies, and/or functionalized bispecific antibodies, and/or chimeric moieties of this invention can be formulated in aqueous solutions, preferably in physiologically compatible buffers such as Hanks's solution, Ringer's solution, or physiological saline buffer. The solution can contain formulatory agents such as suspending, stabilizing and/or dispersing agents. Alternatively, compositions comprising the antibodies can be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, the bispecific antibodies, and/or functionalized bispecific antibodies, and/or chimeric moieties of this invention can be readily formulated by combining the agent(s) with pharmaceutically acceptable carriers well known in the art. Such carriers enable the agent(s) to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, e.g. lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like can be added.

For buccal administration, the antibodies can take the form of tablets, lozenges, etc. formulated in conventional manner.

For administration by inhalation, bispecific antibodies, and/or functionalized bispecific antibodies, and/or chimeric moieties of this invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of gelatin for use in an inhaler or insufflator may be formulated containing a powder mix of the antibodies and a suitable powder base such as lactose or starch.

The bispecific antibodies, and/or functionalized bispecific antibodies, and/or chimeric moieties of this invention (can also be formulated in rectal or vaginal compositions such as suppositories or retention enemas, e.g. containing conventional suppository bases such as cocoa butter or other glycerides.

In addition to the formulations described previously, the bispecific antibodies, and/or functionalized bispecific antibodies, and/or chimeric moieties of this invention can also be formulated as a depot preparation. Such long acting formulations may be administered by implantation (for example subcutaneously or intramuscularly) or by intramuscular injection. Thus, for example, the agent(s) of this invention can be formulated with suitable polymeric or hydrophobic materials (for example as an emulsion in an acceptable oil) or ion exchange resins, or as sparingly soluble derivatives, for example, as a sparingly soluble salt.

Other pharmaceutical delivery systems can also be employed. Liposomes and emulsions are well known examples of delivery vehicles that may be used to deliver the bispecific antibodies, and/or functionalized bispecific antibodies, and/or chimeric moieties of this invention. Certain organic solvents such as dimethylsulfoxide also may be employed, although usually at the cost of greater toxicity. Additionally, the bispecific antibodies, and/or functionalized bispecific antibodies, and/or chimeric moieties of this invention can be delivered using a sustained-release system, such as semipermeable matrices of solid polymers containing the therapeutic agent. Various sustained-release materials have been established and are well known by those skilled in the art. Sustained-release capsules may, depending on their chemical nature, can release the active agent(s) for a few days, a few weeks, or up to over 100 days. Depending on the chemical nature and the biological stability of the agent(s) additional strategies for stabilization can be employed.

As the bispecific antibodies, and/or functionalized bispecific antibodies, and/or chimeric moieties of this invention may contain charged side chains or termini, they can be included in any of the above-described formulations as the free acids or bases or as pharmaceutically acceptable salts. Pharmaceutically acceptable salts are those salts which substantially retain the biological activity of the free bases and which are prepared by reaction with inorganic acids. Pharmaceutical salts tend to be more soluble in aqueous and other protic solvents than are the corresponding free base forms.

B) Effective Dosages.

The bispecific antibodies, and/or functionalized bispecific antibodies, and/or chimeric moieties of this invention will generally be used in an amount effective to achieve the intended purpose (e.g. to image a tumor or cancer cell, to inhibit growth and/or proliferation of cancer cells, etc.). In certain preferred embodiments, the bispecific antibodies, and/or functionalized bispecific antibodies, and/or chimeric moieties utilized in the methods of this invention are administered at a dose that is effective to partially or fully inhibit cancer cell proliferation and/or growth, or to enable visualization of a cancer cell or tumor characterized by overexpression of an EGFR family protein. In certain embodiments, dosages are selected that inhibit cancer cell growth and/or proliferation at the 90%, more preferably at the 95%, and most preferably at the 98% or 99% confidence level. Preferred effective amounts are those that reduce or prevent tumor growth or that facilitate cancer cell detection and/or visualization. With respect to inhibitors of cell growth and proliferation, the compounds can also be used prophalactically at the same dose levels.

Typically, bispecific antibodies, and/or functionalized bispecific antibodies, and/or chimeric moieties of this invention, or pharmaceutical compositions thereof, are administered or applied in a therapeutically effective amount. A therapeutically effective amount is an amount effective to reduce or prevent the onset or progression (e.g, growth and/or proliferation) of a cancer cell and/or a tumor. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One skilled in the art could readily optimize administration to humans based on animal data.

Dosage amount and interval can be adjusted individually to provide plasma levels of the inhibitors which are sufficient to maintain therapeutic effect.

Dosages for typical therapeutics are known to those of skill in the art. Moreover, such dosages are typically advisorial in nature and may be adjusted depending on the particular therapeutic context, patient tolerance, etc. Single or multiple administrations of the compositions may be administered depending on the dosage and frequency as required and tolerated by the patient.

In certain embodiments, an initial dosage of about 1 µg, preferably from about 1 mg to about 1000 mg per kilogram daily will be effective. A daily dose range of about 5 to about 75 mg is preferred. The dosages, however, can be varied depending upon the requirements of the patient, the severity of the condition being treated, and the compound being employed. Determination of the proper dosage for a particular situation is within the skill of the art. Generally, treatment is initiated with smaller dosages that are less than the optimum dose of the compound. Thereafter, the dosage is increased by small increments until the optimum effect under the circumstance is reached. For convenience, the total daily dosage can be divided and administered in portions during the day if desired. Typical dosages will be from about 0.1 to about 500 mg/kg, and ideally about 25 to about 250 mg/kg.

In cases of local administration or selective uptake, the effective local concentration of the bispecific antibodies and/or chimeric molecules may not be related to plasma concentration. One skilled in the art will be able to optimize therapeutically effective local dosages without undue experimentation. The amount of antibody and/or chimeric moiety will, of course, be dependent on the subject being treated, on the subject's weight, the severity of the affliction, the manner of administration and the judgment of the prescribing physician.

The therapy can be repeated intermittently. In certain embodiments, the pharmaceutical preparation comprising the bispecific antibody molecules cam be administered at appropriate intervals, for example, at least twice a day or more until the pathological symptoms are reduced or alleviated, after which the dosage may be reduced to a maintenance level. The appropriate interval in a particular case would normally depend on the condition of the patient. The therapy can be provided alone or in combination with other drugs, and/or radiotherapy, and/or surgical procedures.

C) Toxicity.

Preferably, a therapeutically effective dose of bispecific antibodies, and/or functionalized bispecific antibodies, and/or chimeric moieties of this invention described herein will provide therapeutic benefit without causing substantial toxicity.

Toxicity of the agents described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Agents that exhibit high therapeutic indices are preferred. Data obtained from cell culture assays and animal studies can be used in formulating a dosage range that is not toxic for use in human. The dosage of the bispecific antibodies, and/or functionalized bispecific antibodies, and/or chimeric moieties of this invention preferably lie within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition (see, e.g., Fingl et al. (1975) In: *The Pharmacological Basis of Therapeutics*, Ch. 1, p. 1).

VI. Kits.

The present invention further encompasses kits for use in detecting cells expressing or overexpressing members of the EGFR protein family in vivo, and/or in biological samples. Kits are also provided for in inhibiting the growth and/or proliferation of cells expressing or overexpressing members of the Epidermal Growth Factor Family (e.g. cancer cells).

In certain embodiments, the kits comprise one or more bispecific and/or polyspecific antibodies of this invention specific for at least two epitopes on members of the EGFR protein family. In certain preferred embodiments, the antibodies are bispecific scFv antibodies. Depending on use, the antibodies can be functionalized with linkers and/or chelators for coupling to an effector (e.g. a radioactive moiety, a liposome, a cytoxin, another antibody, etc.) as described herein.

In certain embodiments, the kits can comprise the, e.g. bs-scFv antibody molecules of the invention specific for members of the EGFR protein family as well as buffers and other compositions to be used for detection of the bs-scFv antibody molecules.

The kits can also include instructional materials teaching the use of the antibodies for detecting, e.g. cancer cells, and/or teaching the combination of the antibodies with functionalizing reagents or teaching the use of functionalized antibodies for imaging and/or therapeutic applications. In certain embodiments, the antibody is provided functionalized with a linker and/or a chelator (in one container) along with one or more effectors, e.g. cytotoxins, radioactive labels (in a second container) such that the two components can be separately administered (e.g. in pre-targeting approaches) or such that the two components can be administered shortly before use.

Certain instructional materials will provide recommended dosage regimen, counter indications, and the like. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such.

EXAMPLES

The following examples are offered to illustrate, but not to limit the claimed invention.

Example 1

Preparation of Bs-scFv Antibody Molecules

Overexpression of EGFR and HER2/neu has been correlated with a poor prognosis in many solid tumors. Antibodies that perturb signaling through these receptors, such as Herceptin[7] (anti-HER2) and C225 (anti-EGFR), have demonstrated significant utility in the treatment of cancer. Signal transduction through members of the EGFR family (EGFR, Her-2/neu, Her3 and Her4) is dependent upon the formation of homodimers, heterodimers or heterogenous multimers of these receptors triggered by the binding of ligand. Bispecific scFv antibody molecules that engage multiple epitope pairs of these receptor proteins have been generated as described hereinbelow for use in preventing formation of these signaling complexes in cancerous tumor cells.

I. Materials and Methods:

The following materials and methods are provided to facilitate the practice of the present invention:

A. Cloning:

All of the genes coding for single chain Fv (scFv) antibody molecules specific for the different members of the EGFR family (EGFR, HER2/neu, HER3, HER4) were obtained from Dr. Jim Marks (University of California San Francisco). The scFv genes were isolated from large naïve human scFv libraries. The scFv genes specific for the EGFR proteins were isolated by selection against the extracellular domains of these proteins. All of the scFv genes were provided as inserts in a pUC119myc/his vector, between the NcoI and NotI restriction sites. Sequences for these arms are set forth in Appendix A (SEQ ID NOS: 1-10, 19, and 21).

1. Construction of 20 Amino Acid Linker Molecule:

Proteolytic degradation of the bs-scFv antibody molecules in circulation may limit their effectiveness. Thus, a novel 20 amino acid linker that was devoid of all known proteolytic sites was designed and synthesized. The amino acids employed in the construction of the linker were selected to be primarily neutral (not charged, hydrophobic or hydrophilic) to facilitate efficient transport of the protein into the bacterial periplasmic space. The following two primers were synthesized which encode the new linker molecule: LW583 (5'-AAT TCA GGT GCT GGT ACT TCA GGT TCA GGT GCT TCA GGT GAA GGT TCA GGT TCA A-3', SEQ ID NO: 12); and LW584 (5'-AGC TTT GAA CCT GAA CCT TCA CCT GAA GCA CCT GAA CCT GAA GTA CCA GCA CCT G-3', SEQ ID NO: 13).

Hybridization of these oligonucleotides formed a "sticky" ends linker with EcoRI and HindIII digested ends. This product was inserted into the pET20b(+) vector previously digested with EcoRI and HindIII. Plasmid DNA was generated from transformed DH5α E. coli using a commercially available kit for DNA plasmid isolation and purification (Qiagen or Gibco BRL Co.) and was subsequently named "pET20b(+)/Linker". The linker molecule is encoded by the following nucleic acid sequence: 5'-AAT TCA GGT GCT GGT ACT TCA GGT TCA GGT GCT TCA GGT GAA GGT TCA GGT TCA AAG CTA->3 (SEQ ID NO: 14), and the resulting linker molecule has the following amino acid sequence: NSG AGT SGS GAS GEG SGS KL (SEQ ID NO: 11).

2. Cloning Anti-HER3 Gene into pET20b(+)/Linker Vector:

The gene coding for the anti-HER3 scFv antibody molecule, A5, was amplified from the A5-pUC119myc/his plasmid with the following two primers: LW687 (5'-CGA CCA TGG CCC AGG TGC AGC TGG TGC AG-3', SEQ ID NO: 15); and LW688 (5'-CGA ATT CAC CTA GGA CGG TCA GCT TGG-3', SEQ ID NO: 16).

The amplified product and vector, pET20b(+)/Linker, were both digested with NcoI and EcoRI enzymes, ligated and transformed into competent DH5α E. coli for plasmid DNA production. Selected enzymes directed the A5 gene upstream from the linker. The new plasmid, called "pET20b(+)A5/Linker", was then isolated and purified.

3. Cloning Anti HER2/neu Gene into pET20b(+)A5/Linker Vector:

The gene coding for the anti-HER2/neu scFv antibody molecule, ML3.9, was amplified from the ML3.9-pUC119myc/his plasmid using the following two primers: LW697 (5'-GGG AAG CTT CAG GTG CAG CTG GTG CAG TCT GG-3', SEQ ID NO: 17); and LW698 (5'-GGG CTC GAG ACC TAG GAC GGT CAG CTT GGT TCC-3', SEQ ID NO: 18)

The PCR amplified product and plasmid DNA, pET20b(+) A5/Linker, were digested with HindIII and XhoI restriction enzymes, ligated and transformed into competent DH5α E. coli for production of the new plasmid DNA, pET20b(+)A5/Linker/ML3.9. Selected enzymes directed the ML3.9 gene downstream from the linker sequence. The new plasmid, called ApET20b(+)A5/Linker/ML3.9", was then isolated and purified.

4. Cloning of the A5/Linker/ML3.9 Gene into pUC119/myc/his Vector:

The nucleic acid molecule encoding the bs-scFv product from pET20b(+) was cloned into a pUC119myc/his vector. A (histidine)$_6$ tag and one "stop" codon, which are part of the pET vector, were amplified together with the A5/Linker/ML3.9 nucleic acid construct. PCR amplification was performed using the following two primers: LW687 (5'-CGA CCA TGG CCC AGG TGC AGC TGG TGC AG-3', SEQ ID NO: 5); and LW686 (5'-GAT ATA ATG CGG CCG CTC AGT GGT GGT GGT GGT G-3', SEQ ID NO: 9)

Digestion of the pUC119myc/his vector and amplified product with NcoI and NotI enzymes was followed by a ligation step and transformation of the DH5α E. coli. The resulting plasmid DNA, called "pUC/ALM", was then purified and isolated (FIG. 1).

B. Transformation of the Expression Clone, TG1:

pUC/ALM was transformed into E. coli strain, TG1, and the clones producing the A5/Linker/ML3.9 bs-scFv antibody molecules were isolated as follows. The bs-scFv molecules were dialyzed overnight, purified by immobilized metal affinity chromatography using Ni-NTA resin (Qiagen), followed by size-exclusion chromatography on an HPLC system using a Superdex-75 column (Pharmacia).

II. Results:

As a proof of concept, two different bs-scFv antibody molecules were created. The first, named "ALM", was composed of the A5 scFv and the ML3.9 scFv which specifically binds to both HER3 and HER2/neu, respectively. The second bs-scFv antibody molecule, named "ALF", was composed of two distinct scFv molecules, A5 and F4, both with a specificity for HER3. Both bs-scFv antibody molecules were cloned and expressed from E. coli.

Figure 2:
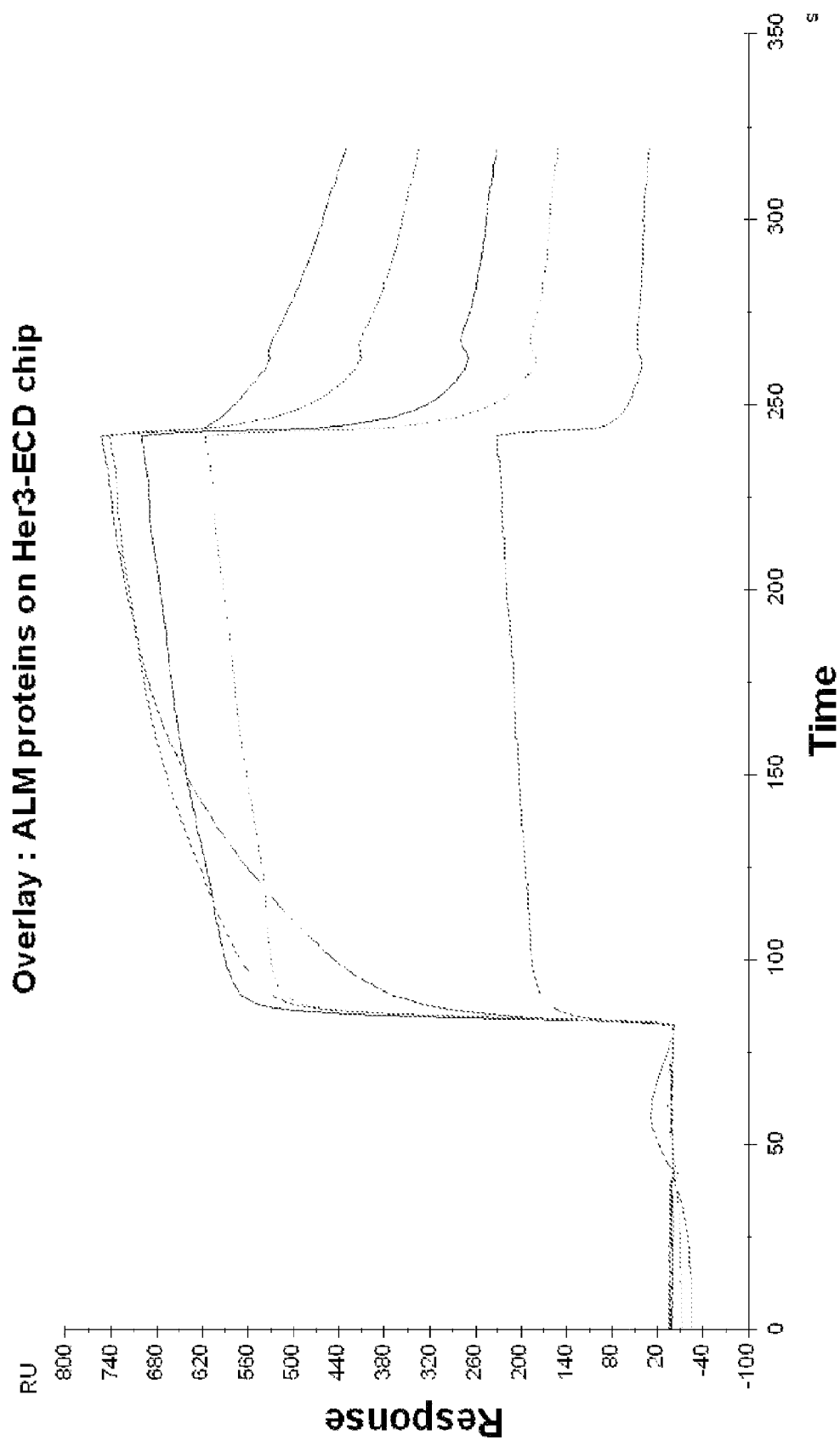
FIG. 2 shows a graph illustrating the binding of ALM proteins to the HER3 extracellular domain on a BIAcore chip.
Figure 3:
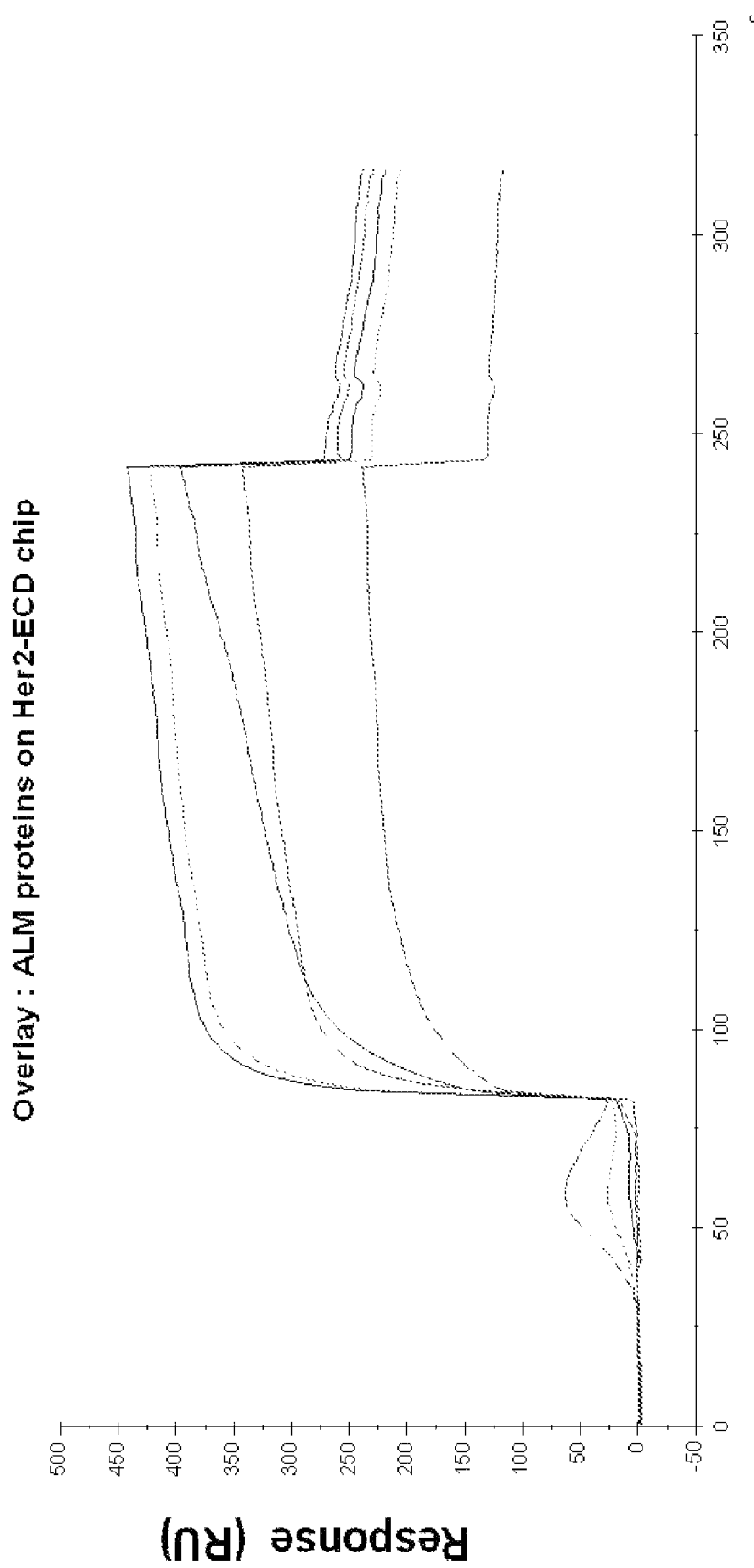
FIG. 3 shows a graph illustrating the binding of ALM proteins to the HER2/neu extracellular domain on a BIAcore chip.
Figure 4:
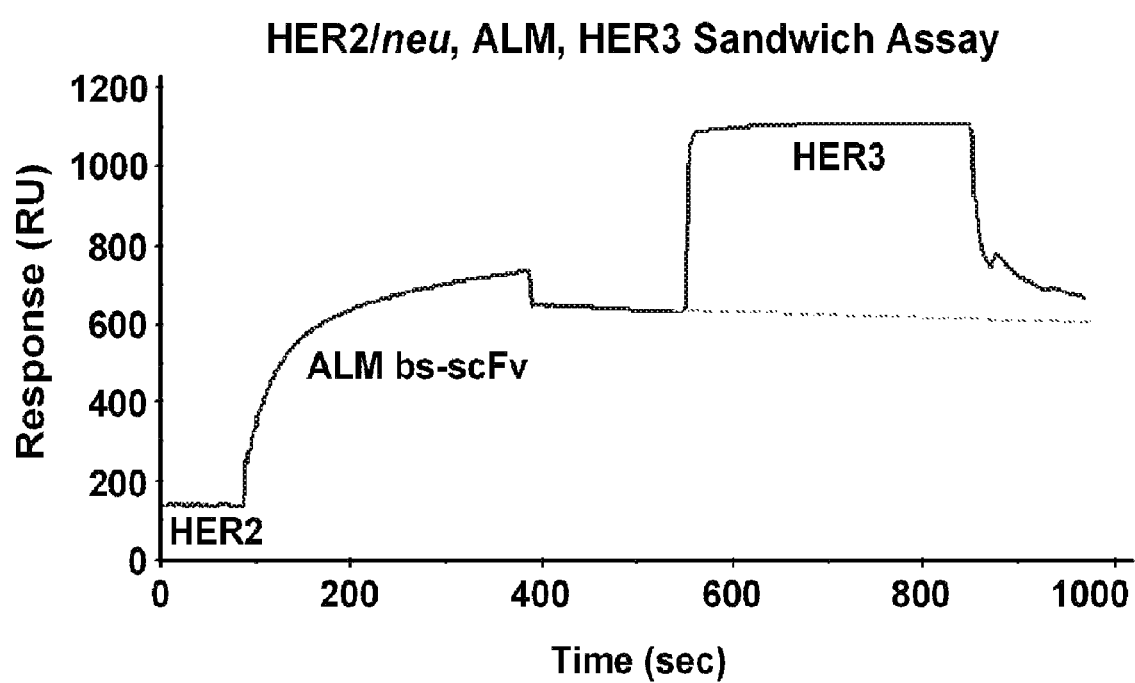
FIG. 4 shows a graph illustrating the simultaneous binding of ALM proteins to HER3 and HER2/neu on a BIAcore chip.
Figure 5A:
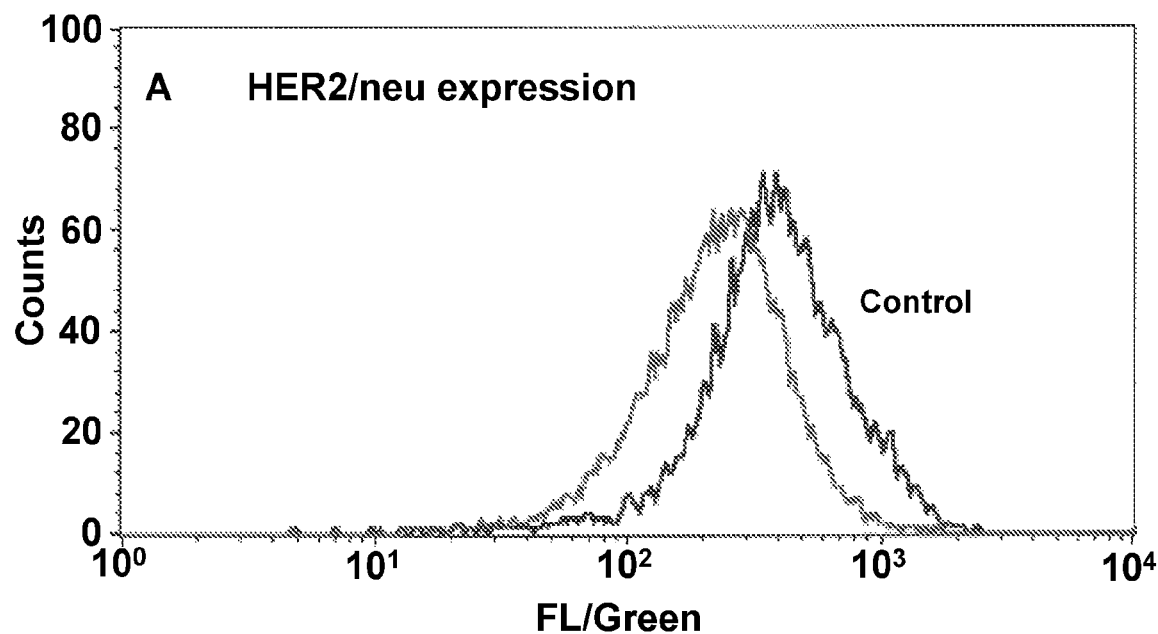
FIGS. 5A and 5B show graphs of flow cytometry results displaying a reduction in cell surface HER2/neu and HER3 following in vitro incubation of ALM with human BT-474 breast cancer cells expressing both HER2/neu and HER3.
Figure 5B:
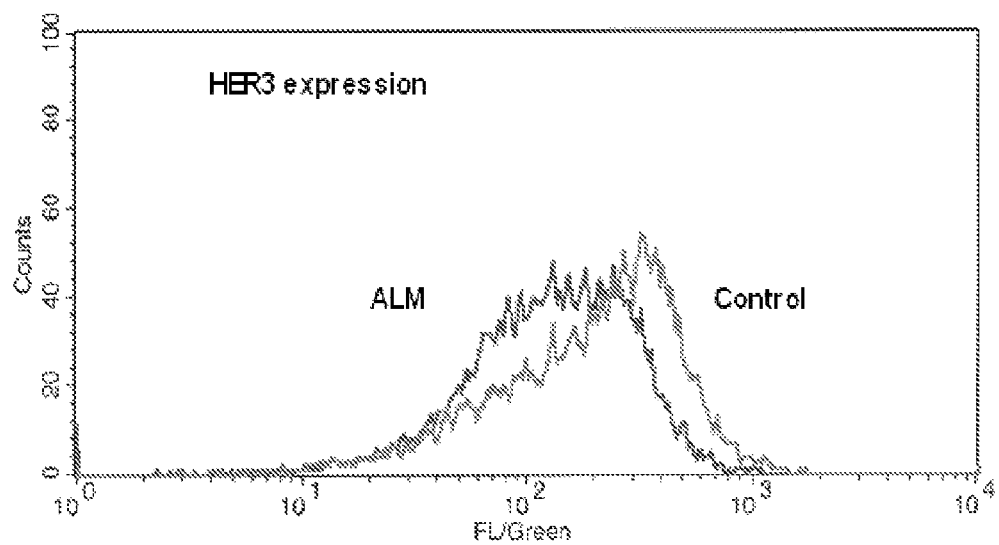
Figure 6:
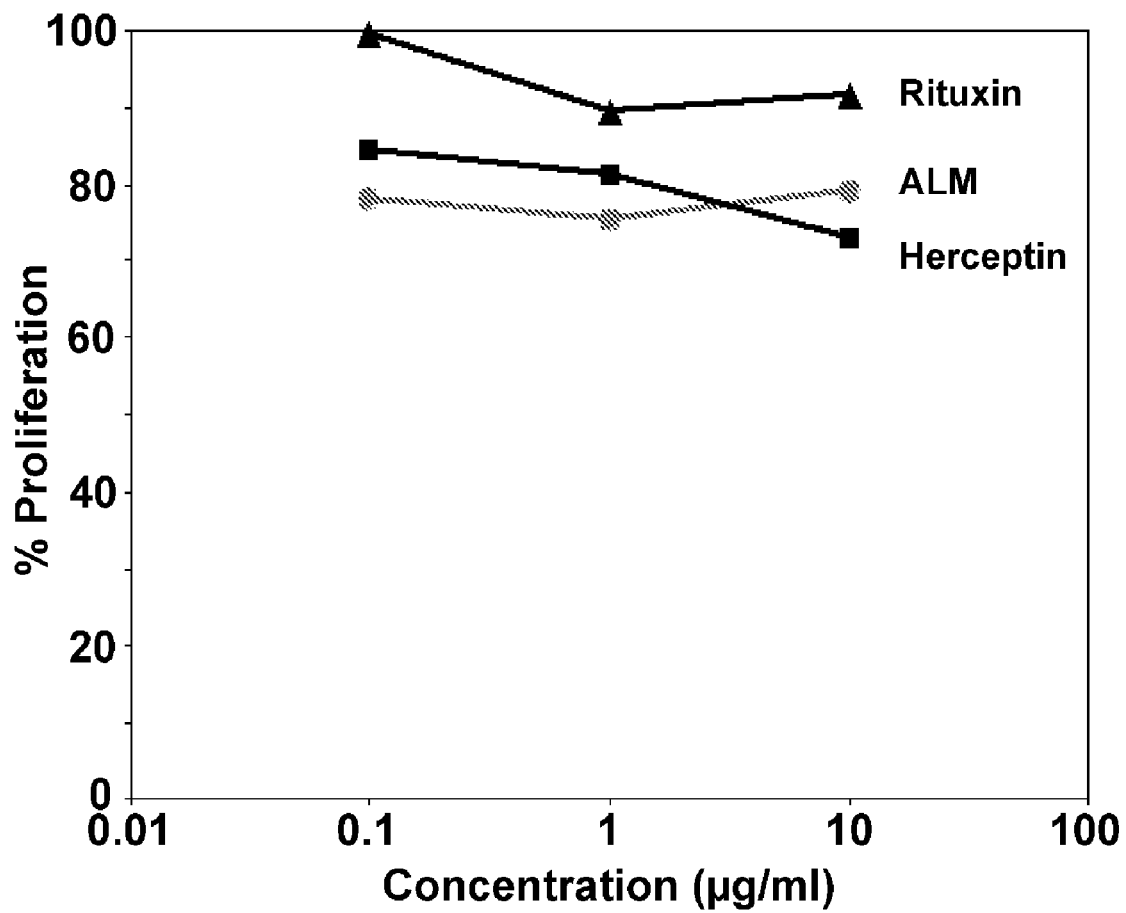
FIG. 6 Shows a graph of the results of an MTT assay demonstrating that ALM diminishes proliferation of BT-474 breast cancer cells expressing both HER2/neu and HER3.
Figure 7:
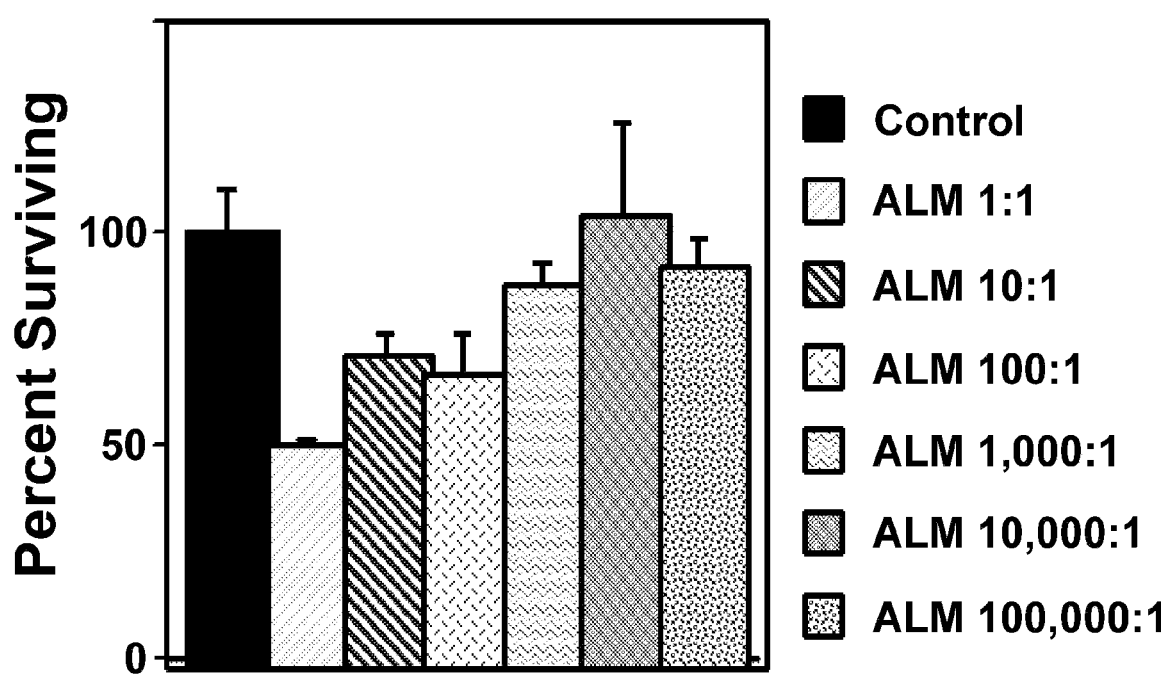
FIG. 7 shows a graph illustrating the results of a 17 day clonogenicity assay demonstrating that incubation of BT-474 cells with ALM at a concentration that is equimolar with cell surface HER2/neu expression leads to a 50% reduction in colony formation (cell survival).
Figure 8:
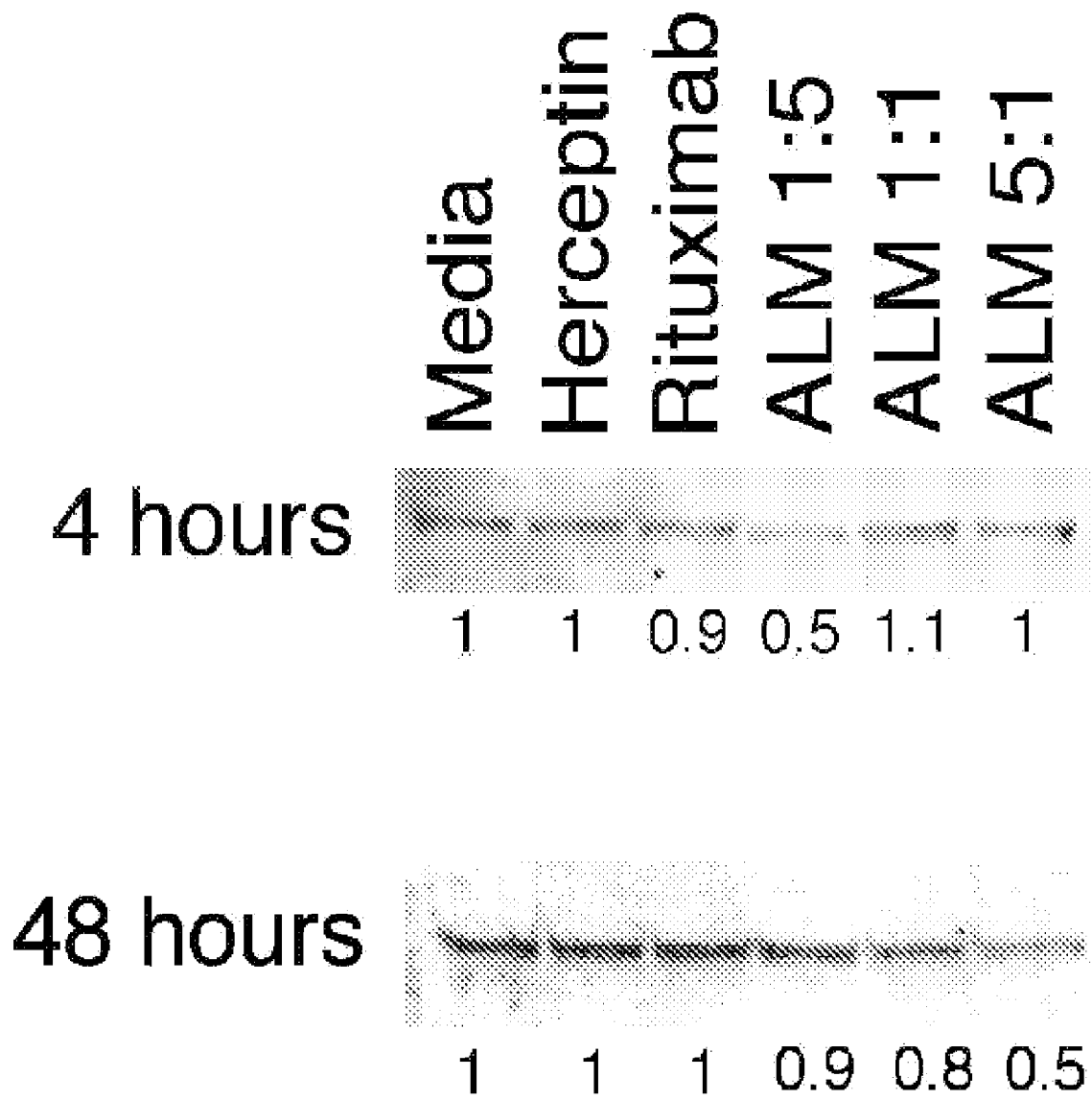
FIG. 8 shows a western blot analysis exhibiting alterations in phosphorylation of AKT over 48 hours following in vitro incubation of different concentrations of ALM with human BT-474 breast cancer cells expressing both HER2/neu and HER3.

ALM was evaluated in a series of in vitro and in vivo assays. Its ability to simultaneously bind to both HER3 and HER2/neu, individually and simultaneously, was demonstrated by surface plasmon resonance on a BIAcore instrument (FIGS. 2, 3 and 4). In vitro, incubation of ALM with human BT-474 breast cancer cells overexpressing both HER3 and HER2/neu lead to reduced cell surface expression of HER2/neu and HER 3 (FIG. 5), decreased proliferation in MTT assays (FIG. 6), reduced survival in a clonogenicity assay (FIG. 7) and increased phosphorylation followed by marked dephosphorylation of AKT2 (FIG. 8), an important protein in the apoptotic pathway. These effects were comparable (MTT assay) or greater (dephosphorylation of AKT2) than those observed using Herceptin[7] (data not shown).

Figure 9:
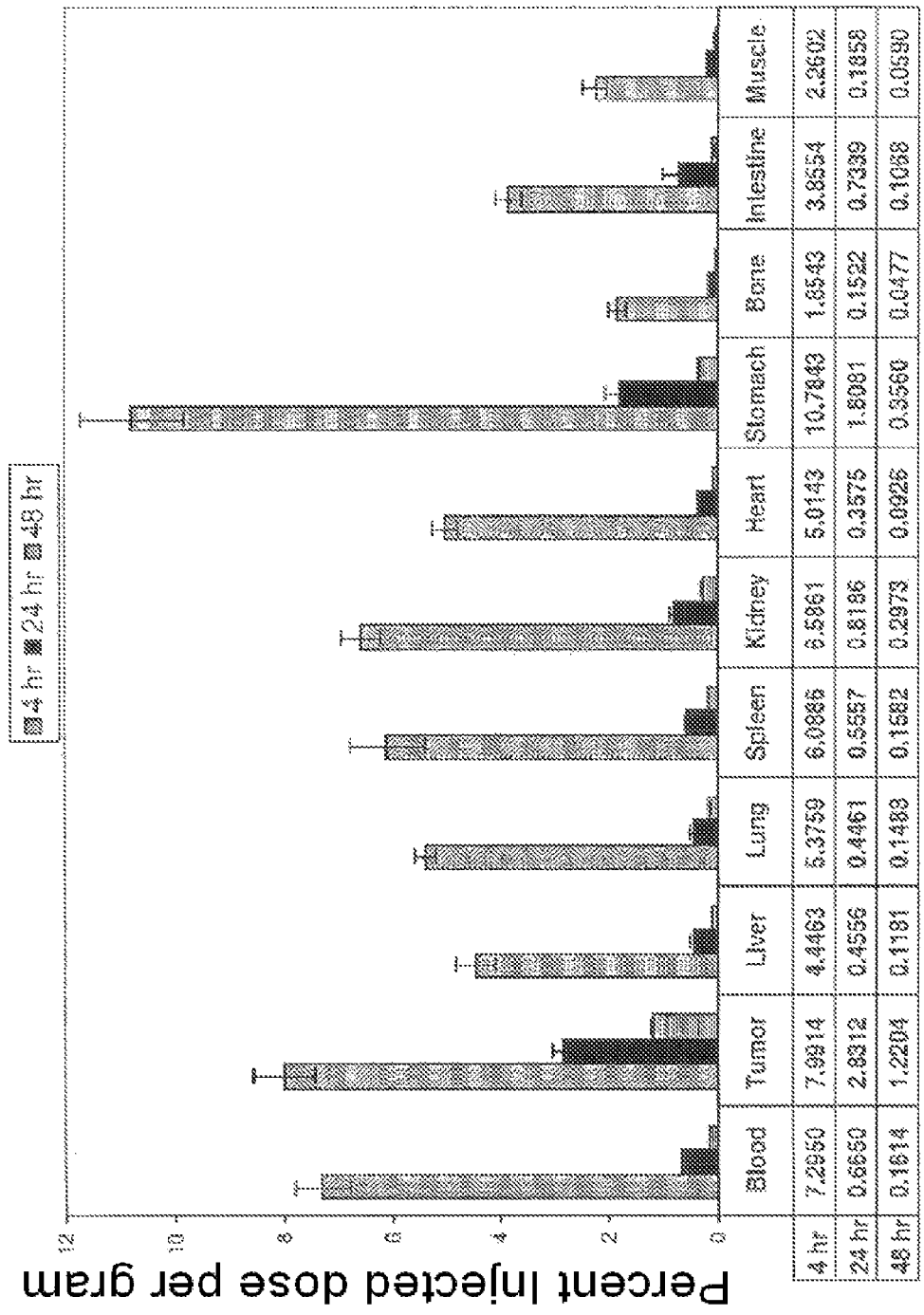
FIG. 9 shows a graph mapping the biodistribution of 1-labeled ALM over 48 hours in immunodeficient mice.

In vivo, radioiodinated ALM exhibited enhanced specific tumor targeting within 24 hours after administration to immunodeficient mice bearing s.c. human BT-474 tumor xenografts (FIG. 9).

These results demonstrate the utility of the bs-scFv antibody molecules of the invention for the treatment of tumor cells that overexpress EGFR proteins. The novel bs-scFv antibody molecules can be used alone or in combination with existing chemotherapeutic methods to treat a variety of cancers including, but not limited to breast, colon, ovarian, endometrial, gastric, pancreatic, prostate and salivary gland cancers.

Example 2

Combined Chemotherapeutic Approaches

HER2/neu is a compelling target for combined chemotherapy approaches as it is overexpressed in a variety of tumors and its overexpression has been correlated with a poor prognosis. While HER2/neu lacks a ligand that can trigger signaling through its tyrosine kinase domain, when overexpressed at high concentrations, HER2/neu can spontaneously form homodimers (Yarden and Sliwkowski (2001) *Nature Reviews, Molecular Cell Biology* 2: 127-137). HER3 is in many ways the opposite of HER2/neu. It actively binds to ligand but lacks a functional tyrosine kinase domain, thus requiring heterodimerization with HER2/neu for signaling. In fact, this combination is believed by many to be the most potent of the signaling complexes formed by the members of the EGFR family (Lohrisch and Piccart (2001) *Sem. Oncology* (28) Suppl 18: 3-11).

Many chemotherapeutic agents lead to damage that in a normal cell will trigger apoptosis. However, some tumor cells have aberrant signaling that interferes with the normal apoptosis signaling pathway. The phosphorylation of AKT2 in HER2/neu overexpressing tumor cells leads to an anti-apoptotic cascade that could interfere with the antitumor effects of chemotherapeutic or biological agents (Zhou et al. (2000) *J. Biol. Chem.*, 275: 8027-8031). Thus, targeting HER2/neu with bs-scFv antibody molecules in combination with existing chemotherapeutic treatments will be more effective in killing the tumor cells than chemotherapy alone.

Example 3

In Vivo Efficacy of $^{211}$At-Labeled Bispecific scFv

Figure 10:
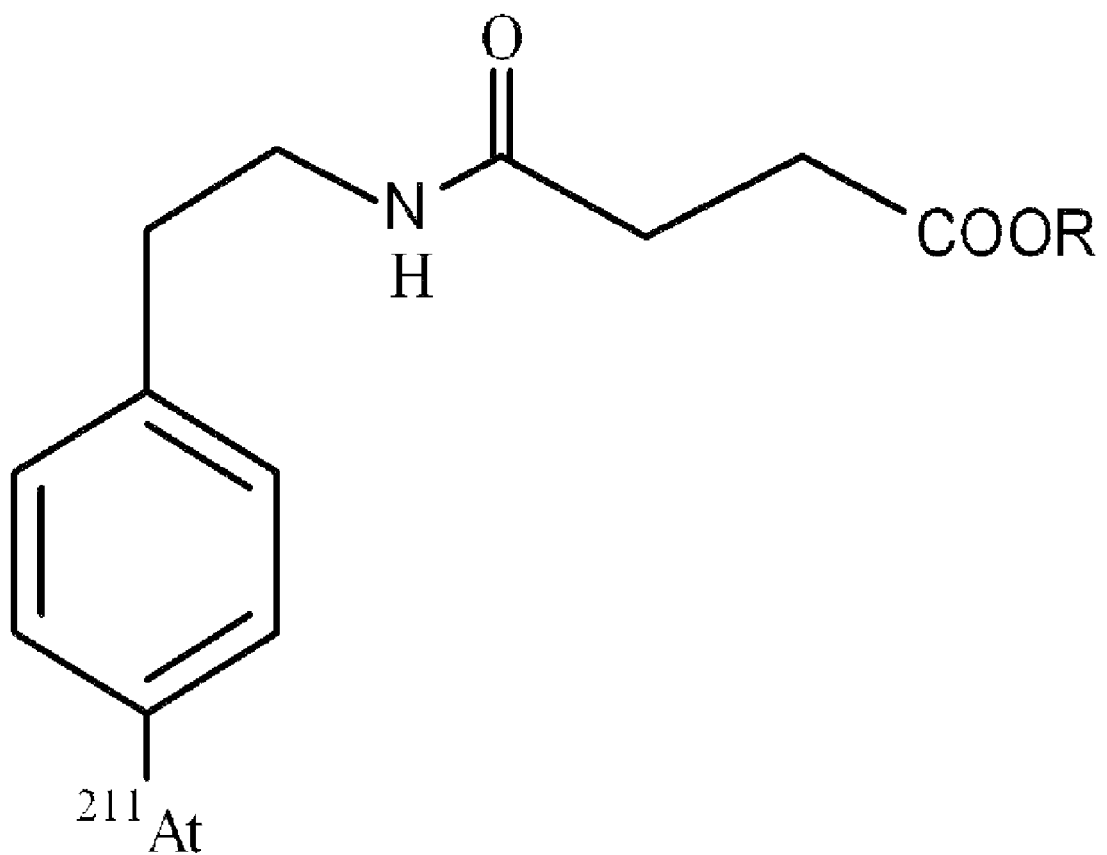
FIG. 10 illustrates a chelate $^{211}$At-SAPS used to label a bispecific antibody according to this invention.

An in vivo study was conducted to evaluate the efficacy of $^{211}$At labeled bispecific scFv against tumors. The bispecific antibody as labeled using $^{211}$At-SAPS chelate (N-(4-[$^{211}$At]astatophenethyl)succinimate) (see, e.g., FIG. 10).

Four days before injection of BT474 breast cancer cells, mice were implanted with a β-estradiol tablet. On day zero, the mice were injected with 5×10$^6$ BT474 breast cancer cells. On day 14, the first therapeutic dose of $^{211}$AT conjugated bispecific antibody (ALM) was administered i.p. at a high dose of 80 µg and at a low dose of 10 µg. Subsequent therapeutic doses were administered on day 16 and on day 18. Tumor volume was then tracked as shown in FIGS. 11A through 11C.

Figure 11A:
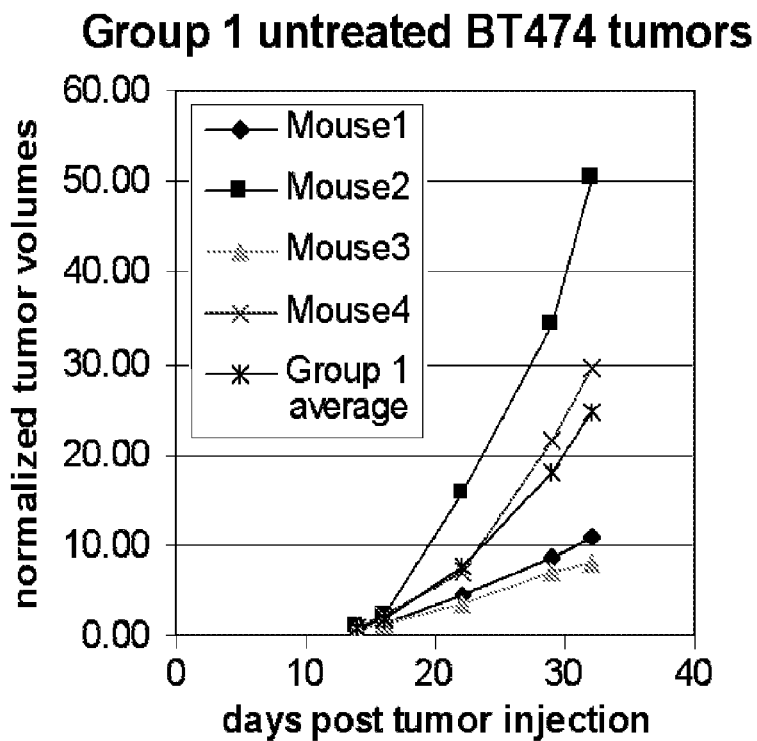
FIGS. 11A through 11C show the effects of $^{211}$At-conjugated ALM at low dosage of 10 µg (FIG. 11C) and at high a dose of 80 µg (FIG. 11B) as compared to untreated controls (FIG. 11A).
Figure 11B:
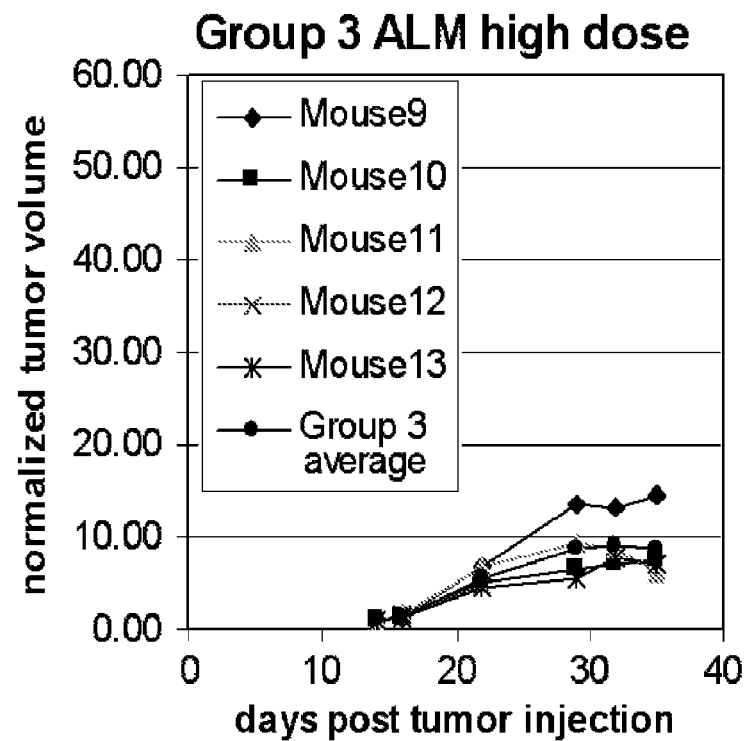
Figure 11C:
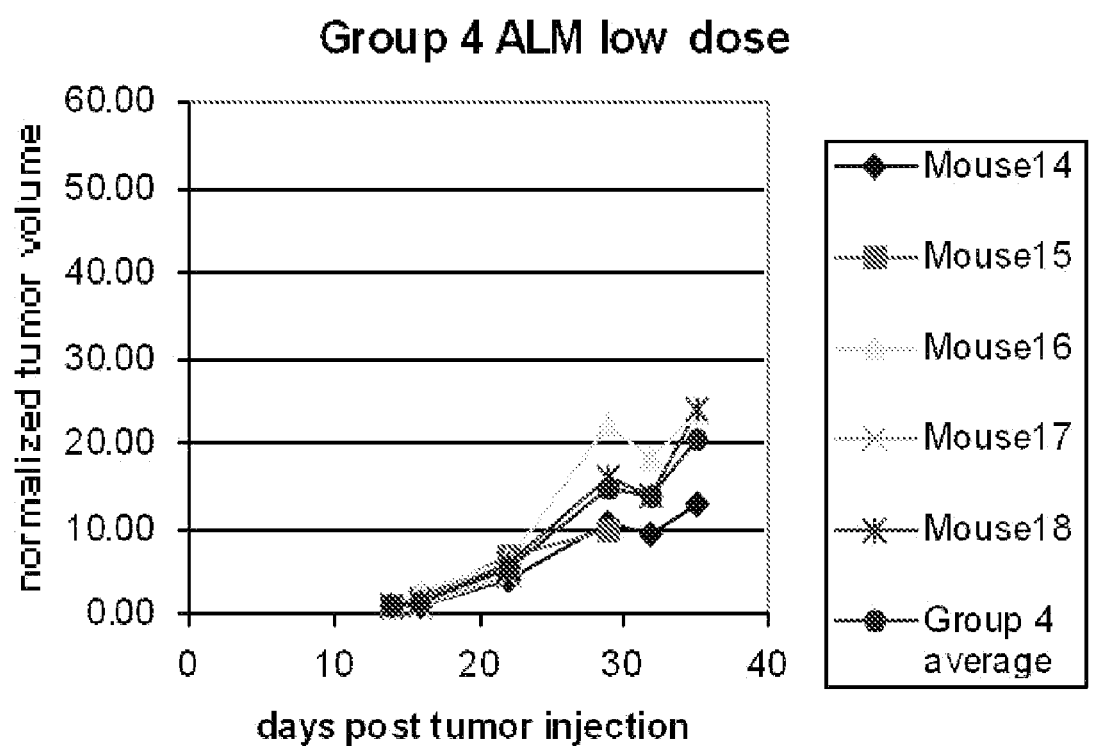

Tumor volume was generally lower in the treated animals (FIGS. 11B and 11C) as compared to the untreated control (FIG. 11A).

Example 4

Cancer Imaging

Figure 12:
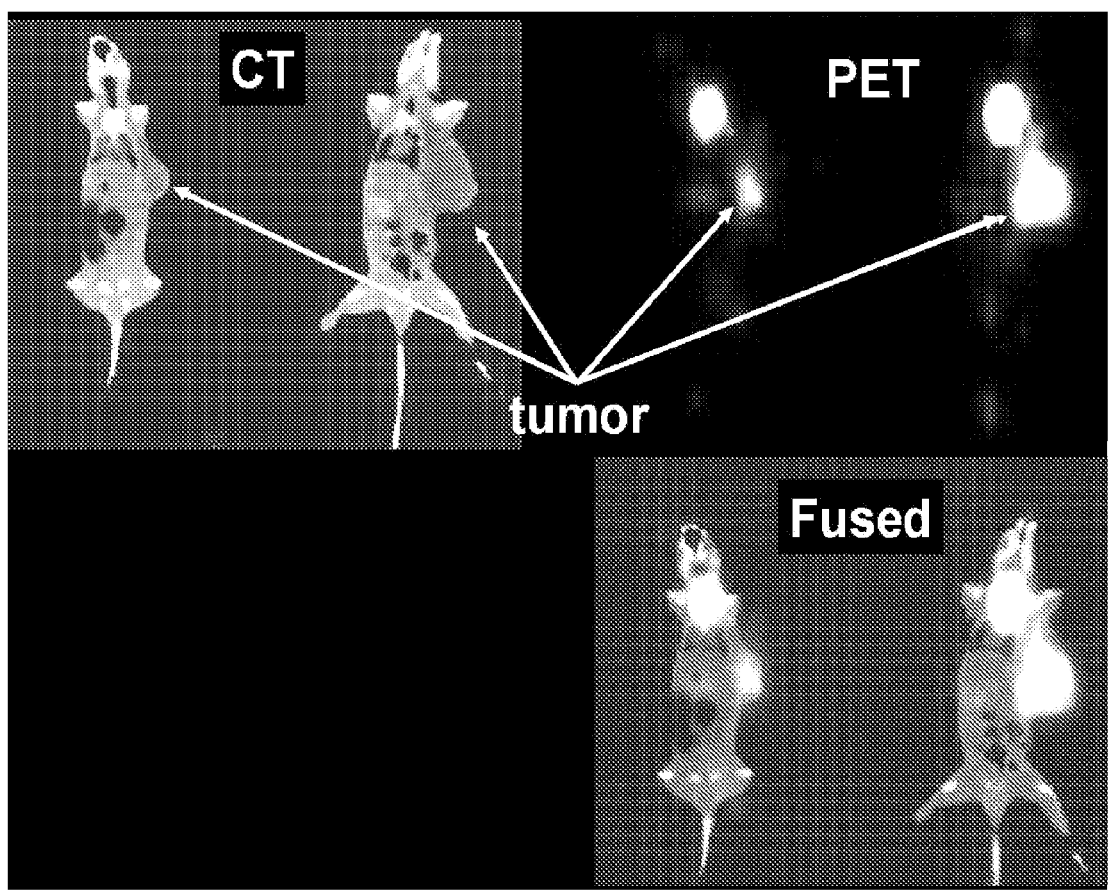
FIG. 12 illustrates specific tumor labeling in a mouse using a $^{124}$I-labeled bispecific antibody (ALM). PET (upper right) and CT (upper left) images of scid mice with SK-OV-3 ovarian carcinoma xenograft expressing HER2/neu and HER3 antigens and imaged 48 hours post-injection on a G.E. Discovery LS at FCCC. The CT slide thickness is 0.63 mm. Image fusion (lower right) performed with MIM software.

FIG. 12 shows a PET-CT image of two mice using Iodine-124 labeled ALM bispecific single-chain Fv. The mice were injected i.v. with 50 microCuries (50 micrograms) of labeled ALM and were imaged 48 hours later.

This should illustrates the efficacy of the bispecific antibodies of this invention for the detection of cancer.

It is understood that the examples and embodiments described herein are for illustrative purposes only and that various modifications or changes in light thereof will be suggested to persons skilled in the art and are to be included within the purview of this application and the scope of the appended claims. All publications, patents, and patent applications cited herein and accompanying appendices are hereby incorporated by reference in their entirety for all purposes.

---

What is claimed is:

1. A bispecific antibody comprising a first antibody joined to a second antibody, wherein:

said first antibody comprises a VH domain comprising the C6B1D2 VH CDR1 sequence SYWIA (SEQ ID NO:59), the C6B1D2 VH CDR2 sequence LIYPGDSDTKYSPSFQG (SEQ ID NO:60), and the C6B1D2 VH CDR3 sequence HDVGYCTDRTCAKWPEWLGV (SEQ ID NO:61); and a VL domain comprising C6B1D2 VL CDR1 sequence SGSSSNIGNNYVS (SEQ ID NO:62), the C6B1D2 VL CDR2 sequence DHTNRPA (SEQ ID NO:63), and the C6B1D2 VL CDR3 sequence ASWDYTLSGWV (SEQ ID NO:64); and said second antibody comprises three VH CDRs and three VL CDRs of an antibody selected from the group consisting of HER3.F4 (SEQ ID NO:2), HER3.H1 (SEQ ID NO:3), HER3.H3 (SEQ ID NO:4), HER3.E12 (SEQ ID NO:5), HER3.B12 (SEQ ID NO:6), EGFR.E12 (SEQ ID NO:7), EGFR.C10 (SEQ ID NO:8), EGFR.B11 (SEQ ID NO:9), EGFR.E8 (SEQ ID NO:10), HER4.B6 (SEQ ID NO:19), and C6B1D2 (SEQ ID NOs:52 and 57).

2. The bispecific antibody of claim 1, wherein said second antibody comprises:

a VH domain comprising the HER3.H3 VH CDR1 sequence SYWMS (SEQ ID NO:65), the HER3.H3 VH CDR2 sequence NINRDGSASYYVDSVKG (SEQ ID NO:66), and the HER3.H3 VH CDR3 sequence DRGVGYFDL (SEQ ID NO:67); and a VL domain comprising the HER3.H3 VL CDR1 sequence TGTSSDVGGYNFVS (SEQ ID NO:68), the HER3.H3 VL CDR2 sequence DVSDRPS (SEQ ID NO:69), and the HER3.H3 VL CDR3 sequence SSYGSSSTHVI (SEQ ID NO:70).

3. The bispecific antibody of claim 2, wherein said first antibody comprises:

a VH domain comprising a C6B1D2 framework 1 region comprising the sequence QVQLVQSGAEVKKPGESLKISCKGSGYSFT (SEQ ID NO:71) or QVQLLQSGAEVKKPGESLKISCKGSGYSFT (SEQ ID NO:72), a C6B1D2 framework 2 region comprising the sequence WVRQMPGKGLEYMG (SEQ ID NO:73), a C6B1D2 framework 3 region comprising the sequence QVTISVDKSVSTAYLQWSSLKPSDSAVYFCAR (SEQ ID NO:74), and a C6B1D2 framework 4 region comprising the sequence WGQGTLVTVSS (SEQ ID NO:75); and a VL domain comprising a C6B1D2 framework 1 region comprising the sequence QSVLTQPPSVSAAPGQKVTISC (SEQ ID NO:76) or ESVLTQPPSVSAAPGQKVTISC (SEQ ID NO:77), a C6B1D2 framework 2 region comprising the sequence WYQQLPGTAPKLLIY (SEQ ID NO:78), a C6B1D2 framework 3 region comprising the sequence GVPDRFSGSKSGTSASLAISGFRSEDEADYYC (SEQ ID NO:79); and a C6B1D2 framework 4 region comprising the sequence FGGGTKVTVLG (SEQ ID NO:80) or FGGGTKLTVLG (SEQ ID NO:81).

4. The bispecific antibody of claim 2, wherein said first antibody is a attached to said second antibody by a linker.

5. The bispecific antibody of claim 2, wherein said first antibody is a single chain antibody and said second antibody is a single chain antibody.

6. The bispecific antibody of claim 2, wherein said first antibody is a single chain Fv antibody.

7. The bispecific antibody of claim 2, wherein said second antibody is a single chain FV antibody.

8. The bispecific antibody of claim 5, wherein said first antibody is a single chain Fv antibody and said second antibody is a single chain Fv.

9. The bispecific antibody of claim 8, wherein said first antibody is attached to said second antibody by a peptide linker.

10. A composition comprising the bispecific antibody according to any one of claims 1-4, 7-8, and 9 and a pharmaceutically acceptable carrier.

11. The composition of claim 10, wherein said composition is formulated for injection.

12. The composition of claim 11, wherein said composition is formulated for intravenous injection.

13. The composition of claim 11, wherein said composition is in unit dosage form.

14. The composition of claim 12, wherein said composition is in unit dosage form.

15. A method for treating a cancer that overexpresses HER2 and/or HER3 proteins, said method comprising administering to a patient in need thereof a therapeutically effective amount of the bispecific antibody comprising a first single chain Fv antibody that binds HER2/neu and a second single chain Fv antibody that binds HER3, wherein said first antibody comprises a heavy chain variable domain comprising all three VH CDRs of the antibody B1D2 VH domain (SEQ ID NO:42) and a light chain variable (VL) domain comprising all three VL CDRs of the antibody B1D2 VL domain (SEQ ID NO:47), and said second antibody comprises a heavy chain variable domain comprising all three VH CDRs of antibody HER3.H3 (SEQ ID NO:4) and a light chain variable (VL) domain comprising all three CDRs of antibody HER3.H3 (SEQ ID NO:4).

16. The method of claim 15, wherein the cancer is selected from the group consisting of breast, colon, ovarian, endometrial, gastric, pancreatic, prostate, and salivary gland cancer.

17. The method of claim 16, wherein the cancer is breast cancer or gastric cancer.

* * * * *

UNITED STATES PATENT AND TRADEMARK OFFICE
CERTIFICATE OF CORRECTION

PATENT NO. : 8,329,873 B2
APPLICATION NO. : 11/943367
DATED : December 11, 2012
INVENTOR(S) : Adams et al.

It is certified that error appears in the above-identified patent and that said Letters Patent is hereby corrected as shown below:

IN THE SPECIFICATION

Column 1, lines 20-26, delete "This work was supported in part by a Grant from the United States Army Medical Research and Material Command Breast Cancer Research Program, Grant No: DAMD 17-01-1-0520, and The United States National Cancer Institute, Institutional Pilot Grant No: NCI CA06927. The government of the United States of America may have certain rights in this invention." and insert -- This invention was made with government support under grant no. CA06927 awarded by the National Institutes of Health (NCI) and grant no. DAMD17-01-1-0520 awarded by the United States Army Medical Research and Materiel Command. The government has certain rights in the invention. --.

Signed and Sealed this
Seventh Day of January, 2014

Margaret A. Focarino
*Commissioner for Patents of the United States Patent and Trademark Office*

SEQUENCE LISTING

```
<160> NUMBER OF SEQ ID NOS: 81

<210> SEQ ID NO 1
<211> LENGTH: 291
<212> TYPE: PRT
<213> ORGANISM: Artificial
<220> FEATURE:
<223> OTHER INFORMATION: Synthetic antibody.

<400> SEQUENCE: 1

Met Lys Tyr Leu Leu Pro Thr Ala Ala Ala Gly Leu Leu Leu Leu Ala
1               5                   10                  15

Ala Gln Pro Ala Met Ala Gln Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Arg Ser Tyr Ala Met Ser Trp Val Arg Gln Ala Pro Gly
    50                  55                  60

Lys Gly Leu Glu Trp Val Ser Ala Ile Ser Gly Arg Gly Asp Asn Thr
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Lys Met Thr Ser Asn Ala Phe Ala Phe
        115                 120                 125

Asp Tyr Trp Gly Gln Gly Thr Leu Val Thr Val Ser Ser Gly Gly Gly
```

```
                130                 135                 140
Gly Ser Gly Gly Gly Ser Gly Gly Gly Ser Gln Ser Val Leu
145                 150                 155                 160

Thr Gln Pro Pro Ser Val Ser Gly Ala Pro Gly Gln Arg Val Thr Ile
                    165                 170                 175

Ser Cys Thr Gly Ser Ser Ser Asn Ile Gly Ala Gly Tyr Gly Val His
                180                 185                 190

Trp Tyr Gln Gln Leu Pro Gly Thr Ala Pro Lys Leu Leu Ile Tyr Gly
            195                 200                 205

Asn Thr Asn Arg Pro Ser Gly Val Pro Asp Arg Phe Ser Gly Phe Lys
210                 215                 220

Ser Gly Thr Ser Ala Ser Leu Ala Ile Thr Gly Leu Gln Ala Glu Asp
225                 230                 235                 240

Glu Ala Asp Tyr Tyr Cys Gln Ser Tyr Asp Ser Ser Leu Ser Gly Trp
                245                 250                 255

Val Phe Gly Gly Gly Thr Lys Leu Thr Val Leu Gly Ala Ala Ala Glu
            260                 265                 270

Gln Lys Leu Ile Ser Glu Glu Asp Leu Asn Gly Ala Ala His His His
        275                 280                 285

His His His
    290

<210> SEQ ID NO 2
<211> LENGTH: 291
<212> TYPE: PRT
<213> ORGANISM: Artificial
<220> FEATURE:
<223> OTHER INFORMATION: Synthetic antibody.

<400> SEQUENCE: 2

Met Lys Tyr Leu Leu Pro Thr Ala Ala Ala Gly Leu Leu Leu Leu Ala
1               5                   10                  15

Ala Gln Pro Ala Met Ala Gln Val Gln Leu Val Glu Ser Gly Gly Gly
                20                  25                  30

Leu Val Gln Pro Gly Gly Ser Leu Arg Leu Ser Cys Ala Ala Ser Gly
            35                  40                  45

Phe Thr Phe Arg Ser Tyr Ala Met Ser Trp Val Arg Gln Ala Pro Gly
        50                  55                  60

Lys Gly Leu Glu Trp Val Ser Ala Ile Ser Gly Arg Gly Asp Asn Thr
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Lys Met Thr Ser Asn Ala Phe Ala Phe
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Ser Gln Ser Val Leu
145                 150                 155                 160

Thr Gln Pro Pro Ser Val Ser Gly Ala Pro Gly Gln Arg Val Thr Ile
                165                 170                 175

Ser Cys Thr Gly Ser Ser Ser Asn Ile Gly Ala Gly Tyr Gly Val His
            180                 185                 190

Trp Tyr Gln Gln Leu Pro Gly Thr Ala Pro Lys Leu Leu Ile Tyr Gly
        195                 200                 205
```

Asn Thr Asn Arg Pro Ser Gly Val Pro Asp Arg Phe Ser Gly Phe Lys
    210                 215                 220

Ser Gly Thr Ser Ala Ser Leu Ala Ile Thr Gly Leu Gln Ala Glu Asp
225                 230                 235                 240

Glu Ala Asp Tyr Tyr Cys Gln Ser Tyr Asp Ser Ser Leu Ser Gly Trp
                245                 250                 255

Val Phe Gly Gly Gly Thr Lys Leu Thr Val Leu Gly Ala Ala Ala Glu
            260                 265                 270

Gln Lys Leu Ile Ser Glu Glu Asp Leu Asn Gly Ala Ala His His His
        275                 280                 285

His His His
    290

<210> SEQ ID NO 3
<211> LENGTH: 288
<212> TYPE: PRT
<213> ORGANISM: Artificial
<220> FEATURE:
<223> OTHER INFORMATION: Synthetic antibody.

<400> SEQUENCE: 3

Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Ser Gly Gly Gly
            20                  25                  30

Leu Val Lys Pro Gly Gly Ser Leu Arg Leu Ser Cys Ala Ala Ser Gly
        35                  40                  45

Phe Thr Phe Ser Ser Tyr Ser Met Asn Trp Val Arg Gln Val Pro Gly
    50                  55                  60

Lys Gly Leu Glu Trp Val Ser Ser Ile Ser Ser Ser Ser Tyr Ile
65                  70                  75                  80

Tyr Tyr Ala Asp Ser Val Lys Gly Arg Phe Thr Ile Ser Arg Asp Asn
                85                  90                  95

Ala Lys Asn Ser Leu Tyr Leu Gln Met Asn Ser Leu Arg Asp Glu Asp
            100                 105                 110

Thr Ala Val Tyr Tyr Cys Ala Arg Asp Asp Gly Pro Pro Ile Gln His
        115                 120                 125

Trp Gly Gln Gly Thr Leu Val Thr Val Ser Ser Arg Gly Gly Gly Ser
    130                 135                 140

Gly Gly Gly Gly Ser Gly Gly Gly Ser Gln Ser Val Leu Ser Gln
145                 150                 155                 160

Pro Pro Ser Val Ser Gly Ala Pro Gly Gln Arg Val Thr Ile Ser Cys
                165                 170                 175

Thr Gly Ser Ser Ser Asn Ile Gly Ala Ser Phe Asp Val Gln Trp Tyr
            180                 185                 190

Gln Gln Leu Pro Gly Thr Ala Pro Lys Leu Leu Ile Tyr Gly Asn Asn
        195                 200                 205

Asn Arg Pro Ser Gly Val Pro Asp Arg Phe Ser Ala Ser Lys Ser Gly
    210                 215                 220

Thr Ser Ala Ser Leu Gly Ile Thr Gly Leu Gln Ile Gly Asp Glu Ala
225                 230                 235                 240

Asp Tyr Tyr Cys Gly Ser Tyr Thr Gly Thr Tyr Ser Trp Val Phe Gly
                245                 250                 255

Gly Gly Thr Lys Val Thr Val Leu Gly Ala Ala Ala Glu Gln Lys Leu
            260                 265                 270

```
Ile Ser Glu Glu Asp Leu Asn Gly Ala Ala His His His His His
        275                 280                 285

<210> SEQ ID NO 4
<211> LENGTH: 290
<212> TYPE: PRT
<213> ORGANISM: Artificial
<220> FEATURE:
<223> OTHER INFORMATION: Synthetic antibody.

<400> SEQUENCE: 4

Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Glu Ser Gly Gly Gly
            20                  25                  30

Leu Val Lys Pro Gly Gly Ser Leu Arg Leu Ser Cys Ala Ala Ser Gly
        35                  40                  45

Phe Thr Phe Ser Ser Tyr Trp Met Ser Trp Val Arg Gln Ala Pro Gly
    50                  55                  60

Lys Gly Leu Glu Trp Val Ala Asn Ile Asn Arg Asp Gly Ser Ala Ser
65                  70                  75                  80

Tyr Tyr Val Asp Ser Val Lys Gly Arg Phe Thr Ile Ser Arg Asp Asp
                85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Asp Arg Gly Val Gly Tyr Phe Asp
        115                 120                 125

Leu Trp Gly Arg Gly Thr Leu Val Thr Val Ser Ser Gly Gly Gly Gly
    130                 135                 140

Ser Gly Gly Gly Gly Ser Gly Gly Gly Gly Ser Gln Ser Ala Leu Thr
145                 150                 155                 160

Gln Pro Ala Ser Val Ser Gly Ser Pro Gly Gln Ser Ile Thr Ile Ser
                165                 170                 175

Cys Thr Gly Thr Ser Ser Asp Val Gly Gly Tyr Asn Phe Val Ser Trp
            180                 185                 190

Tyr Gln Gln His Pro Gly Lys Ala Pro Lys Leu Met Ile Tyr Asp Val
        195                 200                 205

Ser Asp Arg Pro Ser Gly Val Ser Asp Arg Phe Ser Gly Ser Lys Ser
    210                 215                 220

Gly Asn Thr Ala Ser Leu Ile Ile Ser Gly Leu Gln Ala Asp Asp Glu
225                 230                 235                 240

Ala Asp Tyr Tyr Cys Ser Ser Tyr Gly Ser Ser Thr His Val Ile
                245                 250                 255

Phe Gly Gly Gly Thr Lys Val Thr Val Leu Gly Ala Ala Ala Glu Gln
            260                 265                 270

Lys Leu Ile Ser Glu Glu Asp Leu Asn Gly Ala Ala His His His His
        275                 280                 285

His His
    290

<210> SEQ ID NO 5
<211> LENGTH: 287
<212> TYPE: PRT
<213> ORGANISM: Artificial
<220> FEATURE:
<223> OTHER INFORMATION: Synthetic antibody.

<400> SEQUENCE: 5
```

-continued

Met Lys Tyr Leu Leu Pro Thr Ala Ala Gly Leu Leu Leu Ala
1               5                   10                  15

Ala Gln Pro Ala Met Ala Gln Val Gln Leu Val Glu Ser Gly Gly
            20                  25                  30

Val Val Gln Pro Gly Arg Ser Leu Arg Leu Ser Cys Ala Ala Ser Gly
        35                  40                  45

Phe Thr Phe Ser Asp Tyr Tyr Ile His Trp Val Arg Gln Ala Pro Gly
    50                  55                  60

Lys Gly Leu Glu Trp Met Ala Val Ile Ser Tyr Asp Gly Asn Asn Lys
65                  70                  75                  80

Tyr Tyr Ala Ala Ser Val Lys Asp Arg Phe Thr Ile Ser Arg Asp Asn
                85                  90                  95

Ser Lys Asn Thr Val Ser Leu Gln Met Asn Ser Leu Arg Ala Glu Asp
            100                 105                 110

Thr Ala Val Tyr Tyr Cys Ala Arg Asp Leu Tyr Gly Asp Tyr Ala Leu
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Asp Ile Gln Met
145                 150                 155                 160

Thr Gln Ser Pro Ser Thr Leu Ser Ala Ser Leu Gly Asp Arg Val Thr
                165                 170                 175

Ile Thr Cys Arg Ala Ser Gln Ser Ile Gly Ser Trp Leu Ala Trp Tyr
            180                 185                 190

Gln Gln Lys Pro Gly Lys Ala Pro Lys Leu Leu Ile Tyr Lys Ala Ser
        195                 200                 205

Thr Leu Glu Ser Gly Val Pro Ser Arg Phe Thr Gly Ser Gly Ser Gly
    210                 215                 220

Thr Glu Phe Thr Leu Thr Ile Ser Gly Leu Gln Pro Glu Asp Phe Ala
225                 230                 235                 240

Thr Tyr Tyr Cys Gln Lys Leu Ser Ser Tyr Pro Leu Thr Phe Gly Gly
                245                 250                 255

Gly Thr Lys Val Glu Ile Lys Arg Ala Ala Ala Glu Gln Lys Leu Ile
            260                 265                 270

Ser Glu Glu Asp Leu Asn Gly Ala Ala His His His His His His
        275                 280                 285

<210> SEQ ID NO 6
<211> LENGTH: 291
<212> TYPE: PRT
<213> ORGANISM: Artificial
<220> FEATURE:
<223> OTHER INFORMATION: Synthetic antibody.

<400> SEQUENCE: 6

Met Lys Tyr Leu Leu Pro Thr Ala Ala Ala Gly Leu Leu Leu Leu Ala
1               5                   10                  15

Ala Gln Pro Ala Met Ala Gln Val Gln Leu Val Gln Ser Gly Gly Gly
            20                  25                  30

Leu Val Gln Pro Gly Arg Ser Leu Arg Leu Ser Cys Ala Ala Ser Gly
        35                  40                  45

Phe Thr Phe Asp Asp Tyr Ala Met His Trp Val Arg Gln Ala Pro Gly
    50                  55                  60

Lys Gly Leu Glu Trp Val Ser Gly Ile Ser Trp Asn Ser Gly Ser Ile
65                  70                  75                  80

Gly Tyr Ala Asp Ser Val Lys Gly Arg Phe Thr Ile Ser Arg Asp Asn

```
                85                  90                  95
Ala Lys Asn Ser Leu Tyr Leu Gln Met Asn Ser Leu Arg Pro Glu Asp
            100                 105                 110

Thr Ala Val Tyr Tyr Cys Ala Arg Asp Leu Gly Ala Lys Gln Trp Leu
            115                 120                 125

Glu Gly Phe Asp Tyr Trp Gly Gln Gly Thr Leu Val Thr Val Ser Ser
            130                 135                 140

Gly Gly Gly Gly Ser Gly Gly Gly Ser Gly Gly Gly Gly Ser Asn
145                 150                 155                 160

Phe Met Leu Thr Gln Asp Pro Ala Val Ser Val Ala Leu Gly Gln Thr
                165                 170                 175

Val Arg Ile Thr Cys Gln Gly Asp Ser Leu Arg Ser Tyr Tyr Ala Ser
                180                 185                 190

Trp Tyr Gln Gln Lys Pro Gly Gln Ala Pro Val Leu Val Ile Tyr Gly
                195                 200                 205

Lys Asn Asn Arg Pro Ser Gly Ile Pro Asp Arg Phe Ser Gly Ser Thr
    210                 215                 220

Ser Gly Asn Ser Ala Ser Leu Thr Ile Thr Gly Ala Gln Ala Glu Asp
225                 230                 235                 240

Glu Ala Asp Tyr Tyr Cys Asn Ser Arg Asp Ser Ser Gly Asn His Trp
                    245                 250                 255

Val Phe Gly Gly Gly Thr Lys Val Thr Val Leu Gly Ala Ala Ala Glu
                260                 265                 270

Gln Lys Leu Ile Ser Glu Glu Asp Leu Asn Gly Ala Ala His His His
            275                 280                 285

His His His
        290

<210> SEQ ID NO 7
<211> LENGTH: 295
<212> TYPE: PRT
<213> ORGANISM: Artificial
<220> FEATURE:
<223> OTHER INFORMATION: Synthetic antibody.

<400> SEQUENCE: 7

Met Lys Tyr Leu Leu Pro Thr Ala Ala Ala Gly Leu Leu Leu Leu Ala
1               5                   10                  15

Ala Gln Pro Ala Met Ala Glu Val Gln Leu Val Gln Ser Gly Ala Glu
            20                  25                  30

Val Lys Lys Pro Gly Ser Ser Val Lys Val Ser Cys Lys Ala Ser Gly
        35                  40                  45

Gly Thr Phe Ser Ser Tyr Ala Ile Ser Trp Val Arg Gln Ala Pro Gly
    50                  55                  60

Gln Gly Leu Glu Trp Met Gly Gly Ile Ile Pro Ile Phe Gly Thr Ala
65                  70                  75                  80

Asn Tyr Ala Gln Lys Phe Gln Gly Arg Val Thr Ile Thr Ala Asp Glu
                85                  90                  95

Ser Thr Ser Thr Ala Tyr Met Glu Val Ser Ser Leu Arg Ser Glu Asp
            100                 105                 110

Thr Ala Val Tyr Tyr Cys Ala Arg Glu Glu Gly Pro Tyr Cys Ser Ser
            115                 120                 125

Thr Ser Cys Tyr Gly Ala Phe Asp Ile Trp Gly Gln Gly Thr Leu Val
        130                 135                 140

Thr Val Ser Ser Gly Gly Gly Gly Ser Gly Gly Gly Gly Ser Gly Gly
145                 150                 155                 160
```

```
Gly Gly Ser Gln Ser Val Leu Thr Gln Asp Pro Ala Val Ser Val Ala
                165                 170                 175

Leu Gly Gln Thr Val Lys Ile Thr Cys Gln Gly Asp Ser Leu Arg Ser
            180                 185                 190

Tyr Phe Ala Ser Trp Tyr Gln Lys Pro Gly Gln Ala Pro Thr Leu
        195                 200                 205

Val Met Tyr Ala Arg Asn Asp Arg Pro Ala Gly Val Pro Asp Arg Phe
210                 215                 220

Ser Gly Ser Lys Ser Gly Thr Ser Ala Ser Leu Ala Ile Ser Gly Leu
225                 230                 235                 240

Gln Ser Glu Asp Glu Ala Asp Tyr Tyr Cys Ala Ala Trp Asp Asp Ser
                245                 250                 255

Leu Asn Gly Tyr Leu Phe Gly Ala Gly Thr Lys Leu Thr Val Leu Gly
                260                 265                 270

Ala Ala Ala Glu Gln Lys Leu Ile Ser Glu Glu Asp Leu Asn Gly Ala
                275                 280                 285

Ala His His His His His His
                290                 295

<210> SEQ ID NO 8
<211> LENGTH: 286
<212> TYPE: PRT
<213> ORGANISM: Artificial
<220> FEATURE:
<223> OTHER INFORMATION: Synthetic antibody.

<400> SEQUENCE: 8

Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Glu Ser Gly Pro Gly
                20                  25                  30

Leu Val Lys Pro Ser Glu Thr Leu Ser Leu Thr Cys Thr Val Ser Gly
            35                  40                  45

Gly Ser Phe Arg Ser Tyr Tyr Trp Ser Trp Ile Arg Pro Pro Gly Lys
    50                  55                  60

Gly Leu Glu Trp Ile Gly Tyr Ile Phe Tyr Ser Gly Ser Thr Asn Tyr
65                  70                  75                  80

Asn Pro Ser Leu Lys Ser Arg Val Thr Ile Ser Val Asp Thr Ser Lys
                85                  90                  95

Asn Gln Phe Ser Leu Lys Leu Ser Ser Leu Thr Ala Ala Asp Thr Ala
                100                 105                 110

Val Tyr Tyr Cys Ala Arg Gly His Leu Gly Glu Leu Gly Trp Phe Asp
            115                 120                 125

Pro Trp Gly Gln Gly Thr Leu Val Thr Val Ser Ser Ser Gly Gly Gly
        130                 135                 140

Ser Gly Gly Gly Gly Ser Gly Gly Gly Ser Asp Ile Gln Met Thr
145                 150                 155                 160

Gln Ser Pro Ser Ser Leu Ser Ala Ser Val Gly Asp Arg Val Thr Ile
                165                 170                 175

Thr Cys Gln Ala Ser Gln Asp Ile Ser Asn Tyr Leu Asn Trp Tyr Gln
            180                 185                 190

Gln Lys Pro Gly Lys Ala Pro Lys Leu Leu Ile Phe Ala Ala Ser Arg
        195                 200                 205

Leu Ala Ser Gly Val Pro Ser Arg Phe Ser Gly Ser Gly Ser Gly Thr
    210                 215                 220
```

```
Asp Phe Ser Leu Thr Ile Ser Ser Leu Gln Pro Asp Asp Phe Ala Thr
225                 230                 235                 240

Tyr Tyr Cys Leu Gln Asp Ser Asp Tyr Pro Leu Thr Phe Gly Gly Gly
                245                 250                 255

Thr Lys Val Glu Ile Lys Arg Ala Ala Ala Glu Gln Lys Leu Ile Ser
            260                 265                 270

Glu Glu Asp Leu Asn Gly Ala Ala His His His His His His
            275                 280                 285
```

<210> SEQ ID NO 9
<211> LENGTH: 291
<212> TYPE: PRT
<213> ORGANISM: Artificial
<220> FEATURE:
<223> OTHER INFORMATION: Synthetic antibody.

<400> SEQUENCE: 9

```
Met Lys Tyr Leu Leu Pro Thr Ala Ala Ala Gly Leu Leu Leu Leu Ala
1               5                   10                  15

Ala Gln Pro Ala Met Ala Gln Val Gln Leu Leu Gln Phe Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Ala Met Ser Trp Val Arg Gln Ala Pro Gly
    50                  55                  60

Lys Gly Leu Glu Trp Leu Ser Ala Ile Ser Gly Ser Gly Gly Ser Thr
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Glu Gly Tyr Ser Ser Asn Trp Asn
        115                 120                 125

Asn Trp Tyr Phe Asp Leu Trp Gly Arg Gly Thr Leu Val Thr Val Ser
    130                 135                 140

Ser Gly Gly Gly Gly Ser Gly Gly Gly Gly Ser Gly Gly Gly Gly Ser
145                 150                 155                 160

Asp Val Val Met Thr Gln Ser Pro Ser Ser Leu Ser Ala Ser Val Gly
                165                 170                 175

Asp Arg Val Thr Ile Thr Cys Arg Ala Ser Gln Ser Ile Ser Ser Tyr
            180                 185                 190

Leu Asn Trp Tyr Gln Gln Lys Pro Gly Lys Ala Pro Glu Leu Leu Ile
        195                 200                 205

Tyr Ala Ala Ser Arg Leu Gln Ser Gly Val Pro Ser Arg Phe Ser Gly
    210                 215                 220

Ser Gly Ser Gly Thr Glu Phe Thr Leu Thr Ile Ser Ser Leu Gln Pro
225                 230                 235                 240

Asp Asp Phe Ala Thr Tyr Tyr Gly Gln Gln Tyr Tyr Asn Tyr Pro Trp
                245                 250                 255

Thr Phe Gly Arg Gly Thr Lys Val Glu Ile Lys Arg Ala Ala Ala Glu
            260                 265                 270

Gln Lys Leu Ile Ser Glu Glu Asp Leu Asn Gly Ala Ala His His His
        275                 280                 285

His His His
        290
```

```
<210> SEQ ID NO 10
<211> LENGTH: 291
<212> TYPE: PRT
<213> ORGANISM: Artificial
<220> FEATURE:
<223> OTHER INFORMATION: Synthetic antibody.

<400> SEQUENCE: 10

Met Lys Tyr Leu Leu Pro Thr Ala Ala Gly Leu Leu Leu Leu Ala
1               5                   10                  15

Ala Gln Pro Ala Met Ala Gln Val Gln Leu Gln Glu Ser Gly Gly
                20                  25                  30

Met Val Gln Pro Gly Arg Ser Leu Arg Leu Ser Cys Ala Ala Ser
                35                  40                  45

Phe Thr Phe Ser Ser Tyr Ala Met Ser Trp Val Arg Gln Ala Pro Gly
    50                  55                  60

Lys Gly Leu Glu Trp Val Ser Ala Ile Ser Gly Ser Gly Gly Ser Thr
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
                100                 105                 110

Thr Ala Leu Tyr Tyr Cys Ala Arg Glu Gly Tyr Ser Ser Asn Trp Asn
                115                 120                 125

Asn Trp Tyr Phe Asp Leu Trp Gly Arg Gly Thr Leu Val Thr Val Ser
    130                 135                 140

Ser Gly Gly Gly Gly Ser Gly Gly Gly Gly Ser Gly Gly Gly Gly Ser
145                 150                 155                 160

Glu Ile Val Leu Thr Gln Ser Pro Ser Ser Leu Ser Ala Ser Val Gly
                165                 170                 175

Asp Arg Val Thr Ile Thr Cys Arg Ala Ser Gln Ser Ile Ser Ser Tyr
                180                 185                 190

Leu Asn Trp Tyr Gln Gln Lys Pro Gly Lys Ala Pro Lys Leu Leu Ile
    195                 200                 205

Tyr Ala Ala Ser Ser Leu Gln Ser Gly Val Pro Ser Arg Phe Ser Gly
    210                 215                 220

Ser Gly Ser Gly Thr Asp Phe Thr Leu Thr Ile Ser Ser Leu Gln Pro
225                 230                 235                 240

Asp Asp Phe Ala Thr Tyr Tyr Cys Gln Gln Tyr Asn Ser Tyr Pro Trp
                245                 250                 255

Thr Phe Gly Gln Gly Thr Lys Leu Glu Ile Lys Arg Ala Ala Ala Glu
                260                 265                 270

Gln Lys Leu Ile Ser Glu Glu Asp Leu Asn Gly Ala Ala His His His
                275                 280                 285

His His His
    290

<210> SEQ ID NO 11
<211> LENGTH: 5
<212> TYPE: PRT
<213> ORGANISM: Artificial
<220> FEATURE:
<223> OTHER INFORMATION: Peptide linker.

<400> SEQUENCE: 11

Gly Gly Gly Gly Ser
1               5
```

```
<210> SEQ ID NO 12
<211> LENGTH: 55
<212> TYPE: DNA
<213> ORGANISM: Artificial
<220> FEATURE:
<223> OTHER INFORMATION: Olidonucleotide primer.

<400> SEQUENCE: 12
aattcaggtg ctggtacttc aggttcaggt gcttcaggtg aaggttcagg ttcaa       55

<210> SEQ ID NO 13
<211> LENGTH: 55
<212> TYPE: DNA
<213> ORGANISM: Artificial
<220> FEATURE:
<223> OTHER INFORMATION: Olidonucleotide primer.

<400> SEQUENCE: 13
agctttgaac ctgaaccttc acctgaagca cctgaacctg aagtaccagc acctg       55

<210> SEQ ID NO 14
<211> LENGTH: 60
<212> TYPE: DNA
<213> ORGANISM: Artificial
<220> FEATURE:
<223> OTHER INFORMATION: Olidonucleotide primer.

<400> SEQUENCE: 14
aattcaggtg ctggtacttc aggttcaggt gcttcaggtg aaggttcagg ttcaaagcta  60

<210> SEQ ID NO 15
<211> LENGTH: 29
<212> TYPE: DNA
<213> ORGANISM: Artificial
<220> FEATURE:
<223> OTHER INFORMATION: Olidonucleotide primer.

<400> SEQUENCE: 15
cgaccatggc ccaggtgcag ctggtgcag                                   29

<210> SEQ ID NO 16
<211> LENGTH: 27
<212> TYPE: DNA
<213> ORGANISM: Artificial
<220> FEATURE:
<223> OTHER INFORMATION: Olidonucleotide primer.

<400> SEQUENCE: 16
cgaattcacc taggacggtc agcttgg                                     27

<210> SEQ ID NO 17
<211> LENGTH: 32
<212> TYPE: DNA
<213> ORGANISM: Artificial
<220> FEATURE:
<223> OTHER INFORMATION: Olidonucleotide primer.

<400> SEQUENCE: 17
gggaagcttc aggtgcagct ggtgcagtct gg                               32

<210> SEQ ID NO 18
<211> LENGTH: 33
<212> TYPE: DNA
<213> ORGANISM: Artificial
<220> FEATURE:
<223> OTHER INFORMATION: Olidonucleotide primer.

<400> SEQUENCE: 18
```

```
gggctcgaga cctaggacgg tcagcttggt tcc                              33
```

<210> SEQ ID NO 19
<211> LENGTH: 243
<212> TYPE: PRT
<213> ORGANISM: Artificial
<220> FEATURE:
<223> OTHER INFORMATION: Synthetic antibody.

<400> SEQUENCE: 19

```
Met Ala Gln Val Gln Leu Val Glu Ser Gly Gly Val Val Gln Pro
1               5                   10                  15

Gly Arg Ser Leu Arg Leu Ser Cys Ala Ala Ser Gly Phe Thr Phe Ser
            20                  25                  30

Ser Tyr Gly Met His Trp Val Arg Gln Ala Pro Gly Lys Gly Leu Glu
        35                  40                  45

Trp Val Ala Val Ile Ser Tyr Asp Gly Ser Asn Lys Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Glu Tyr
                85                  90                  95

Tyr Cys Ala Lys Tyr Pro Leu Asn Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Gln Ser Ala Leu Thr Gln Pro Ala Ser Val Ser Gly Ser Pro
    130                 135                 140

Gly Gln Ser Ile Thr Ile Ser Cys Thr Gly Thr Ser Ser Asp Val Gly
145                 150                 155                 160

Gly Tyr Asn Tyr Ala Ser Trp Tyr Gln Gln His Pro Gly Lys Ala Pro
                165                 170                 175

Lys Leu Met Ile Tyr Glu Val Ser Asn Arg Pro Ser Gly Val Phe Asn
            180                 185                 190

Arg Phe Ser Gly Ala Lys Ser Gly Asn Thr Ala Ser Leu Thr Ile Ser
        195                 200                 205

Gly Leu Gln Ala Glu Asp Glu Ala Asp Tyr Tyr Cys Asn Ser Tyr Thr
    210                 215                 220

Ser Ser Ser Thr Trp Val Phe Gly Gly Gly Thr Lys Leu Thr Val Leu
225                 230                 235                 240

Gly Asn Ser
```

<210> SEQ ID NO 20
<211> LENGTH: 729
<212> TYPE: DNA
<213> ORGANISM: Artificial
<220> FEATURE:
<223> OTHER INFORMATION: Nucleic acid encoding single chain antibody.

<400> SEQUENCE: 20

```
atggcccagg tgcagctggt ggagtctggg ggaggcgtgg tccagcctgg gaggtccctg    60
agactctcct gtgcagcctc tggattcacc ttcagtagct atggcatgca ctgggtccgc   120
caggctccag gcaaggggct ggagtgggtg gcagttatat catatgatgg aagtaataaa   180
tactatgcag actccgtgaa gggccgattc accatctcca gagacaattc caagaacacg   240
ctgtatctgc aaatgaacag cctgagagct gaggacacgc tgagtatta ctgtgcgaag    300
```

```
tatcctttaa actggggcca gggaaccctg gtcaccgtct cctcaggtgg aggcggttca    360
ggcggaggtg gctctggcgg tggcggatcg cagtctgctc tgactcagcc tgcctccgtg    420
tctgggtctc ctggacagtc gatcaccatc tcctgcactg gaaccagcag tgacgttggt    480
ggttataact atgcttcctg gtaccaacag cacccaggca aggcccccaa actcatgatt    540
tatgaggtca gtaatcggcc ctcaggggtt ttcaatcgct tctctggcgc caagtctggc    600
aacacggcct ccctgaccat ctctgggctc caggctgagg acgaggctga ttattactgc    660
aactcatata caagcagcag cacttgggtg ttcggcggag ggaccaagct gaccgtccta    720
gggaattcc                                                             729
```

```
<210> SEQ ID NO 21
<211> LENGTH: 295
<212> TYPE: PRT
<213> ORGANISM: Artificial
<220> FEATURE:
<223> OTHER INFORMATION: Synthetic antibody.

<400> SEQUENCE: 21
```

Met Ala Gln Val Gln Leu Gln Glu Ser Gly Gly Gly Val Val Gln Pro
1               5                   10                  15

Gly Arg Ser Leu Arg Leu Ser Cys Ala Ala Ser Gly Phe Thr Phe Lys
            20                  25                  30

Ser Tyr Gly Met His Trp Val Arg Gln Ala Pro Gly Lys Gly Leu Glu
        35                  40                  45

Trp Val Ser Ala Ile Ser Ala Ser Gly Gly Ser Thr Tyr Tyr Ala Asp
    50                  55                  60

Ser Val Lys Gly Arg Phe Thr Ile Phe Arg Asp Asn Ser Glu Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Ser Gly Ser Phe Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Asp Ile Val Met Thr Gln Ser Pro Ser Thr
130                 135                 140

Leu Ser Ala Ser Ile Gly Asp Arg Val Thr Ile Thr Cys Arg Ala Ser
145                 150                 155                 160

Glu Gly Ile Tyr His Trp Leu Ala Trp Tyr Gln Gln Lys Pro Gly Lys
                165                 170                 175

Ala Pro Lys Leu Leu Ile Tyr Lys Ala Ser Ser Leu Ala Ser Gly Ala
            180                 185                 190

Pro Ser Arg Phe Ser Gly Ser Gly Ser Gly Thr Asp Thr Ile Thr Cys
        195                 200                 205

Arg Ala Ser Glu Gly Ile Tyr His Trp Leu Ala Trp Tyr Gln Gln Lys
    210                 215                 220

Pro Gly Lys Ala Pro Lys Leu Leu Ile Tyr Lys Ala Ser Ser Leu Ala
225                 230                 235                 240

Ser Gly Ala Pro Ser Arg Phe Ser Gly Ser Gly Ser Gly Thr Asp Phe
                245                 250                 255

Thr Leu Thr Ile Ser Ser Leu Gln Ala Glu Asp Val Ala Val Tyr Tyr
            260                 265                 270

Cys Gln Gln Tyr Tyr Arg Ser Pro Leu Thr Phe Gly Gly Gly Thr Lys
        275                 280                 285

```
Leu Glu Asn Lys Arg Asn Ser
    290             295
```

<210> SEQ ID NO 22
<211> LENGTH: 885
<212> TYPE: DNA
<213> ORGANISM: Artificial
<220> FEATURE:
<223> OTHER INFORMATION: Nucleic acid encoding single chain antibody.

<400> SEQUENCE: 22

| | | | | | |
|---|---|---|---|---|---|
| atggcccagg | tgcagctgca | ggagtcgggg | ggaggcgtgg | tccagcctgg | gaggtccctg | 60 |
| agactctcct | gtgcagcgtc | cggattcacc | ttcaagagct | atggcatgca | ctgggtccgc | 120 |
| caggctccag | gaaggggct | ggagtgggtc | tcagctatta | gtgctagtgg | tggtagcaca | 180 |
| tactacgcag | actccgtgaa | gggccgcttc | accatcttca | gagacaattc | cgagaactca | 240 |
| ctgtatcttc | aaatgaacag | cctgagagcc | gaggacacgg | ccgtctatta | ctgtgcgaga | 300 |
| gattcaagtg | ggtcctttga | ctactgggc | cagggaaccc | tggtcaccgt | ctcctcaggt | 360 |
| ggaggcggtt | caggcggagg | tggctctggc | ggtggcggat | cggacatcgt | gatgacccag | 420 |
| tctccttcca | ccctgtccgc | atctattgga | gacagagtca | ccatcacctg | ccgggccagt | 480 |
| gagggtattt | atcactggtt | ggcctggtat | cagcagaagc | cagggaaagc | ccctaaactc | 540 |
| ctgatctata | aggcctctag | tttagccagt | ggggccccat | caaggttcag | cggcagtgga | 600 |
| tctgggacag | ataccatcac | ctgccgggcc | agtgagggta | tttatcactg | gttggcctgg | 660 |
| tatcagcaga | agccagggaa | agcccctaaa | ctcctgatct | ataaggcctc | tagtttagcc | 720 |
| agtggggccc | catcaaggtt | cagcggcagt | ggatctggga | cagatttcac | tctcaccatc | 780 |
| agcagcctgc | aggctgaaga | tgtggcagta | tactactgtc | agcaatatta | tagaagtccg | 840 |
| ctcactttcg | gtggagggac | caagctggag | aacaaacgga | attcc | | 885 |

<210> SEQ ID NO 23
<211> LENGTH: 5
<212> TYPE: PRT
<213> ORGANISM: Artificial
<220> FEATURE:
<223> OTHER INFORMATION: Translocation signaling sequence.

<400> SEQUENCE: 23

```
Arg Glu Asp Leu Lys
1               5
```

<210> SEQ ID NO 24
<211> LENGTH: 4
<212> TYPE: PRT
<213> ORGANISM: Artificial
<220> FEATURE:
<223> OTHER INFORMATION: Translocation signaling sequence.

<400> SEQUENCE: 24

```
Arg Glu Asp Leu
1
```

<210> SEQ ID NO 25
<211> LENGTH: 4
<212> TYPE: PRT
<213> ORGANISM: Artificial
<220> FEATURE:
<223> OTHER INFORMATION: Translocation signaling sequence.

<400> SEQUENCE: 25

```
Arg Asp Glu Leu
```

```
<210> SEQ ID NO 26
<211> LENGTH: 4
<212> TYPE: PRT
<213> ORGANISM: Artificial
<220> FEATURE:
<223> OTHER INFORMATION: Translocation signaling sequence.

<400> SEQUENCE: 26

Lys Asp Glu Leu
1

<210> SEQ ID NO 27
<211> LENGTH: 873
<212> TYPE: DNA
<213> ORGANISM: Artificial
<220> FEATURE:
<223> OTHER INFORMATION: Nucleic acid encoding single chain antibody.

<400> SEQUENCE: 27
atgaaatacc tattgcctac ggcagccgct ggattgttat tactcgcggc ccagccggcc      60
atggcccagg tgcagctggt ggagtctggg ggaggcttgg tacagcctgg ggggtccctg     120
agactctcct gtgcagcctc tggattcacc tttcgcagct atgccatgag ctgggtccgc     180
caggctccag gaaggggct ggagtgggtc tcagctatta gtggtcgtgg tgataacaca     240
tactacgcag actccgtgaa gggccggttc accatctcca gagacaattc caagaacacg     300
ctgtatctgc aaatgaacag cctgagagcc gaggacacgg ccgtttatta ctgtgcgaaa     360
atgacaagta acgcgttcgc atttgactac tggggccagg gaaccctggt caccgtctcc     420
tcaggtggag gcggttcagg cggaggtggc tctggcggtg gcggatcgca gtctgtgttg     480
acgcagccgc cctcagtgtc tggggcccca gggcagaggg tcaccatctc ctgcactggg     540
agcagctcca acatcggggc aggttatgat gtacactggt accagcagct tccaggaaca     600
gcccccaaac tcctcatcta tggtaacacc aatcggccct caggggtccc tgaccgattc     660
tctggcttca gtctggcac ctcagcctcc ctggccatca ctgggctcca ggctgaggat     720
gaggctgatt attactgcca gtcctatgac agcagcctga gtggttgggt gttcggcgga     780
gggaccaagc tgaccgtcct aggtgcggcc gcagaacaaa aactcatctc agaagaggat     840
ctgaatgggg ccgcacatca ccatcatcac cat                                  873

<210> SEQ ID NO 28
<211> LENGTH: 873
<212> TYPE: DNA
<213> ORGANISM: Artificial
<220> FEATURE:
<223> OTHER INFORMATION: Nucleic acid encoding single chain antibody.

<400> SEQUENCE: 28
atgaaatacc tattgcctac ggcagccgct ggattgttat tactcgcggc ccagccggcc      60
atggcccagg tgcagctggt ggagtctggg ggaggcttgg tacagcctgg ggggtccctg     120
agactctcct gtgcagcctc tggattcacc tttcgcagct atgccatgag ctgggtccgc     180
caggctccag gaaggggct ggagtgggtc tcagctatta gtggtcgtgg tgataacaca     240
tactacgcag actccgtgaa gggccggttc accatctcca gagacaattc caagaacacg     300
ctgtatctgc aaatgaacag cctgagagcc gaggacacgg ccgtttatta ctgtgcgaaa     360
atgacaagta acgcgttcgc atttgactac tggggccagg gaaccctggt caccgtctcc     420
tcaggtggag gcggttcagg cggaggtggc tctggcggtg gcggatcgca gtctgtgttg     480
```

| | |
|---|---|
| acgcagccgc cctcagtgtc tggggcccca gggcagaggg tcaccatctc ctgcactggg | 540 |
| agcagctcca acatcggggc aggttatggt gtacactggt accagcagct tccaggaaca | 600 |
| gcccccaaac tcctcatcta tggtaacacc aatcggccct cagggtccc tgaccgattc | 660 |
| tctggcttca gtctggcac ctcagcctcc ctggccatca ctgggctcca ggctgaggat | 720 |
| gaggctgatt attactgcca gtcctatgac agcagcctga gtggttgggt gttcggcgga | 780 |
| gggaccaagc tgaccgtcct aggtgcggcc gcagaacaaa aactcatctc agaagaggat | 840 |
| ctgaatgggg ccgcacatca ccatcatcac cat | 873 |

<210> SEQ ID NO 29
<211> LENGTH: 864
<212> TYPE: DNA
<213> ORGANISM: Artificial
<220> FEATURE:
<223> OTHER INFORMATION: Nucleic acid encoding single chain antibody.

<400> SEQUENCE: 29

| | |
|---|---|
| atgaaatacc tattgcctac ggcagccgct ggattgttat tactcgcggc ccagccggcc | 60 |
| atggcccagg tacagctgca gcagtcaggg ggaggcctgg tcaaacctgg ggggtccctg | 120 |
| agactctcct gtgcagcctc tggattcacc ttcagtagct atagcatgaa ctgggtccgc | 180 |
| caggtcccag gaaggggct ggagtgggtc tcatccatta gtagtag tagttacata | 240 |
| tactacgcag actctgtgaa gggccgattc accatctcca gagacaatgc caagaactca | 300 |
| ctgtatctgc aaatgaacag cctgagagac gaggacacgg ctgtgtatta ctgtgcgaga | 360 |
| gatgacggtc cccccatcca gcactgggc cagggaaccc tggtcaccgt ctcctcacgt | 420 |
| ggaggcggtt caggcggagg tggctctggc ggtggcggat cgcagtctgt gttgagccag | 480 |
| ccgccctcgg tatctgggc cccagggcag agggtcacca tctcctgcac tgggagcagc | 540 |
| tccaacatcg gggcaagttt tgatgtacag tggtaccagc aacttccagg aacagccccc | 600 |
| aaactcctca tctatggtaa caacaatcgg ccctcagggg tccctgaccg attctctgcc | 660 |
| tccaagtctg gcacctcagc ctccctgggc atcaccggac tccagatcgg gacgaggcc | 720 |
| gattattact gcggctcata tacaggcacc tactcttggg tgttcggcgg agggaccaag | 780 |
| gtcaccgtcc taggtgcggc cgcagaacaa aaactcatct cagaagagga tctgaatggg | 840 |
| gccgcacatc accatcatca ccat | 864 |

<210> SEQ ID NO 30
<211> LENGTH: 870
<212> TYPE: DNA
<213> ORGANISM: Artificial
<220> FEATURE:
<223> OTHER INFORMATION: Nucleic acid encoding single chain antibody.

<400> SEQUENCE: 30

| | |
|---|---|
| atgaaatacc tattgccgac ggcagccgct ggattgttat tactcgcggc ccagccggcc | 60 |
| atggcccagg tgcagctgca ggagtcgggg ggaggcttgg tcaagcctgg ggggtccctg | 120 |
| agactctcct gtgcagcctc tggattcacc tttagtagct attggatgag ctgggtccgc | 180 |
| caggctccag gaaagggct ggagtgggtc gccaacataa accgcgatgg aagtgccagt | 240 |
| tattatgtgg actctgtgaa gggccgattc accatctcca gagacgacgc caagaactca | 300 |
| ctgtatctgc aaatgaacag cctgagagcc gaggacacgg ctgtgtatta ctgtgcgaga | 360 |
| gatcggggcg tggggtactt cgatctctgg ggccgtggca ccctggtcac cgtctcctca | 420 |
| ggtggaggcg gttcaggcgg aggtggctct ggcggtggcg gatcgcagtc tgccctgact | 480 |

```
cagcctgcct ccgtgtctgg atctcctgga cagtcgatca ccatctcctg cactggaacc      540
agcagtgatg ttggtggtta aactttgtc tcctggtacc aacagcaccc aggcaaagcc       600
cccaaactca tgatttatga tgtcagtgat cgaccctcag ggtctctga tcggttctct       660 ggctccaagt ctggcaacac ggcctccctg atcatctctg gcctccaggc tgacgacgag      720
gctgattatt actgcagctc atatggaagc agcagcaccc atgtgatttt cggcggaggg      780
accaaggtca ccgtcctagg tgcggccgca gaacaaaaac tcatctcaga agaggatctg      840
aatggggccg cacatcacca tcatcaccat                                       870
```

<210> SEQ ID NO 31
<211> LENGTH: 861
<212> TYPE: DNA
<213> ORGANISM: Artificial
<220> FEATURE:
<223> OTHER INFORMATION: Nucleic acid encoding single chain antibody.

<400> SEQUENCE: 31

```
atgaaatacc tattgcctac ggcagccgct ggattgttat tactcgcggc ccagccggcc      60
atggcccagg tgcagctggt ggagtctggg ggaggcgtgg tccagcctgg gaggtccctg     120
agactctcct gtgcagcctc tggattcacc ttcagtgact attatataca ctgggtccgc    180
caggctccag gcaaggggct ggagtggatg gcagttattt catatgatgg caataataaa    240
tactacgccg cctccgtgaa ggaccgattc accatctcca gagacaattc aagaacacg     300 gtgtctctgc aaatgaacag cctgagagct gaggacacgg ctgtgtatta ctgtgcgaga    360
gatctctacg gtgactacgc tcttgactac tggggccagg gaaccctggt caccgtctcc    420
tcaggtggag gcggttcagg cggaggtggc tctggcggtg gcggatcgga catccagatg   480
acccagtctc cttccaccct gtctgcatct ctgggagaca gagtcaccat cacttgccgg    540
gccagtcaga gtattggtag ctggttggcc tggtatcagc agaaaccagg aaagcccct    600 aaactcctga tctataaggc gtctacttta gaaagtgggg tcccatcaag gttcaccggc   660
agtggatctg ggacagaatt cactctcaca atcagcggcc tccagcctga agattttgca   720
acttattact gtcagaagct agtagttac ccgctcactt tcggcggagg gaccaaggtg    780
gaaatcaaac gtgcggccgc agaacaaaaa ctcatctcag aagaggatct gaatggggcc   840
gcacatcacc atcatcacca t                                             861
```

<210> SEQ ID NO 32
<211> LENGTH: 873
<212> TYPE: DNA
<213> ORGANISM: Artificial
<220> FEATURE:
<223> OTHER INFORMATION: Nucleic acid encoding single chain antibody.

<400> SEQUENCE: 32

```
atgaaatacc tattgcctac ggcagccgct ggattgttat tactcgcggc ccagccggcc     60
atggcccagg tgcagctggt gcagtctggg ggaggcttgg tacagcctgg caggtccctg   120
agactctcct gtgcagcctc tggattcacc tttgatgatt atgccatgca ctgggtccgg   180
caagctccag ggaagggcct ggagtgggtc tcaggtatta gttggaatag tggtagcata   240
ggctatgcgg actctgtgaa gggccgattc accatctcca gagacaacgc caagaactca   300
ctgtatctgc aaatgaacag cctgagacct gaggacacgg ctgtgtatta ctgtgcgaga   360
gatcttggtg ccaagcagtg gctggagggg tttgactact ggggccaggg caccctggtc   420
accgtctcct caggtggagg cggttcaggc ggaggtggct ctggcggtgg cggatcgaat   480
```

```
tttatgctga ctcaggaccc tgctgtgtct gtggccttgg gacagacagt caggatcaca    540
tgccaaggag acagcctcag aagctattat gcaagctggt accagcagaa gccaggacag    600
gcccctgtac ttgtcatcta tggtaaaaac aaccggccct cagggatccc agaccgattc    660
tctggctcca cctcaggaaa ctcagcttcc ttgaccatca ctgggctcag gcggaagat     720 gaggctgact attactgtaa ctcccgggac agcagtggta accattgggt gttcggcgga    780
gggaccaagg tcaccgtcct aggtgcggcc gcagaacaaa aactcatctc agaagaggat    840
ctgaatgggg ccgcacatca ccatcatcac cat                                 873
```

<210> SEQ ID NO 33
<211> LENGTH: 885
<212> TYPE: DNA
<213> ORGANISM: Artificial
<220> FEATURE:
<223> OTHER INFORMATION: Nucleic acid encoding single chain antibody.

<400> SEQUENCE: 33

```
atgaaatacc tattgcctac ggcagccgct ggattgttat tactcgcggc ccagccggcc     60
atggccgagg tgcagctggt gcagtctggg gctgaggtga agaagcctgg gtcctcggtg    120
aaggtctcct gcaaggcttc tggaggcacc ttcagcagct atgctatcag ctgggtgcga    180
caggcccctg gacaaggcct tgagtggatg ggagggatca tccctatctt tggtacagca    240
aactacgcac agaagttcca gggcagagtc acgattaccg cggacgaatc cacgagcaca    300
gcctacatgg aggtgagcag cctgagatct gaggacacgg ccgtgtatta ctgtgcgaga    360
gaggaggggc catattgtag tagtaccagc tgctatgggg ctttttgatat ctggggccaa    420 ggcacccctgg tcaccgtctc ctcaggtgga ggcggttcag gcggaggtgg ctctggcggt    480
ggcggatcgc agtctgtgct gactcaggac cctgctgtgt ctgtggcctt gggacagaca    540
gtcaagatca catgccaagg agacagcctc agaagctatt ttgcaagctg gtaccagcag    600
aagccaggac aggcccctac acttgtcatg tatgctagaa atgaccggcc cgcaggggtc    660
cctgaccgat tctctggctc caagtctggc acctcagcct ccctggccat cagtgggctc    720
cagtctgagg atgaggctga ttattattgt gcagcatggg atgacagcct gaatggttat    780
ctcttcggag ctgggaccaa gctgaccgtc ctaggtgcgg ccgcagaaca aaaactcatc    840
tcagaagagg atctgaatgg ggccgcacat caccatcatc accat                    885
```

<210> SEQ ID NO 34
<211> LENGTH: 861
<212> TYPE: DNA
<213> ORGANISM: Artificial
<220> FEATURE:
<223> OTHER INFORMATION: Nucleic acid encoding single chain antibody.

<400> SEQUENCE: 34

```
atgaaatacc tattgcctac ggcagccgct ggattgttat tactcgcggc ccagccggcc     60
atggcccagg tgcagctgca ggagtcgggc ccaggactgg tgaagccttc ggagaccctg    120
tccctcacct gcactgtctc tggtggctcc ttcagaagtt actactggag ctggatccgg    180
tagcccccag ggaagggact ggagtggata gggtatatct tttacagtgg gagcaccaac    240
tacaatccct ccctcaagag tcgagtcacc atatcagtag acacgtccaa gaaccagttc    300
tccctgaagc tgagctcttt gaccgctgcg gacacggccg tgtattattg tgcgagagga    360
catttgggga gttaggatgg ttcgacccc tggggccagg gaaccctggt caccgtctcc    420
tcaagtggag gcggttcagg cggaggtggc tctggcggtg gcggatcgga catccagatg    480
```

| | |
|---|---|
| acccagtctc catcctccct gtctgcatct gtaggagaca gagtcaccat cacttgccag | 540 |
| gcgagtcagg acattagcaa ctatttaaat tggtatcagc agaagccggg gaaagcccct | 600 |
| aaactcctga tctttgctgc atcccgttta gcgagcgggg tcccctcaag attcagcggc | 660 |
| agtggatctg gcacagattt cagtctcacc atcagcagcc tgcagcctga cgattttgca | 720 |
| acttattatt gtctacaaga ttccgattac cccctcactt tcggcggagg gaccaaggtg | 780 |
| gaaatcaaac gtgcggccgc agaacaaaaa ctcatctcag aagaggatct gaatgggggcc | 840 |
| gcacatcacc atcatcacca t | 861 |

<210> SEQ ID NO 35
<211> LENGTH: 873
<212> TYPE: DNA
<213> ORGANISM: Artificial
<220> FEATURE:
<223> OTHER INFORMATION: Synthetic antibody.

<400> SEQUENCE: 35

| | |
|---|---|
| atgaaatacc tattgcctac ggcagccgct ggattgttat tactcgcggc ccagccggcc | 60 |
| atggcccagg tgcagctgtt gcagttcggg ggaggcttgg tacagcctgg ggggtccctg | 120 |
| agactctcct gtgcagcctc tggattcacc tttagcagct atgccatgag ctgggtccgc | 180 |
| caggctccag ggaaggggct ggagtggctg tcagctatta gtggtagtgg tggtagcaca | 240 |
| tactacgcag actccgtgaa gggccggttc accatctcca gagacaattc caagaacacg | 300 |
| ctgtatctgc aaatgaacag cctgagagcc gaggacacgg ccgtatatta ctgtgcaaga | 360 |
| gagggatata gcagcaactg gaataactgg tacttcgatc tctggggccg tggcacccctg | 420 |
| gtcaccgtct cctcaggtgg aggcggttca ggcggaggtg gctctggcgg tggcggatcg | 480 |
| gatgttgtga tgactcagtc tccatcctcc ctgtctgcat ctgtaggaga cagagtcacc | 540 |
| atcacttgcc gggcaagtca gagcattagc agctatttaa attggtatca gcagaaacca | 600 |
| gggaaggccc ctgaactcct gatctatgct gcatcccgtt tacaaagtgg ggtcccatca | 660 |
| aggttcagtg gcagtggatc tgggaccgaa ttcactctca ccatcagcag cctgcagcct | 720 |
| gatgattttg caacttatta ctgccaacaa tattataatt atccgtggac gttcggccga | 780 |
| gggaccaagg tggaaatcaa acgtgcggcc gcagaacaaa aactcatctc agaagaggat | 840 |
| ctgaatgggg ccgcacatca ccatcatcac cat | 873 |

<210> SEQ ID NO 36
<211> LENGTH: 873
<212> TYPE: DNA
<213> ORGANISM: Artificial
<220> FEATURE:
<223> OTHER INFORMATION: Nucleic acid encoding single chain antibody.

<400> SEQUENCE: 36

| | |
|---|---|
| atgaaatacc tattgcctac ggcagccgct ggattgttat tactcgcggc ccagccggcc | 60 |
| atggcccagg tgcagctgca ggagtcgggg ggaggcatgg tccagcctgg gaggtccctg | 120 |
| agactctcct gtgcagcctc tggattcacc tttagcagct atgccatgag ctgggtccgc | 180 |
| caggctccag ggaaggggct ggagtgggtc tcagctatta gtggtagtgg tggtagcaca | 240 |
| tactacgcag actccgtgaa gggccggttc accatctcca gagacaattc caagaacacg | 300 |
| ctgtatctgc aaatgaacag cctgagagcc gaggacacgg ccctgtatta ctgtgcaaga | 360 |
| gagggatata gcagcaactg gaataactgg tacttcgatc tctggggccg tggcacccctg | 420 |
| gtcaccgtct cctcaggtgg aggcggttca ggcggaggtg gctctggcgg tggcggatcg | 480 |

```
gaaattgtgc tgactcagtc tccatcctcc ctgtctgcat ctgtaggaga cagagtcacc      540
atcacttgcc gggcaagtca gagcattagc agctatttaa attggtatca gcagaaacca      600
gggaaagccc ctaagctcct gatctatgct gcatccagtt tgcaaagtgg ggtcccatca      660
aggttcagtg gcagtggatc tgggacagat ttcactctca ccatcagcag cctgcagcct      720
gacgattttg caacttatta ctgccaacag tataatagtt acccttggac gttcggccaa      780
gggaccaagc tggagatcaa acgtgcggcc gcagaacaaa aactcatctc agaagaggat      840
ctgaatgggg ccgcacatca ccatcatcac cat                                   873
```

<210> SEQ ID NO 37
<211> LENGTH: 20
<212> TYPE: PRT
<213> ORGANISM: Artificial
<220> FEATURE:
<223> OTHER INFORMATION: Peptide linker.

<400> SEQUENCE: 37

Asn Ser Gly Ala Gly Thr Ser Gly Ser Gly Ala Ser Gly Glu Gly Ser
1               5                   10                  15

Gly Ser Lys Leu
            20

<210> SEQ ID NO 38
<211> LENGTH: 129
<212> TYPE: PRT
<213> ORGANISM: Artificial
<220> FEATURE:
<223> OTHER INFORMATION: Artificial antibody VH sequence.

<400> SEQUENCE: 38

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Cys Ser Ser Ser Asn Cys Ala Lys Trp
            100                 105                 110

Pro Glu Tyr Phe Gln His Trp Gly Gln Gly Thr Leu Val Thr Val Ser
        115                 120                 125

Ser

<210> SEQ ID NO 39
<211> LENGTH: 129
<212> TYPE: PRT
<213> ORGANISM: Artificial
<220> FEATURE:
<223> OTHER INFORMATION: Artificial antibody VH sequence.

<400> SEQUENCE: 39

Gln Val Gln Leu Val Gln Ser Gly Ala Glu Val Lys Lys Pro Gly Glu
1               5                   10                  15

```
Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Ala Tyr Cys Ser Ser Ser Asn Cys Ala Lys Trp
            100                 105                 110

Pro Glu Tyr Phe Gln His Trp Gly Gln Gly Thr Leu Val Thr Val Ser
        115                 120                 125

Ser
```

```
<210> SEQ ID NO 40
<211> LENGTH: 129
<212> TYPE: PRT
<213> ORGANISM: Artificial
<220> FEATURE:
<223> OTHER INFORMATION: Artificial antibody VH sequence.

<400> SEQUENCE: 40

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Cys Ser Ser Ser Asn Cys Ala Lys Trp
            100                 105                 110

Pro Glu Tyr Phe Gln His Trp Gly Gln Gly Thr Leu Val Thr Val Ser
        115                 120                 125

Ser
```

```
<210> SEQ ID NO 41
<211> LENGTH: 129
<212> TYPE: PRT
<213> ORGANISM: Artificial
<220> FEATURE:
<223> OTHER INFORMATION: Artificial antibody VH sequence.

<400> SEQUENCE: 41

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60
```

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
            85                  90                  95

Ala Arg His Asp Val Gly Tyr Cys Thr Asp Arg Thr Cys Ala Lys Trp
            100                 105                 110

Pro Glu Tyr Phe Gln His Trp Gly Gln Gly Thr Leu Val Thr Val Ser
        115                 120                 125

Ser

<210> SEQ ID NO 42
<211> LENGTH: 129
<212> TYPE: PRT
<213> ORGANISM: Artificial
<220> FEATURE:
<223> OTHER INFORMATION: Artificial antibody VH sequence.

<400> SEQUENCE: 42

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Ala Trp Val Arg Gln Met Pro Gly Lys Gly Leu Glu Tyr Met
            35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
            85                  90                  95

Ala Arg His Asp Val Gly Tyr Cys Thr Asp Arg Thr Cys Ala Lys Trp
            100                 105                 110

Pro Glu Trp Leu Gly Val Trp Gly Gln Gly Thr Leu Val Thr Val Ser
        115                 120                 125

Ser

<210> SEQ ID NO 43
<211> LENGTH: 111
<212> TYPE: PRT
<213> ORGANISM: Artificial
<220> FEATURE:
<223> OTHER INFORMATION: Artificial antibody VL sequence.

<400> SEQUENCE: 43

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Gly His Thr Asn Arg Pro Ala Gly Val Pro Asp Arg Phe Ser
    50                  55                  60

Gly Ser Lys Ser Gly Thr Ser Ala Ser Leu Ala Ile Ser Gly Phe Arg
65                  70                  75                  80

Ser Glu Asp Glu Ala Asp Tyr Tyr Cys Ala Ala Trp Asp Asp Ser Leu
            85                  90                  95

Ser Gly Trp Val Phe Gly Gly Gly Thr Lys Leu Thr Val Leu Gly

<210> SEQ ID NO 44
<211> LENGTH: 111
<212> TYPE: PRT
<213> ORGANISM: Artificial
<220> FEATURE:
<223> OTHER INFORMATION: Artificial antibody VL sequence.

<400> SEQUENCE: 44

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Gly His Thr Asn Arg Pro Ala Gly Val Pro Asp Arg Phe Ser
    50                  55                  60

Gly Ser Lys Ser Gly Thr Ser Ala Ser Leu Ala Ile Ser Gly Phe Arg
65                  70                  75                  80

Ser Glu Asp Glu Ala Asp Tyr Tyr Cys Ala Ser Trp Asp Tyr Thr Leu
                85                  90                  95

Ser Gly Trp Val Phe Gly Gly Gly Thr Lys Leu Thr Val Leu Gly
            100                 105                 110

<210> SEQ ID NO 45
<211> LENGTH: 111
<212> TYPE: PRT
<213> ORGANISM: Artificial
<220> FEATURE:
<223> OTHER INFORMATION: Artificial antibody VL sequence.

<400> SEQUENCE: 45

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp His Thr Asn Arg Pro Ala Gly Val Pro Asp Arg Phe Ser
    50                  55                  60

Gly Ser Lys Ser Gly Thr Ser Ala Ser Leu Ala Ile Ser Gly Phe Arg
65                  70                  75                  80

Ser Glu Asp Glu Ala Asp Tyr Tyr Cys Ala Ser Trp Asp Tyr Thr Leu
                85                  90                  95

Ser Gly Trp Val Phe Gly Gly Gly Thr Lys Leu Thr Val Leu Gly
            100                 105                 110

<210> SEQ ID NO 46
<211> LENGTH: 111
<212> TYPE: PRT
<213> ORGANISM: Artificial
<220> FEATURE:
<223> OTHER INFORMATION: Artificial antibody VL sequence.

<400> SEQUENCE: 46

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

```
Tyr Val Ser Trp Tyr Gln Gln Leu Pro Gly Thr Ala Pro Lys Leu Leu
            35                  40                  45

Ile Tyr Asp His Thr Asn Arg Pro Ala Gly Val Pro Asp Arg Phe Ser
    50                  55                  60

Gly Ser Lys Ser Gly Thr Ser Ala Ser Leu Ala Ile Ser Gly Phe Arg
65                  70                  75                  80

Ser Glu Asp Glu Ala Asp Tyr Tyr Cys Ala Ser Trp Asp Tyr Thr Leu
                85                  90                  95

Ser Gly Trp Val Phe Gly Gly Gly Thr Lys Val Thr Val Leu Gly
            100                 105                 110

<210> SEQ ID NO 47
<211> LENGTH: 111
<212> TYPE: PRT
<213> ORGANISM: Artificial
<220> FEATURE:
<223> OTHER INFORMATION: Artificial antibody VL sequence.

<400> SEQUENCE: 47

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
            35                  40                  45

Ile Tyr Asp His Thr Asn Arg Pro Ala Gly Val Pro Asp Arg Phe Ser
    50                  55                  60

Gly Ser Lys Ser Gly Thr Ser Ala Ser Leu Ala Ile Ser Gly Phe Arg
65                  70                  75                  80

Ser Glu Asp Glu Ala Asp Tyr Tyr Cys Ala Ser Trp Asp Tyr Thr Leu
                85                  90                  95

Ser Gly Trp Val Phe Gly Gly Gly Thr Lys Val Thr Val Leu Gly
            100                 105                 110

<210> SEQ ID NO 48
<211> LENGTH: 129
<212> TYPE: PRT
<213> ORGANISM: Artificial
<220> FEATURE:
<223> OTHER INFORMATION: Artificial antibody VH sequence.

<400> SEQUENCE: 48

Gln Val Gln Leu Leu Gln Ser Gly Ala Glu Leu Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
            35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Cys Ser Ser Asn Cys Ala Lys Trp
            100                 105                 110

Pro Glu Tyr Phe Gln His Trp Gly Gln Gly Thr Leu Val Thr Val Ser
            115                 120                 125
```

-continued

Ser

<210> SEQ ID NO 49
<211> LENGTH: 129
<212> TYPE: PRT
<213> ORGANISM: Artificial
<220> FEATURE:
<223> OTHER INFORMATION: Artificial antibody VH sequence.

<400> SEQUENCE: 49

```
Gln Val Gln Leu Leu Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Ala Tyr Cys Ser Ser Ser Asn Cys Ala Lys Trp
            100                 105                 110

Pro Glu Tyr Phe Gln His Trp Gly Gln Gly Thr Leu Val Thr Val Ser
        115                 120                 125

Ser
```

<210> SEQ ID NO 50
<211> LENGTH: 129
<212> TYPE: PRT
<213> ORGANISM: Artificial
<220> FEATURE:
<223> OTHER INFORMATION: Artificial antibody VH sequence.

<400> SEQUENCE: 50

```
Gln Val Gln Leu Leu Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Cys Ser Ser Ser Asn Cys Ala Lys Trp
            100                 105                 110

Pro Glu Tyr Phe Gln His Trp Gly Gln Gly Thr Leu Val Thr Val Ser
        115                 120                 125

Ser
```

<210> SEQ ID NO 51
<211> LENGTH: 129
<212> TYPE: PRT
<213> ORGANISM: Artificial
<220> FEATURE:

<223> OTHER INFORMATION: Artificial antibody VH sequence.

<400> SEQUENCE: 51

Gln Val Gln Leu Leu Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Cys Thr Asp Arg Thr Cys Ala Lys Trp
            100                 105                 110

Pro Glu Tyr Phe Gln His Trp Gly Gln Gly Thr Leu Val Thr Val Ser
        115                 120                 125

Ser

<210> SEQ ID NO 52
<211> LENGTH: 129
<212> TYPE: PRT
<213> ORGANISM: Artificial
<220> FEATURE:
<223> OTHER INFORMATION: Artificial antibody VH sequence.

<400> SEQUENCE: 52

Gln Val Gln Leu Leu Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Cys Thr Asp Arg Thr Cys Ala Lys Trp
            100                 105                 110

Pro Glu Trp Leu Gly Val Trp Gly Gln Gly Thr Leu Val Thr Val Ser
        115                 120                 125

Ser

<210> SEQ ID NO 53
<211> LENGTH: 111
<212> TYPE: PRT
<213> ORGANISM: Artificial
<220> FEATURE:
<223> OTHER INFORMATION: Artificial antibody VL sequence.

<400> SEQUENCE: 53

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn

```
                20                  25                  30
Tyr Val Ser Trp Tyr Gln Gln Leu Pro Gly Thr Ala Pro Lys Leu Leu
            35                  40                  45
Ile Tyr Gly His Thr Asn Arg Pro Ala Gly Val Pro Asp Arg Phe Ser
        50                  55                  60
Gly Ser Lys Ser Gly Thr Ser Ala Ser Leu Ala Ile Ser Gly Phe Arg
65                  70                  75                  80
Ser Glu Asp Glu Ala Asp Tyr Tyr Cys Ala Ala Trp Asp Asp Ser Leu
                85                  90                  95
Ser Gly Trp Val Phe Gly Gly Gly Thr Lys Leu Thr Val Leu Gly
            100                 105                 110

<210> SEQ ID NO 54
<211> LENGTH: 111
<212> TYPE: PRT
<213> ORGANISM: Artificial
<220> FEATURE:
<223> OTHER INFORMATION: Artificial antibody VL sequence.

<400> SEQUENCE: 54

Glu Ser Val Leu Thr Gln Pro Pro Ser Val Ser Ala Ala Pro Gly Gln
1               5                   10                  15
Lys Val Thr Ile Ser Cys Ser Gly Ser Ser Asn Ile Gly Asn Asn
            20                  25                  30
Tyr Val Ser Trp Tyr Gln Gln Leu Pro Gly Thr Ala Pro Lys Leu Leu
            35                  40                  45
Ile Tyr Asp His Thr Asn Arg Pro Ala Gly Val Pro Asp Arg Phe Ser
        50                  55                  60
Gly Ser Lys Ser Gly Thr Ser Ala Ser Leu Ala Ile Ser Gly Phe Arg
65                  70                  75                  80
Ser Glu Asp Glu Ala Asp Tyr Tyr Cys Ala Ser Trp Asp Tyr Thr Leu
                85                  90                  95
Ser Gly Trp Val Phe Gly Gly Gly Thr Lys Leu Thr Val Leu Gly
            100                 105                 110

<210> SEQ ID NO 55
<211> LENGTH: 111
<212> TYPE: PRT
<213> ORGANISM: Artificial
<220> FEATURE:
<223> OTHER INFORMATION: Artificial antibody VL sequence.

<400> SEQUENCE: 55

Glu Ser Val Leu Thr Gln Pro Pro Ser Val Ser Ala Ala Pro Gly Gln
1               5                   10                  15
Lys Val Thr Ile Ser Cys Ser Gly Ser Ser Asn Ile Gly Asn Asn
            20                  25                  30
Tyr Val Ser Trp Tyr Gln Gln Leu Pro Gly Thr Ala Pro Lys Leu Leu
            35                  40                  45
Ile Tyr Asp His Thr Asn Arg Pro Ala Gly Val Pro Asp Arg Phe Ser
        50                  55                  60
Gly Ser Lys Ser Gly Thr Ser Ala Ser Leu Ala Ile Ser Gly Phe Arg
65                  70                  75                  80
Ser Glu Asp Glu Ala Asp Tyr Tyr Cys Ala Ser Trp Asp Tyr Thr Leu
                85                  90                  95
Ser Gly Trp Val Phe Gly Gly Gly Thr Lys Leu Thr Val Leu Gly
            100                 105                 110
```

```
<210> SEQ ID NO 56
<211> LENGTH: 111
<212> TYPE: PRT
<213> ORGANISM: Artificial
<220> FEATURE:
<223> OTHER INFORMATION: Artificial antibody VL sequence.

<400> SEQUENCE: 56

Glu Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
            35                  40                  45

Ile Tyr Asp His Thr Asn Arg Pro Ala Gly Val Pro Asp Arg Phe Ser
50                  55                  60

Gly Ser Lys Ser Gly Thr Ser Ala Ser Leu Ala Ile Ser Gly Phe Arg
65                  70                  75                  80

Ser Glu Asp Glu Ala Asp Tyr Tyr Cys Ala Ser Trp Asp Tyr Thr Leu
                85                  90                  95

Ser Gly Trp Val Phe Gly Gly Gly Thr Lys Leu Thr Val Leu Gly
            100                 105                 110

<210> SEQ ID NO 57
<211> LENGTH: 111
<212> TYPE: PRT
<213> ORGANISM: Artificial
<220> FEATURE:
<223> OTHER INFORMATION: Artificial antibody VL sequence.

<400> SEQUENCE: 57

Glu Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
            35                  40                  45

Ile Tyr Asp His Thr Asn Arg Pro Ala Gly Val Pro Asp Arg Phe Ser
50                  55                  60

Gly Ser Lys Ser Gly Thr Ser Ala Ser Leu Ala Ile Ser Gly Phe Arg
65                  70                  75                  80

Ser Glu Asp Glu Ala Asp Tyr Tyr Cys Ala Ser Trp Asp Tyr Thr Leu
                85                  90                  95

Ser Gly Trp Val Phe Gly Gly Gly Thr Lys Leu Thr Val Leu Gly
            100                 105                 110

<210> SEQ ID NO 58
<211> LENGTH: 34
<212> TYPE: DNA
<213> ORGANISM: Artificial
<220> FEATURE:
<223> OTHER INFORMATION: PCR primer synthetic oligonucleotide.

<400> SEQUENCE: 58
gatataatgc ggccgctcag tggtggtggt ggtg                            34

<210> SEQ ID NO 59
<211> LENGTH: 5
<212> TYPE: PRT
<213> ORGANISM: Artificial
<220> FEATURE:
<223> OTHER INFORMATION: Antibody CDR
```

<400> SEQUENCE: 59

Ser Tyr Trp Ile Ala
1               5

<210> SEQ ID NO 60
<211> LENGTH: 17
<212> TYPE: PRT
<213> ORGANISM: Artificial
<220> FEATURE:
<223> OTHER INFORMATION: Antibody CDR

<400> SEQUENCE: 60

Leu Ile Tyr Pro Gly Asp Ser Asp Thr Lys Tyr Ser Pro Ser Phe Gln
1               5                   10                  15

Gly

<210> SEQ ID NO 61
<211> LENGTH: 20
<212> TYPE: PRT
<213> ORGANISM: Artificial
<220> FEATURE:
<223> OTHER INFORMATION: Antibody CDR

<400> SEQUENCE: 61

His Asp Val Gly Tyr Cys Thr Asp Arg Thr Cys Ala Lys Trp Pro Glu
1               5                   10                  15

Trp Leu Gly Val
            20

<210> SEQ ID NO 62
<211> LENGTH: 13
<212> TYPE: PRT
<213> ORGANISM: Artificial
<220> FEATURE:
<223> OTHER INFORMATION: Antibody CDR

<400> SEQUENCE: 62

Ser Gly Ser Ser Ser Asn Ile Gly Asn Asn Tyr Val Ser
1               5                   10

<210> SEQ ID NO 63
<211> LENGTH: 7
<212> TYPE: PRT
<213> ORGANISM: Artificial
<220> FEATURE:
<223> OTHER INFORMATION: Antibody CDR

<400> SEQUENCE: 63

Asp His Thr Asn Arg Pro Ala
1               5

<210> SEQ ID NO 64
<211> LENGTH: 11
<212> TYPE: PRT
<213> ORGANISM: Artificial
<220> FEATURE:
<223> OTHER INFORMATION: Antibody CDR

<400> SEQUENCE: 64

Ala Ser Trp Asp Tyr Thr Leu Ser Gly Trp Val
1               5                   10

<210> SEQ ID NO 65
<211> LENGTH: 5
<212> TYPE: PRT

<213> ORGANISM: Artificial
<220> FEATURE:
<223> OTHER INFORMATION: Antibody CDR

<400> SEQUENCE: 65

Ser Tyr Trp Met Ser
1               5

<210> SEQ ID NO 66
<211> LENGTH: 17
<212> TYPE: PRT
<213> ORGANISM: Artificial
<220> FEATURE:
<223> OTHER INFORMATION: Antibody CDR

<400> SEQUENCE: 66

Asn Ile Asn Arg Asp Gly Ser Ala Ser Tyr Tyr Val Asp Ser Val Lys
1               5                   10                  15

Gly

<210> SEQ ID NO 67
<211> LENGTH: 9
<212> TYPE: PRT
<213> ORGANISM: Artificial
<220> FEATURE:
<223> OTHER INFORMATION: Antibody CDR

<400> SEQUENCE: 67

Asp Arg Gly Val Gly Tyr Phe Asp Leu
1               5

<210> SEQ ID NO 68
<211> LENGTH: 14
<212> TYPE: PRT
<213> ORGANISM: Artificial
<220> FEATURE:
<223> OTHER INFORMATION: Antibody CDR

<400> SEQUENCE: 68

Thr Gly Thr Ser Ser Asp Val Gly Gly Tyr Asn Phe Val Ser
1               5                   10

<210> SEQ ID NO 69
<211> LENGTH: 7
<212> TYPE: PRT
<213> ORGANISM: Artificial
<220> FEATURE:
<223> OTHER INFORMATION: Antibody CDR

<400> SEQUENCE: 69

Asp Val Ser Asp Arg Pro Ser
1               5

<210> SEQ ID NO 70
<211> LENGTH: 11
<212> TYPE: PRT
<213> ORGANISM: Artificial
<220> FEATURE:
<223> OTHER INFORMATION: Antibody CDR

<400> SEQUENCE: 70

Ser Ser Tyr Gly Ser Ser Ser Thr His Val Ile
1               5                   10

<210> SEQ ID NO 71
<211> LENGTH: 30
<212> TYPE: PRT

<213> ORGANISM: Artificial
<220> FEATURE:
<223> OTHER INFORMATION: Antibody framework region

<400> SEQUENCE: 71

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr
            20                  25                  30

<210> SEQ ID NO 72
<211> LENGTH: 30
<212> TYPE: PRT
<213> ORGANISM: Artificial
<220> FEATURE:
<223> OTHER INFORMATION: Antibody framework region

<400> SEQUENCE: 72

Gln Val Gln Leu Leu Gln Ser Gly Ala Glu Val Lys Lys Pro Gly Glu
1               5                   10                  15

Ser Leu Lys Ile Ser Cys Lys Gly Ser Gly Tyr Ser Phe Thr
            20                  25                  30

<210> SEQ ID NO 73
<211> LENGTH: 14
<212> TYPE: PRT
<213> ORGANISM: Artificial
<220> FEATURE:
<223> OTHER INFORMATION: Antibody framework region

<400> SEQUENCE: 73

Trp Val Arg Gln Met Pro Gly Lys Gly Leu Glu Tyr Met Gly
1               5                   10

<210> SEQ ID NO 74
<211> LENGTH: 32
<212> TYPE: PRT
<213> ORGANISM: Artificial
<220> FEATURE:
<223> OTHER INFORMATION: Antibody framework region

<400> SEQUENCE: 74

Gln Val Thr Ile Ser Val Asp Lys Ser Val Ser Thr Ala Tyr Leu Gln
1               5                   10                  15

Trp Ser Ser Leu Lys Pro Ser Asp Ser Ala Val Tyr Phe Cys Ala Arg
            20                  25                  30

<210> SEQ ID NO 75
<211> LENGTH: 11
<212> TYPE: PRT
<213> ORGANISM: Artificial
<220> FEATURE:
<223> OTHER INFORMATION: Antibody framework region

<400> SEQUENCE: 75

Trp Gly Gln Gly Thr Leu Val Thr Val Ser Ser
1               5                   10

<210> SEQ ID NO 76
<211> LENGTH: 22
<212> TYPE: PRT
<213> ORGANISM: Artificial
<220> FEATURE:
<223> OTHER INFORMATION: Antibody framework region

<400> SEQUENCE: 76

Gln Ser Val Leu Thr Gln Pro Pro Ser Val Ser Ala Ala Pro Gly Gln
1               5                   10                  15

Lys Val Thr Ile Ser Cys
            20

<210> SEQ ID NO 77
<211> LENGTH: 22
<212> TYPE: PRT
<213> ORGANISM: Artificial
<220> FEATURE:
<223> OTHER INFORMATION: Antibody framework region

<400> SEQUENCE: 77

Glu Ser Val Leu Thr Gln Pro Pro Ser Val Ser Ala Ala Pro Gly Gln
1               5                   10                  15

Lys Val Thr Ile Ser Cys
            20

<210> SEQ ID NO 78
<211> LENGTH: 15
<212> TYPE: PRT
<213> ORGANISM: Artificial
<220> FEATURE:
<223> OTHER INFORMATION: Antibody framework region

<400> SEQUENCE: 78

Trp Tyr Gln Gln Leu Pro Gly Thr Ala Pro Lys Leu Leu Ile Tyr
1               5                   10                  15

<210> SEQ ID NO 79
<211> LENGTH: 32
<212> TYPE: PRT
<213> ORGANISM: Artificial
<220> FEATURE:
<223> OTHER INFORMATION: Antibody framework region

<400> SEQUENCE: 79

Gly Val Pro Asp Arg Phe Ser Gly Ser Lys Ser Gly Thr Ser Ala Ser
1               5                   10                  15

Leu Ala Ile Ser Gly Phe Arg Ser Glu Asp Glu Ala Asp Tyr Tyr Cys
            20                  25                  30

<210> SEQ ID NO 80
<211> LENGTH: 11
<212> TYPE: PRT
<213> ORGANISM: Artificial
<220> FEATURE:
<223> OTHER INFORMATION: Antibody framework region

<400> SEQUENCE: 80

Phe Gly Gly Gly Thr Lys Val Thr Val Leu Gly
1               5                   10

<210> SEQ ID NO 81
<211> LENGTH: 11
<212> TYPE: PRT
<213> ORGANISM: Artificial
<220> FEATURE:
<223> OTHER INFORMATION: Antibody framework region

<400> SEQUENCE: 81

Phe Gly Gly Gly Thr Lys Leu Thr Val Leu Gly
1               5                   10